(12) United States Patent
Zhao et al.

(10) Patent No.: US 12,011,482 B2
(45) Date of Patent: Jun. 18, 2024

(54) CHLORIN DERIVATIVES OR PHARMACEUTICALLY ACCEPTABLE SALTS THEREOF, PREPARATION METHOD AND USE THEREOF, AND COMBINATION THEREOF WITH AN ULTRASONIC MEDICAL SYSTEM

(71) Applicant: GUANGZHOU EEC BIOTECH DEVELOPMENT CO., LTD., Guangzhou (CN)

(72) Inventors: Weijie Zhao, Guangzhou (CN); Jiang'an Su, Guangzhou (CN); Qing Li, Guangzhou (CN); Xiaohuai Wang, Guangzhou (CN); Kun Shao, Guangzhou (CN); Bo Yu, Guangzhou (CN); Xiaqing Wang, Guangzhou (CN)

(73) Assignee: GUANGZHOU EEC BIOTECH DEVELOPMENT CO., LTD., Guangzhou (CN)

( * ) Notice: Subject to any disclaimer, the term of this patent is extended or adjusted under 35 U.S.C. 154(b) by 0 days.

(21) Appl. No.: 17/404,800

(22) Filed: Aug. 17, 2021

(65) Prior Publication Data

US 2022/0054636 A1 Feb. 24, 2022

(30) Foreign Application Priority Data

Aug. 18, 2020 (CN) .......................... 2020108332299
Aug. 18, 2020 (CN) .......................... 2020108332335

(51) Int. Cl.
*A61N 7/00* (2006.01)
*A61K 41/00* (2020.01)

(52) U.S. Cl.
CPC ............ *A61K 41/0071* (2013.01); *A61N 7/00* (2013.01); *A61N 2007/0004* (2013.01)

(58) Field of Classification Search
CPC ................................................ A61K 41/0071
See application file for complete search history.

(56) References Cited

FOREIGN PATENT DOCUMENTS

| CN | 103833762 A | 6/2014 |
|---|---|---|
| CN | 104327156 A | 2/2015 |
| CN | 105111219 A | 12/2015 |
| CN | 106046008 A | 10/2016 |
| CN | 107722075 A | 2/2018 |
| CN | 107722077 A | 2/2018 |
| CN | 107987081 A | 5/2018 |
| CN | 111943954 A | 11/2020 |
| CN | 113198117 A | 8/2021 |

OTHER PUBLICATIONS

Jinadasa et al. (2011) "Syntheses and Cellular Investigations of $17^3$-, $15^2$-, and $13^1$-Amino Acid Derivatives of Chlorin $e_6$," Journal of Medicinal Chemistry 54, 7464-7476.

Cao et al. (2017) "Synthesis and in vitro phototoxicity of novel p-extension derivatives of chlorin e6," New J. Chem. 41, 14279-142.

First Office Action and Search Report, corresponding to Chinese Patent Application No. 2020108332335, 14 pages.

CNIPA Novelty Search Report, for "Chlorin Derivatives or Pharmaceutically Acceptable Salts Thereof, Preparation Method and Use Thereof, and Combination Thereof with an Ultrasonic Medical System," dated Jul. 16, 2020, 16 pages.

Extended European Search Report dated Jan. 19, 2024 in corresponding European Application No. 21857691.6.

Kato et al. (2003) "Phase II clinical study of photodynamic therapy using mono-I-aspartyl chlorin e6 and diode laser for early superficial squamous cell carcinoma of the lung", Lung Cancer., vol. 42, No. 1, pp. 103-111.

Liu et al. (2008) "Cross-Metathesis of the Vinyl Group on Tetrapyrrolic Macrocycles: Reactivity, Selectivity, and Mechanism", The Journal of Organic Chemistry, vol. 73, No. 17, pp. 6542-6550.

(Continued)

*Primary Examiner* — Paul V Ward
(74) *Attorney, Agent, or Firm* — Leydig, Voit & Mayer, LTD.

(57) ABSTRACT

The present disclosure relates to a chlorin derivative or a pharmaceutically acceptable salt thereof, a preparation method thereof, an anti-tumor composition including the chlorin derivative or the pharmaceutically acceptable salt thereof, use of the chlorin derivative or the pharmaceutically acceptable salt thereof in the treatment of a tumor, and a combination of the chlorin derivative or the pharmaceutically acceptable salt thereof and an ultrasound medical system. The chlorin derivative or the pharmaceutically acceptable salt thereof has a structure represented by formula (I), and the ultrasonic medical system comprises a transducer ultrasonic bed and a contact agent. The chlorin derivative of the present disclosure can be used in photodynamic therapy and sonodynamic therapy, thereby effectively inhibiting and treating cancer.

30 Claims, 19 Drawing Sheets

(56) References Cited

OTHER PUBLICATIONS

Shi et al. (2011) "Pharmacokinetic study of a novel sonosensitizer chlorin-e6 and its sonodynamic anti-cancer activity in hepatoma-22 tumor bearing mice", Biopharmaceutics and Drug Disposition, Wiley, Chichester, US, vol. 32, No. 6, pp. 319-332.

Yumita et al. (2011) "Sonodynamically-induced Antitumor Effect of Mono-I-aspartyl Chlorin e6 (NPe6)", Anticancer research, pp. 501-506.

FIG. 24

CHLORIN DERIVATIVES OR PHARMACEUTICALLY ACCEPTABLE SALTS THEREOF, PREPARATION METHOD AND USE THEREOF, AND COMBINATION THEREOF WITH AN ULTRASONIC MEDICAL SYSTEM

CROSS-REFERENCE OF RELATED APPLICATIONS

This Application claims the benefit of and priority to CN Prov. App. Ser. No. 2020108332335 filed on Aug. 18, 2020, and CN Prov. App. Ser. No. 2020108332299 filed on Aug. 18, 2020, which are incorporated by reference in their entirety.

TECHNICAL FIELD

The present disclosure belongs to the field of biomedicine. particularly, the present disclosure relates to a chlorin derivative or a pharmaceutically acceptable salt thereof, and a preparation method thereof, an anti-tumor composition comprising the chlorin derivative or the pharmaceutically acceptable salt thereof, use of the chlorin derivative or a pharmaceutically acceptable salt thereof in the treatment of a tumor, and a combination of the chlorin derivative or the pharmaceutically acceptable salt thereof with an ultrasound medical system for comprehensive treatment of patients.

BACKGROUND OF THE INVENTION

Photodynamic therapy (PDT) and sonodynamic therapy (SDT) are modern medical technologies in which a photosensitizer or a sonosensitizer is excited by light or ultrasound, respectively, to induce a chemical reaction to kill tumor cells.

Photodyamic therapy (PDT) is a novel method for treating tumors or other diseases by using photosensitive drugs and laser irradiation. Particularly, photodynamic therapy is carried out by using a photosensitizer to generate singlet oxygen ($^1O_2$) and free radicals under radiation at a specific wavelength, so as to kill tumor cells. Compared with traditional treatment methods such as surgery, chemotherapy and radiotherapy, PDT has advantages such as less side effect on the body and no damage to internal organs, but it is inadequate in the treatment of tumors deep in the body. At present, it has been discovered in experimental studies that some photosensitive compounds also have ultrasound sensitivity.

Sonodynamic therapy (SDT) is a new therapy developed on the basis of photodynamic therapy (PDT) for the clinical treatment of malignant and tumors deep in the body. Ultrasound has the properties such as capability of penetrating the body, no-trauma and non-invasion. Just like molecular machines, the sound-sensitive molecules as used can target tumor tissues, which generate response to ultrasound power, operate efficiently and exert anti-tumor effects. Using ultrasound as the driving force, at the tumor site where the sonosensitizer is enriched, ultrasonic cavitation is formed, and singlet oxygen capable of killing tumor cells and related biochemical reactions are generated, which induce apoptosis or death of tumor cells and make superimposed effects on chemotherapy and photodynamic therapy, etc. Compared with photodynamic therapy, sonodynamic therapy has the following advantages: 1) it can not only treat superficial tumors in the human body, but also treat tumors deep in any part of the human body, and the treatment of the tumors deep in the body is performed without the need of an endoscope, and the treatment is carried out with external ultrasound irradiation, which causes no pain to the patient; 2) it is not necessary for the patient to avoid light after treatment, and the treatment can be repeated at any time; and 3) it can effectively prevent the metastasis of malignant tumors and is an effective way to kill malignant tumors.

So far, the photosensitizer or sonosensitizer reported has disadvantages such as large differences in selectivity to tumor cells, short radiation wavelength, narrow therapeutic window, poor solubility under physiological conditions, slow clearance rates in the body, and difficulty in reflecting clinical value. In addition, when sonodynamic therapy is performed, as the treatment system has a simple structure and small size, it can only act on parts of the patient rather than providing comprehensive treatment to the patient, and cannot effectively kill micro malignant tumors that have developed in the human body but cannot be detected by the current medical equipment and instruments. Therefore, for patients whose malignant tumors have undergone systemic metastasis, or for patients whose malignant tumors are undergoing systemic metastasis after cancer surgery, the existing treatment system cannot provide timely and effective treatment for them. Since the existing ultrasound treatment systems are all single-head transducers, for lesions in different parts of the same patient, doctors cannot simultaneously treat the lesions and select ultrasound transducers according to the actual needs for treatment. Moreover, when a single-head ultrasound transducer is used to perform systemic treatment on patients, more than tens of hours of continuous work is required to finish the treatment, which greatly increases the workload of doctors, resulting in unbearable treatment time and missing the best treatment opportunity for patients. Therefore, it is desired for skilled persons in the medical profession that there is a device that can completely irradiate the human body, has energy exceeding the light energy, can reach the deep part of the human body, and excite the medicine to kill the tumor cells deep in the human body.

Therefore, there is an urgent need to develop a photoacoustic sensitizer with a longer absorption wavelength and good water solubility. Said photoacoustic sensitizer, as a sonosensitizer, can be combined with an ultrasound medical system to achieve comprehensive sonodynamic therapy on patients, so as to promote the development of photodynamic therapy and sonodynamic therapy.

SUMMARY OF THE INVENTION

In view of this, the present disclosure designs and synthesizes a chlorin derivative or a pharmaceutically acceptable salt thereof, and applying the same as a photoacoustic sensitizer to the treatment of tumors. In addition, the present disclosure also combines the photoacoustic sensitizer as sonosensitizer with an ultrasound medical system to perform a comprehensive sonodynamic therapy on patients. Particularly, according to the combination, the patient can first be asked to take the chlorin derivative or the pharmaceutically acceptable salt thereof of the present disclosure, and then the comprehensive sonodynamic therapy is performed on patients. During the process of the comprehensive sonodynamic therapy, the treatment parameters of ultrasonic transducer(s) used in different regions can be changed at any time according to the treatment needs of the parts of the patient's body and the patient's feelings, so that the ultrasonic medical system can achieve the optimal therapeutic effect.

According to a first aspect of the present disclosure, provided is a chlorin derivative or a pharmaceutically acceptable salt thereof having a structure represented by following formula (I):

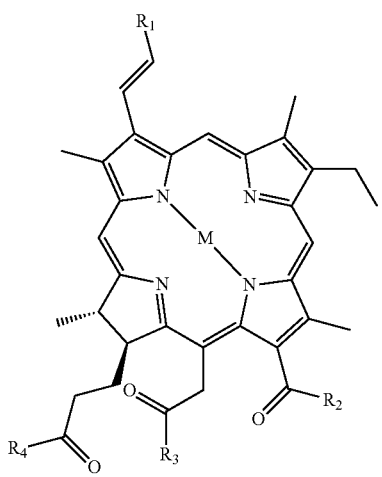
(I)

wherein,

R₁ is

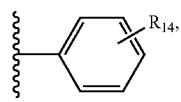

wherein R₁₄ is —H, C₁-C₆ alkoxy or C₁-C₄ haloalkyl; or

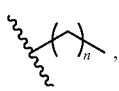

wherein n is any integer from 2 to 7;

R₂ is

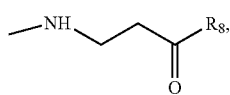

C₁-C₆ alkoxy, or —OH, wherein R₈ is any of the following groups:

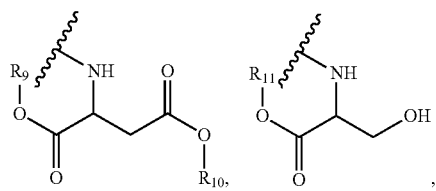

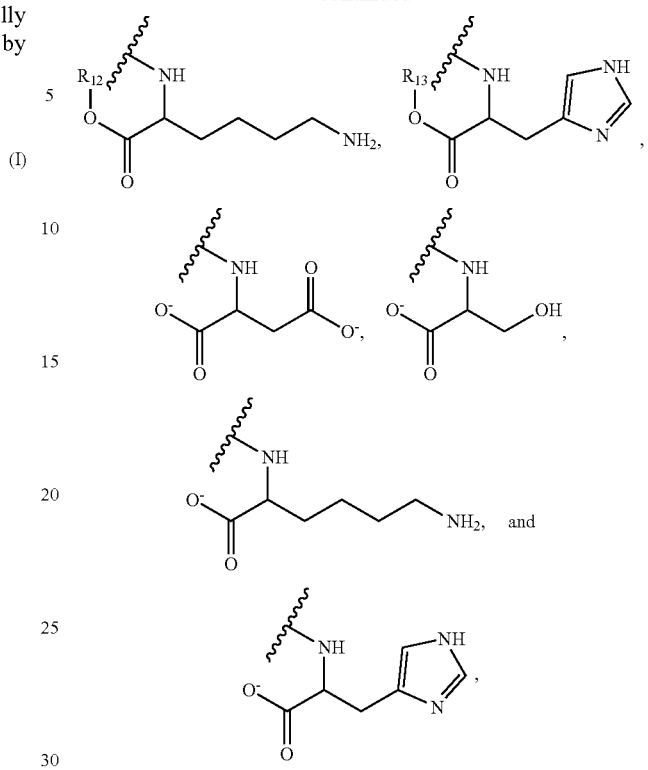

wherein R₉, R₁₀, R₁₁, R₁₂ and R₁₃ may be the same or different, and are each independently selected from 01-C₆ alkyl, and when R₂ is

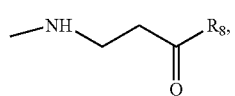

R₃ and R₄ are each independently selected from 01-C alkoxy or —OH;

when R₂ is C₁—C alkoxy or —OH, one of R₃ and R₄ is any of the following groups:

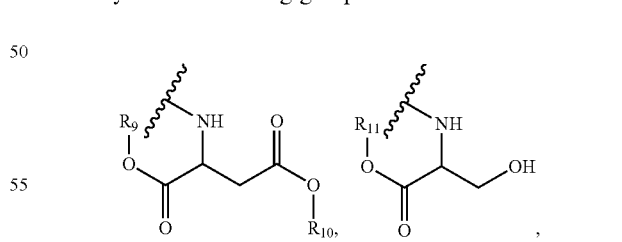

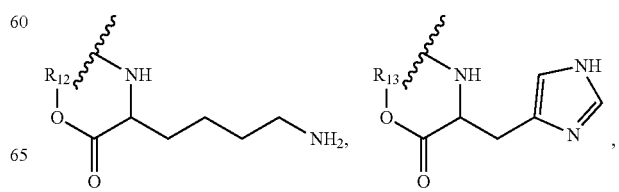

-continued

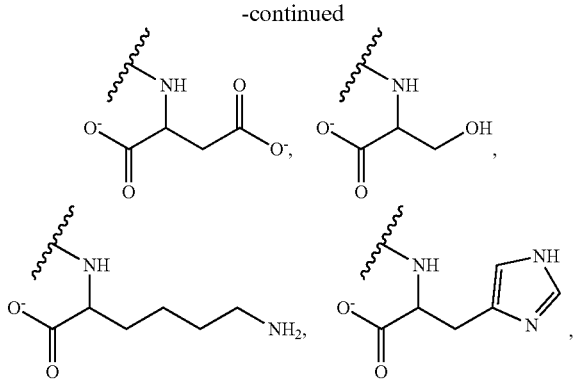

wherein $R_9$, $R_{10}$, $R_{11}$, $R_{12}$ and $R_{13}$ are defined as above, and the other of $R_3$ and $R_4$ is $C_1$—C alkoxy or —OH; and M is 2H or a metal ion, for example, a divalent metal ion such as $Cu^{2+}$, $Fe^{2+}$, $Zn^{2+}$, $Mg^{2+}$, $Ni^{2+}$, $Co^{2+}$, $Pt^{2+}$ or $Pd^{2+}$; or a tetravalent metal ion such as $Sn^{4+}$ or $Ti^{4+}$.

According to a second aspect of the present disclosure, provided is a method for preparing the chlorin derivative or the pharmaceutically acceptable salt thereof according to the first aspect of the present disclosure, wherein the method comprises the steps of:

$a_1$: subjecting compound 1, namely chlorin e6, to esterification reaction with an alcohol to obtain compound 2:

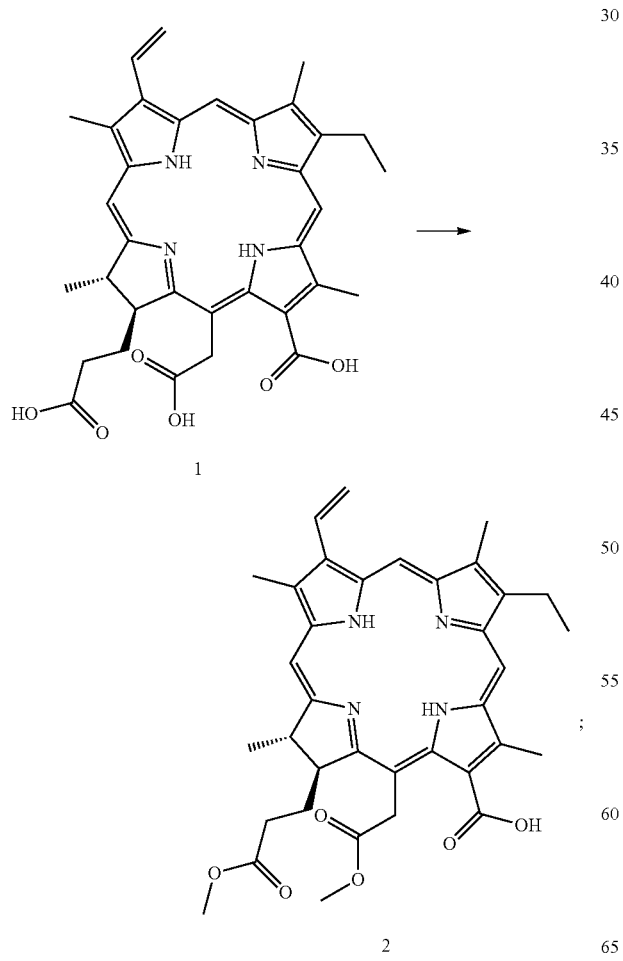

$b_1$: subjecting compound 2 to condensation reaction with β-alanine tert-butyl ester hydrochloride in the presence of a condensation agent to obtain compound 3:

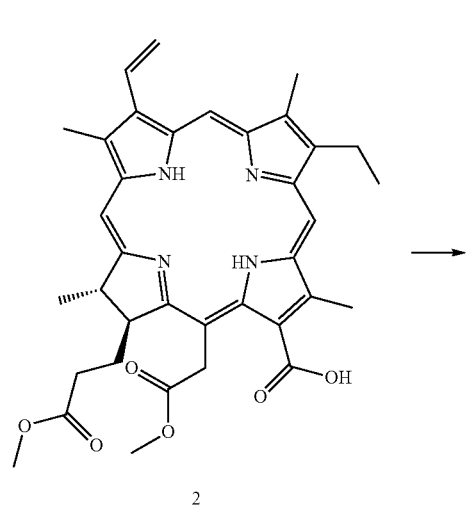

$c_1$: subjecting compound 3 to olefin metathesis reaction with a substituted α-olefin

in the presence of a catalyst to obtain compound 4:
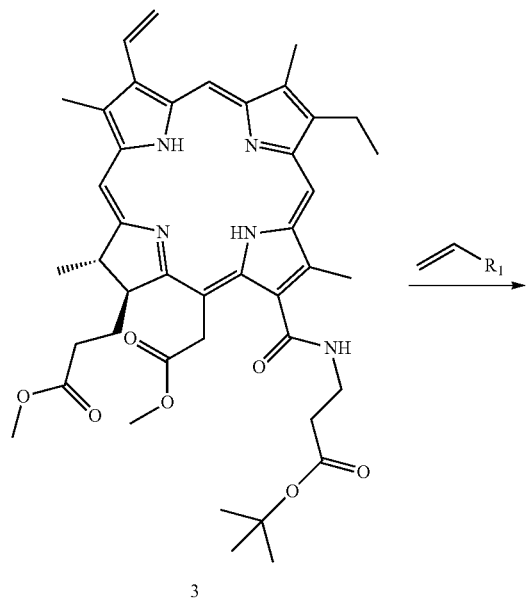
3
wherein $R_1$ is
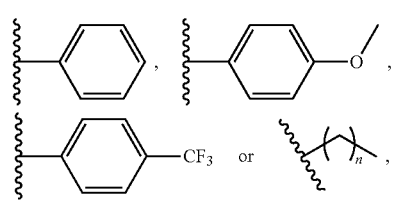
wherein n is any integer from 2 to 7;
$d_1$: subjecting compound 4 to hydrolysis reaction to obtain compound 5:
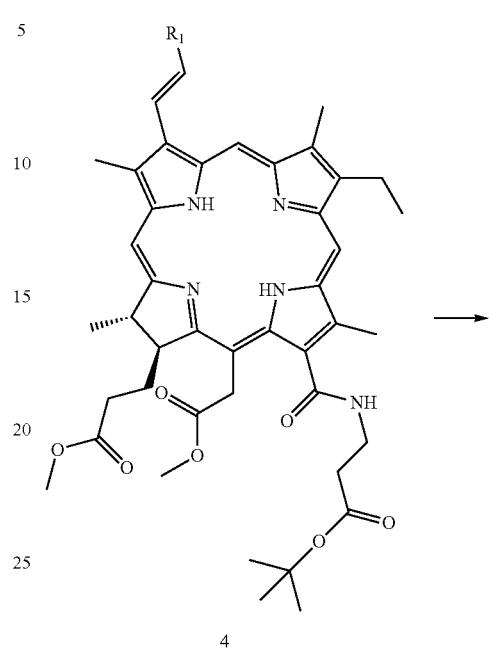
4
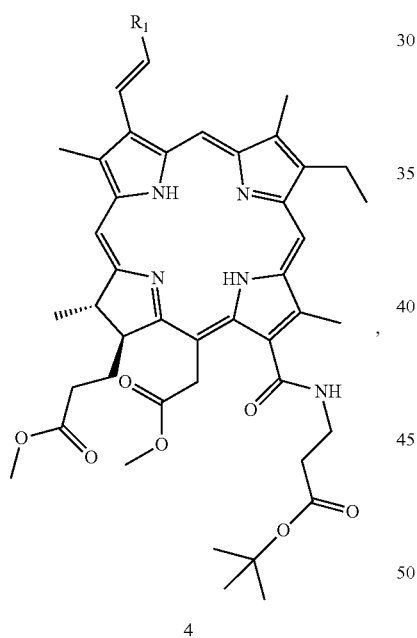
4
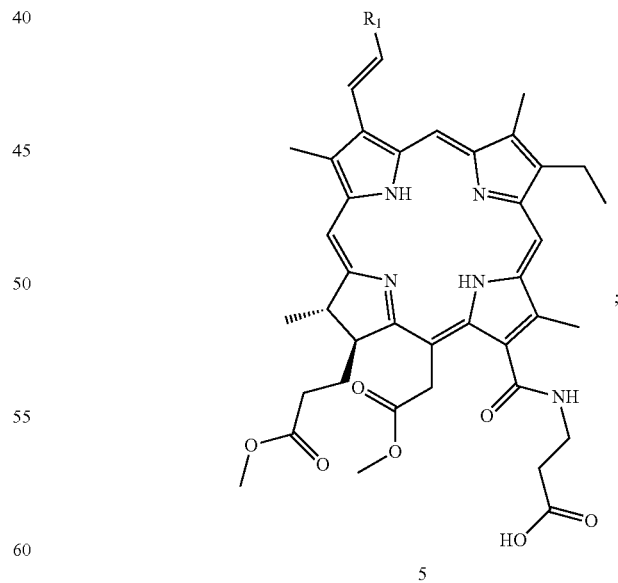
5
$e_1$: subjecting compound 5 to condensation reaction with an amino acid ester hydrochloride in the presence of a condensation agent to obtain a compound of formula II(a):

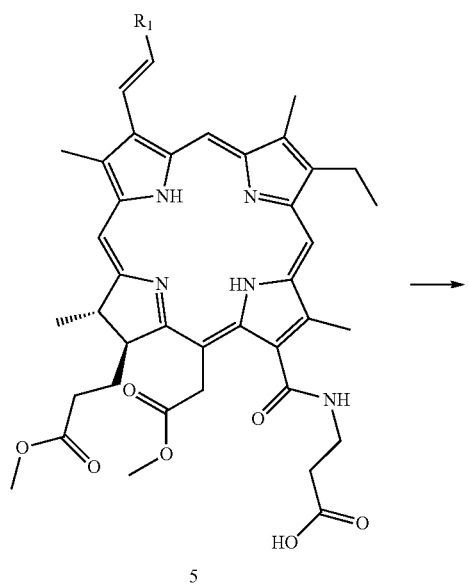

5

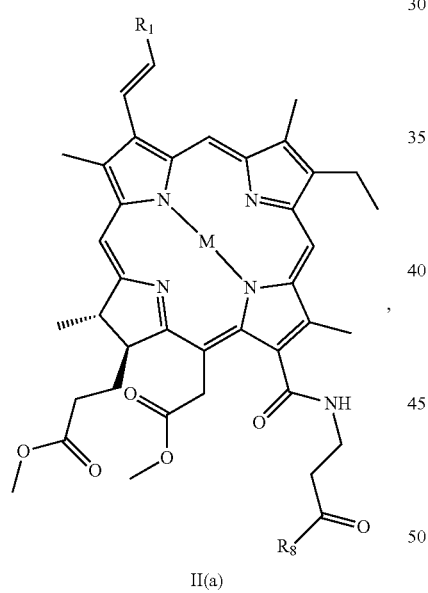

II(a)

wherein M is 2H, or will become a metal ion, for example, a divalent metal ion such as $Cu^{2+}$, $Fe^{2+}$, $Zn^{2+}$, $Mg^{2+}$, $Ni^{2+}$, $Co^{2+}$, $Pt^{2+}$ or $Pd^{2+}$, or a tetravalent metal ion such as $Sn^{4+}$ or $Ti^{4+}$ upon reaction with a metal chloride or acetate complex, and wherein $R_8$ is defined as in the first aspect of the present disclosure; and optionally subjecting the compound of formula II(a) to hydrolysis reaction under alkaline conditions to obtain a corresponding salt, that is, a compound of formula II(b); or alternatively, a$_2$: subjecting compound 1, namely chlorin e6, to reaction with an alkyl halide under alkaline conditions to obtain compound 10:

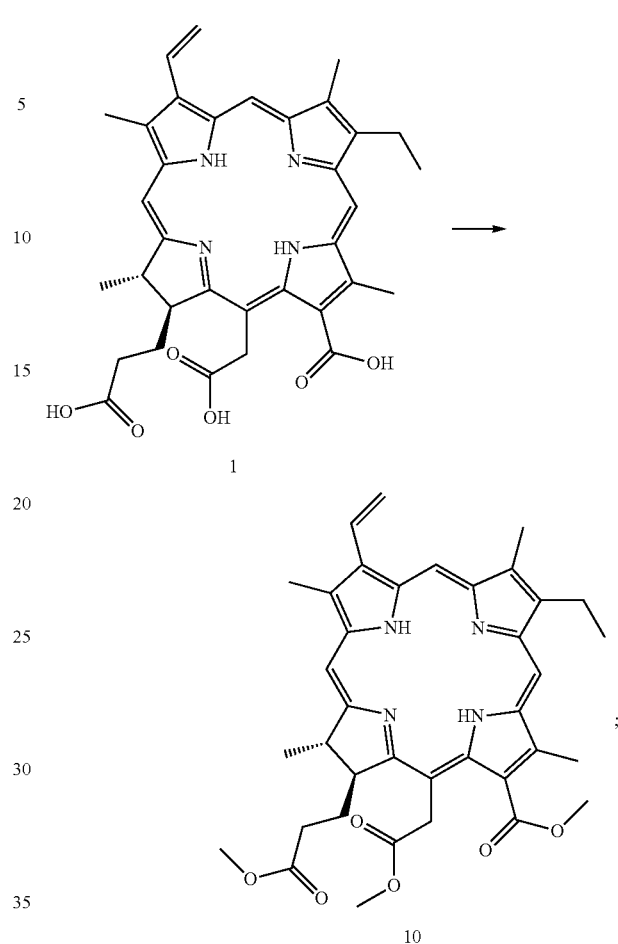

b2: subjecting compound 10 to olefin metathesis reaction with a substituted α-olefin $$\diagup\!\!\diagdown\!\!R_1$$

in the presence of a catalyst to obtain compound 11:

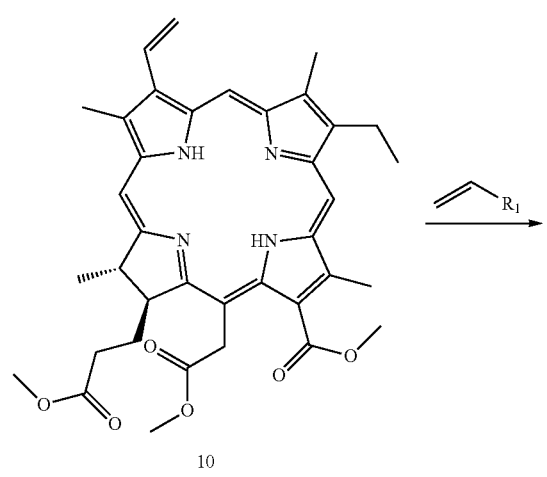

-continued

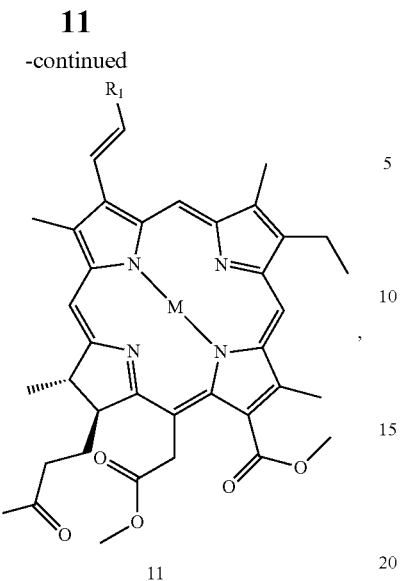

11 wherein R₁ is

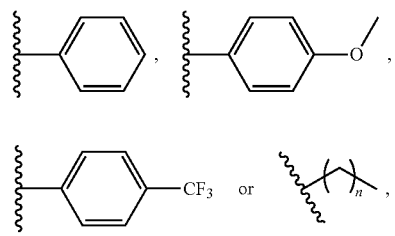

wherein n is any integer from 2 to 7;
wherein M is 2H, or will become a metal ion, for example, a divalent metal ion such as $Cu^{2+}$, $Fe^{2+}$, $Zn^{2+}$, $Mg^{2+}$, $Ni^{2+}$, $Co^{2+}$, $Pt^{2+}$ or $Pd^{2+}$, or a tetravalent metal ion such as $Sn^{4+}$ or $Ti^{4+}$ upon reaction with a metal chloride or acetate complex;

c2: subjecting compound 11 to hydrolysis reaction under alkaline conditions to obtain compound 13:

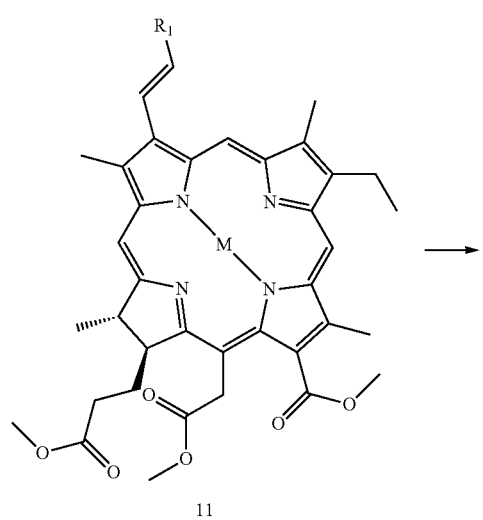

11

-continued

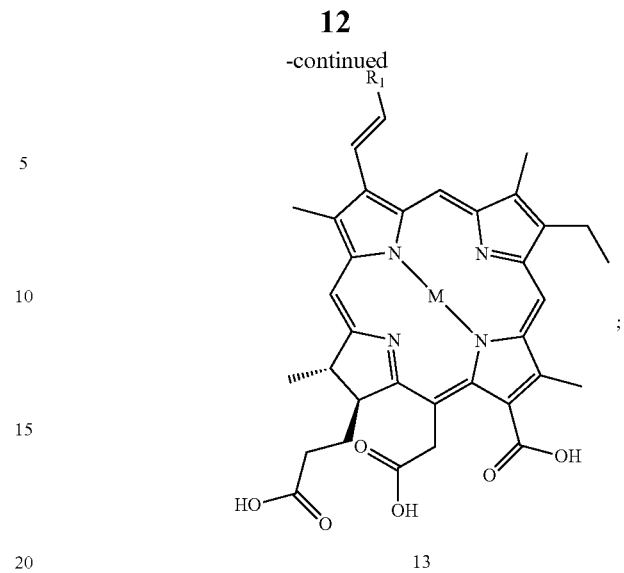

13 d₂: subjecting compound 13 to condensation reaction with an amino acid ester hydrochloride to obtain a compound of formula III(a):

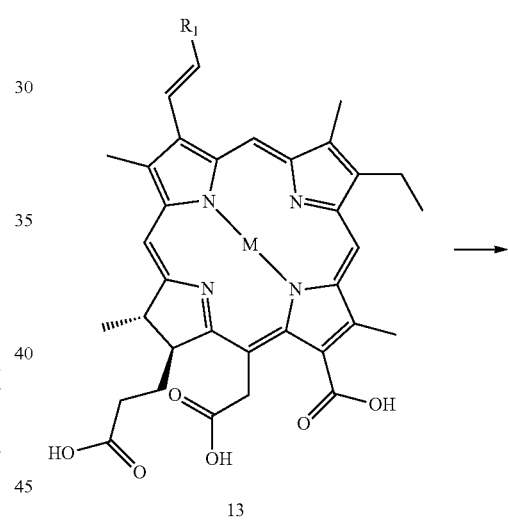

13

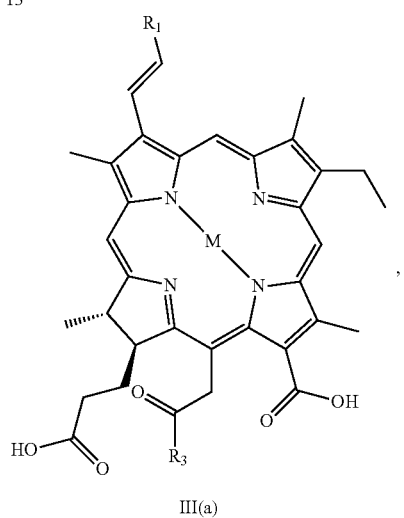

III(a)

wherein M is 2H, or will become a metal ion, for example, a divalent metal ion such as $Cu^{2+}$, $Fe^{2+}$, $Zn^{2+}$, $Mg^{2+}$, $Ni^{2+}$, $Co^{2+}$, $Pt^{2+}$ or $Pd^{2+}$, or a tetravalent metal ion such as $Sn^{4+}$ or $Ti^{4+}$ upon reaction with a metal chloride or acetate complex, wherein $R_3$ is defined as in the first aspect of the present disclosure; and optionally subjecting the compound of formula III(a) to hydrolysis reaction under alkaline conditions to obtain a corresponding salt, that is, a compound of formula III(b);

or alternatively, $a_3$: subjecting compound 19 to condensation reaction with an amino acid ester hydrochloride in the presence of a condensation agent to obtain compound 20:

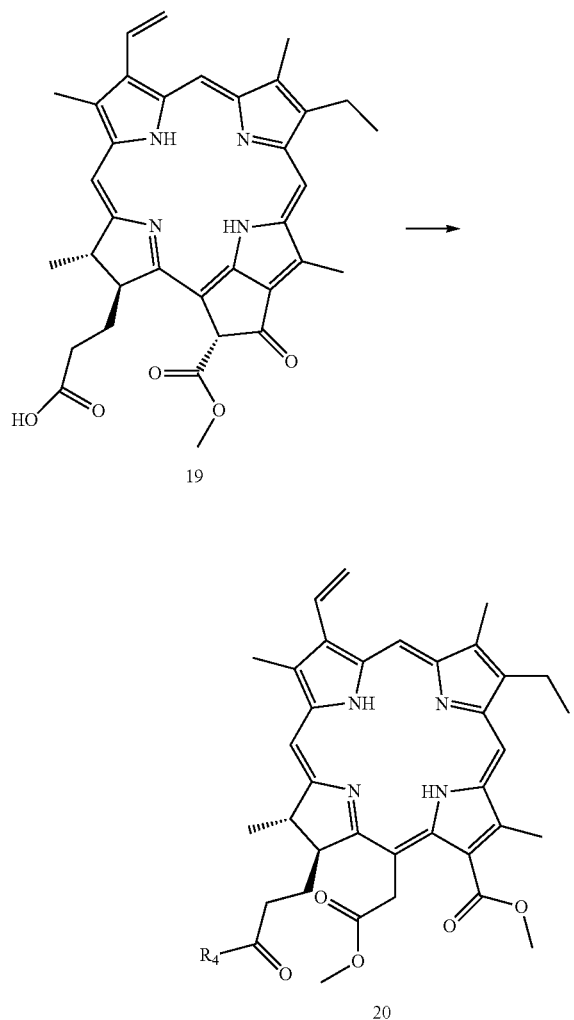

19

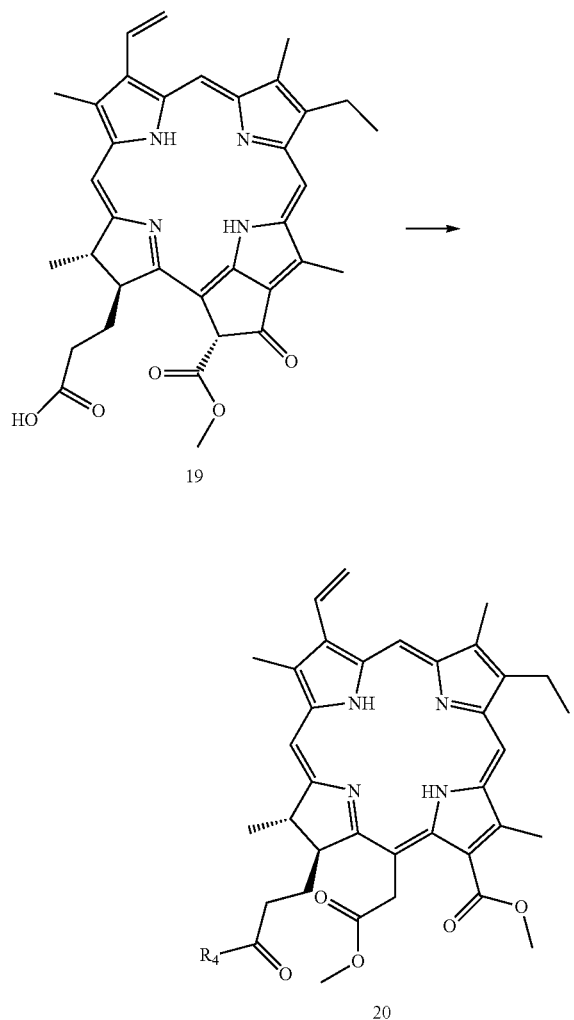

20

$b_3$: subjecting compound 20 to olefin metathesis reaction with a substituted α-olefin

in the presence of a catalyst to obtain a compound of formula IV(a):

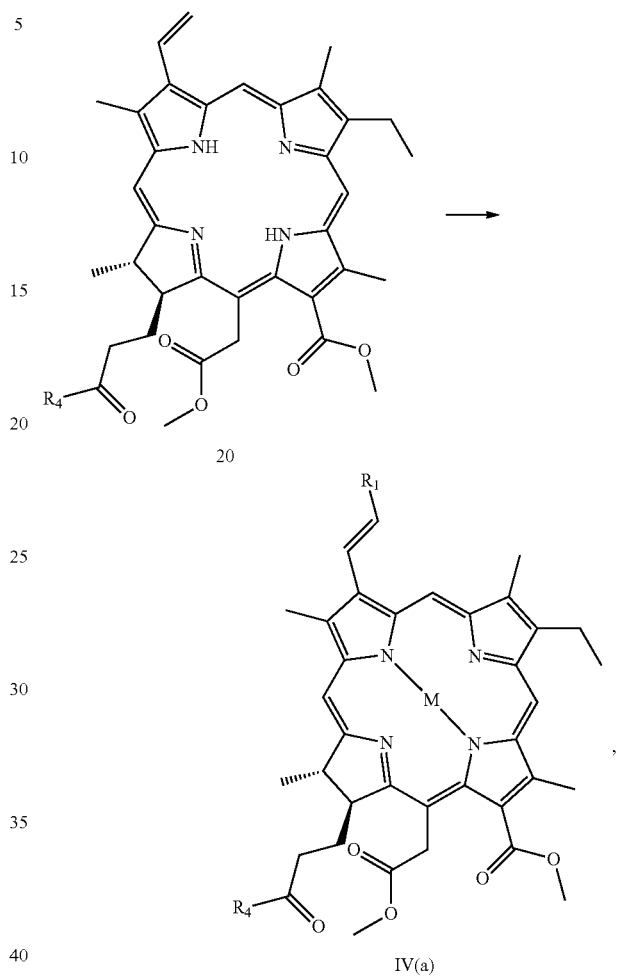

20

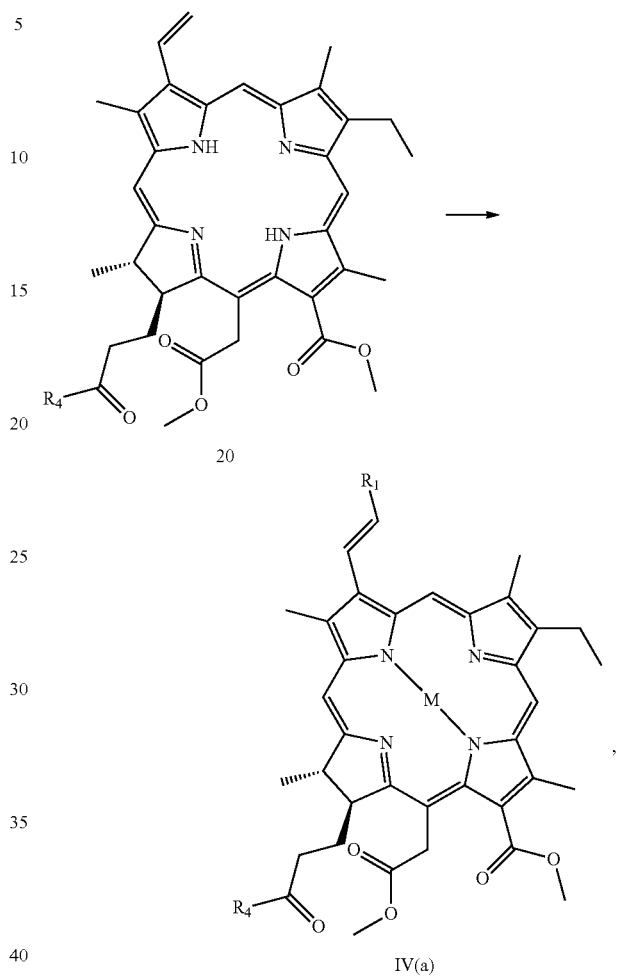

IV(a)

wherein $R_1$ is

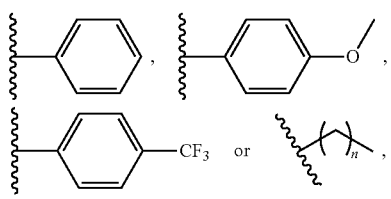

wherein n is any integer from 2 to 7, wherein M is 2H, or will become a metal ion, for example, a divalent metal ion such as $Cu^{2+}$, $Fe^{2+}$, $Zn^{2+}$, $Mg^{2+}$, $Ni^{2+}$, $Co^{2+}$, $Pt^{2+}$ or $Pd^{2+}$, or a tetravalent metal ion such as $Sn^{4+}$ or $Ti^{4+}$ upon reaction with a metal chloride or acetate complex, wherein $R_4$ is defined as in the first aspect of the present disclosure; and optionally subjecting the compound of formula IV(a) to hydrolysis reaction under alkaline conditions to obtain a corresponding salt, that is, a compound of formula IV(b).

According to a third aspect of the present disclosure, provided is an anti-tumor composition, wherein the anti-tumor composition comprises the chlorin derivative or the pharmaceutically acceptable salt thereof according to the first aspect of the present disclosure.

According to a fourth aspect of the present disclosure, provided is use of the chlorin derivative or the pharmaceutically acceptable salt thereof according to the first aspect of the present disclosure in the treatment of a tumor.

According to a fifth aspect of the present disclosure, provided is a combination of the chlorin derivative or the pharmaceutically acceptable salt thereof according to the first aspect of the present disclosure and an ultrasonic medical system, the ultrasonic medical system comprises a transducer ultrasonic bed and a contact agent, wherein the transducer ultrasonic bed comprises a bottom and a wall extending upward from the bottom; the bottom is provided, at positions corresponding to head, torso, and limbs of a subject, respectively, with at least one ultrasonic transducer for transmitting ultrasonic waves to the subject thereon; the wall is provided, at positions corresponding to the head and limbs of the subject, respectively, with at least one ultrasonic transducer for transmitting ultrasonic waves to the subject; and the contact agent is used to transmit ultrasonic waves between the subject and the ultrasonic transducers.

The present disclosure has the following advantageous technical effects:

The present disclosure provides a series of chlorin derivatives or pharmaceutically acceptable salts thereof by modifying chlorin e6, and uses the same as photoacoustic sensitizers for inhibition and treatment of tumors.

The chlorin derivatives and corresponding pharmaceutically acceptable salts according to the present disclosure, provided by modifying chlorin e6, retain the basic structure of chlorin e6 for use as a photoacoustic sensitizer, and have greatly improved water solubility. The chlorin derivatives or the pharmaceutically acceptable salts thereof provided by the present disclosure can be used for the treatment of tumors in a form of an injection.

In addition, the chlorin derivatives or the pharmaceutically acceptable salts thereof provided by the present disclosure exhibit a longer absorption wavelength, so that when being used as a photoacoustic sensitizer, they show improved tissues penetration, increased yield of reactive oxygen species, weakened dark toxicity, and enhanced therapeutic effect.

In addition, the chlorin derivatives or the pharmaceutically acceptable salts thereof provided by the present disclosure can generate a large amount of singlet oxygen under light irradiation, which allows an improved ability to kill tumor cells. Furthermore, when the chlorin derivatives or the pharmaceutically acceptable salts thereof are used as photoacoustic sensitizers, they can also reduce the volume and weight of tumors, inhibit the metastasis of primary tumors, and have good effects on inhibition and treatment of tumors.

The comprehensive ultrasound medical system provided by the present disclosure effectively solves the problem of death of patients with tumor, especially malignant tumor, caused by spread and metastasis of tumors. Ultrasound that can irradiate the human body in all directions can not only reach the tissues deep in the human body but also penetrate the human body. Energy of the ultrasounds can successfully excite the sonosensitizer, namely the chlorin derivatives or the pharmaceutically acceptable salts thereof, to kill tumors in various parts of the human body.

In addition, the working parameters of the ultrasonic transducer(s) can be flexibly selected during the sonodynamic therapy, thereby increasing the convenience in the process of the treatment by doctors and greatly shortening the treatment time for the patient. The present disclosure is performed with external ultrasound, has no damage to normal human tissues and kills malignant tumors without pain, and thus provides a new treatment system for malignant tumor with good selectivity and small side effects.

In addition, the chlorin derivatives and corresponding pharmaceutically acceptable salts provided by the present disclosure, when being used as sonosensitizers, can be used in combination with the above-mentioned comprehensive ultrasound medical system, and thereby effectively reduce the volume and weight of tumors, inhibit the metastasis of primary tumors, greatly improve the ability to kill tumor cells, and have a good effect on inhibition and treatment of tumors.

BRIEF DESCRIPTION OF THE FIGURES

In order to illustrate the embodiments of the present disclosure or the technical solutions in the prior art more clearly, the following will briefly describe the drawings used in the embodiments. Obviously, the drawings described below only refer to some embodiments of the present disclosure, and the ordinary skilled in the art can obtain other embodiments of the present disclosure based on these drawings, without creative work.

FIG. 24 shows lesion information generated by an ultrasound medical system according to the present disclosure.

DETAILED DESCRIPTION OF THE INVENTION

Figure 1:
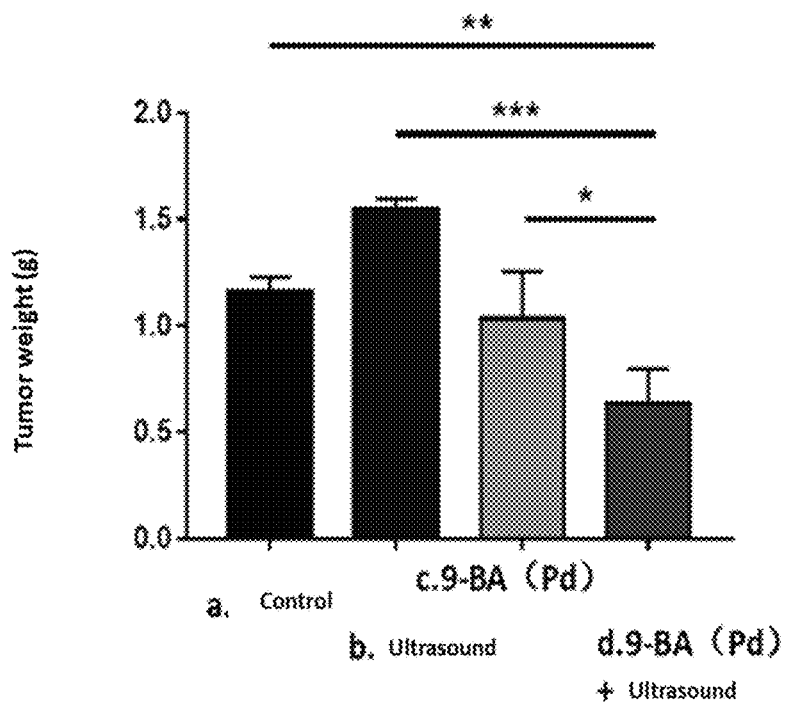
FIG. 1 is a bar graph showing the effect of compound 9-BA(Pd) according to the present disclosure and the ultrasonic treatment, alone or in combination, on the weight of tumor tissue in mice bearing primary breast cancer (*$P<0.01$~$0.001$).

The present disclosure will be clearly and completely described below by reference to the embodiments of the present disclosure and the accompanying drawings. Obviously, the described embodiments are only some of the embodiments of the present disclosure, and not all of them. Based on the embodiments of the present disclosure, all other embodiments available to the ordinary skilled in the art fall into the scope of the present disclosure.

The term "alkyl" as used in the present disclosure refers to a straight or branched chain alkyl with a specified number of carbon atoms. In the present disclosure, illustrative examples of "alkyl" include methyl, ethyl, n-propyl, isopropyl, n-butyl, isobutyl, tert-butyl, n-pentyl, n-hexyl, and the like.

The term "haloalkyl" as used in the present disclosure refers to a group formed by replacing one or more hydrogen atoms in an alkyl with halogen such as F, Cl, Br or I. Depending on the type of halogen atom, "haloalkyl" in the present disclosure comprises fluoroalkyl, chloroalkyl, bromoalkyl and iodoalkyl. Depending on the number of halogen atom, "haloalkyl" in the present disclosure comprises monohaloalkyl, dihaloalkyl, and polyhaloalkyl. In the present disclosure, illustrative examples of "haloalkyl" comprise monofluoromethyl, difluoromethyl, trifluoromethyl, trifluoroethyl, trifluoro-n-propyl, trifluoro-n-butyl, and the like.

The term "alkoxy" as used in the present disclosure refers to a group in which a straight or branched alkyl with a specified number of carbon atoms is linked to oxygen and further to other moiety/moieties of the molecule by the oxygen. Examples of "alkoxy" comprise methoxy, ethoxy, n-propoxy, isopropoxy, n-butoxy, isobutoxy, tert-butoxy, n-pentoxy or n-hexoxy, etc.

The term "substituted α-olefin" as used in the present disclosure refers to an olefin with a carbon-carbon double bond (—C=C—) at the terminal. In the present disclosure, examples of "substituted α-olefin" comprise propylene, 1-hexene, p-methoxystyrene, p-trifluoromethylstyrene, and the like.

In photoacoustic dynamic therapy, photoacoustic sensitizers play an important role as a bridge of reaction. In the field of photoacoustic dynamic therapy for tumors, chlorin e6 is a very important photoacoustic sensitizer, is one of the chlorophyll degradation derivatives, and has an ideal photoacoustic dynamic effect on tumors. As a photoacoustic sensitizer, chlorin e6 has many advantages such as high specific accumulation at the tumor site, fast absorption at the tumor site, fast clearance rate from the body, and low toxicity and side effects. However, chlorin e6 also has disadvantages such as poor water solubility and relatively low activity when being used as a photoacoustic sensitizer. The present disclosure improves the photoacoustic dynamic activity and water solubility of chlorin e6 by modifying some functional groups thereof.

Thus, according to a first aspect of the present disclosure, the present disclosure provides a chlorin derivative or a pharmaceutically acceptable salt thereof, having a structure represented by following formula (I):

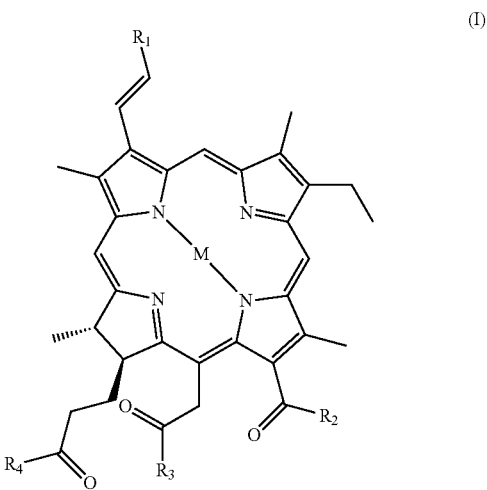

(I)

wherein
$R_1$ is

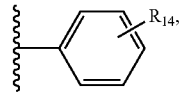

wherein $R_{14}$ is —H, $C_1$-$C_6$ alkoxy or $C_1$-$C_4$ haloalkyl; or

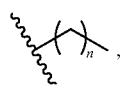

wherein n is any integer from 2 to 7;

$R_2$ is

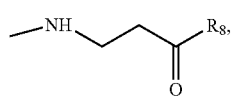

$C_1$-$C_6$ alkoxy or —OH, wherein Ra is any of the following groups:

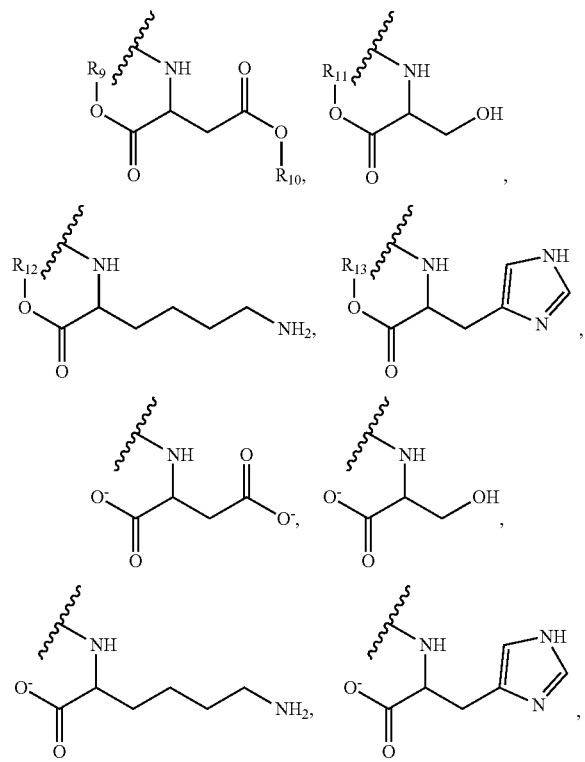

wherein $R_9$, $R_{10}$, $R_{11}$, $R_{12}$ and $R_{13}$ may be the same or different, and are each independently selected from $C_1$-$C_6$ alkyl, and when $R_2$ is

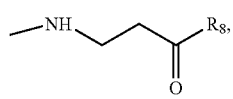

$R_3$ and $R_4$ are each independently selected from $C_1$-$C_6$ alkoxy or —OH;

when $R_2$ is $C_1$-$C_6$ alkoxy or —OH, one of $R_3$ and $R_4$ is any of the following groups:

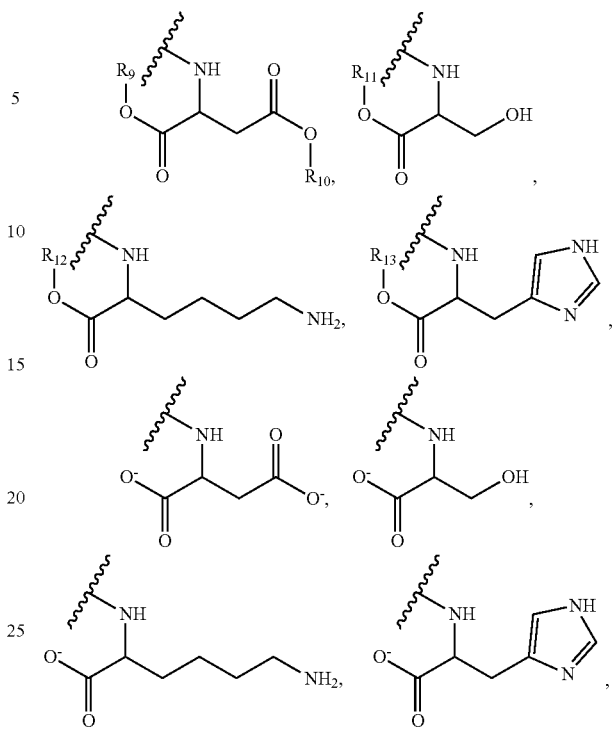

wherein $R_9$, $R_{10}$, $R_{11}$, $R_{12}$ and $R_{13}$ are defined as above, and the other of $R_3$ and $R_4$ is $C_1$-$C_6$ alkoxy or —OH; and M is 2H or a metal ion, for example, a divalent metal ion such as $Cu^{2+}$, $Fe^{2+}$, $Zn^{2+}$, $Mg^{2+}$, $Ni^{2+}$, $Co^{2+}$, $Pt^{2+}$ or $Pd^{2+}$; or a tetravalent metal ion such as $Sn^{4+}$ or $Ti^{4+}$.

In the present disclosure,

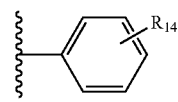

means that $R_{14}$ may be a substituent at any position, such as ortho-, meta- or para-position, of phenyl. Preferably, $R_{14}$ is a substituent at para-position.

In the present disclosure, $C_1$-$C_6$ alkoxy group refers to a group obtained by linking a straight or branched alkyl with 1 to 6 carbon atoms to oxygen atom. Therefore, in the structure represented by formula (I), when $R_{14}$, $R_2$, $R_3$, and $R_4$ are $C_1$-$C_6$ alkoxy, they can be, for example, methoxy, ethoxy, n-propoxy, isopropoxy, n-butoxy, isobutoxy, tert-butoxy, n-pentoxy, or n-hexoxy, and the like. Preferably, $R_{14}$, $R_2$, $R_3$, and $R_4$ are methoxy (—$OCH_3$).

In the present disclosure, $C_1$-$C_4$ haloalkyl refers to a group obtained by substituting one or more hydrogen atoms of a straight or branched alkyl with 1 to 4 carbon atoms with halogen such as F, Cl, Br, or I. Thus, in the structure represented by formula (I), when $R_{14}$ is a $C_1$-$C_4$ haloalkyl, it can be, for example, monofluoromethyl, difluoromethyl, trifluoromethyl, trifluoroethyl, trifluoro-n-propyl, trifluoro-n-butyl and the like. Preferably, $R_{14}$ is trifluoromethyl (—$CF_3$).

In the present disclosure,

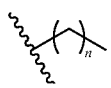

refers to a straight chain alkyl with n carbon atoms, where n is any integer from 2 to 7, for example, 2, 3, 4, 5, 6 or 7. Therefore, in the structure represented by formula (I), when $R_{14}$ is

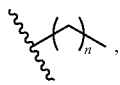

it can be, for example, ethyl, n-propyl, n-butyl, n-pentyl, n-hexyl, or n-heptyl. Preferably, $R_{14}$ is n-butyl.

In the present disclosure, the pharmaceutically acceptable salt of the chlorin derivative is a sodium or potassium salt of carboxylate in the chlorin derivative, or any other suitable form of pharmaceutically acceptable salt.

In an embodiment, the chlorin derivative or the pharmaceutically acceptable salt thereof is:

(IIa)

(IIb)

(IIIa)

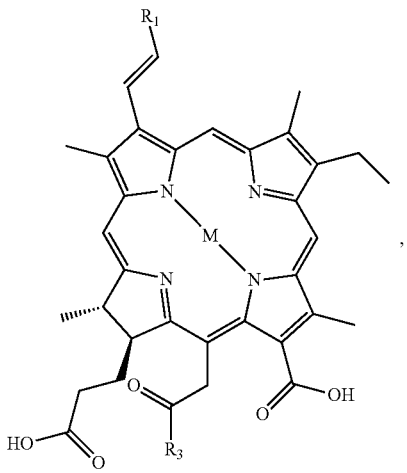

(IIIb)

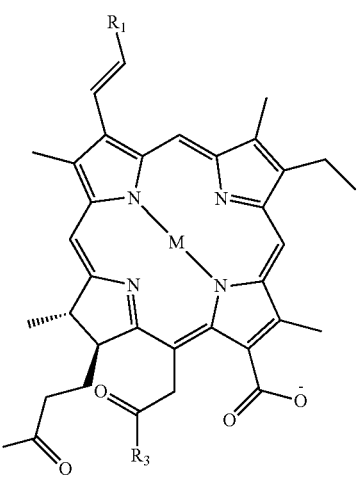

(IVa)

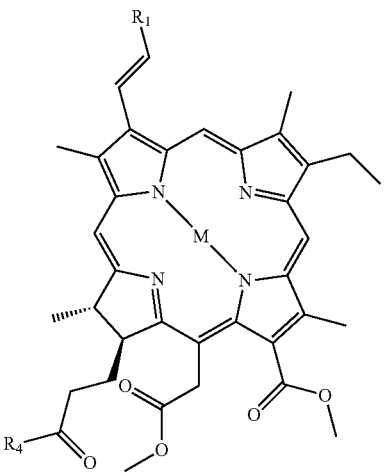

or

-continued
(IVb)
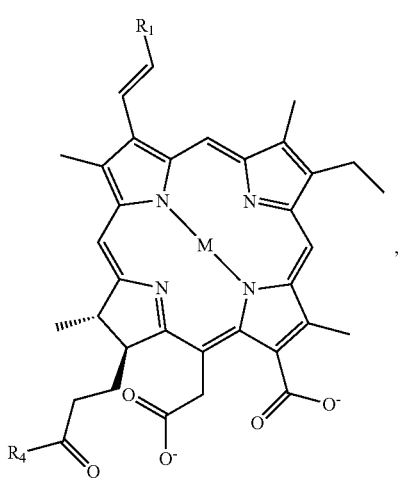
wherein,
R₁ is
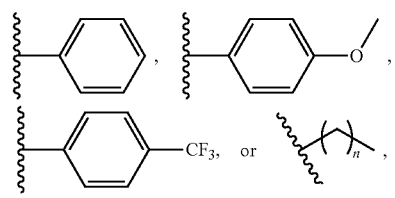
wherein n is any integer from 2 to 7,
R₃, R₄, and R₈ are any one of the following groups:
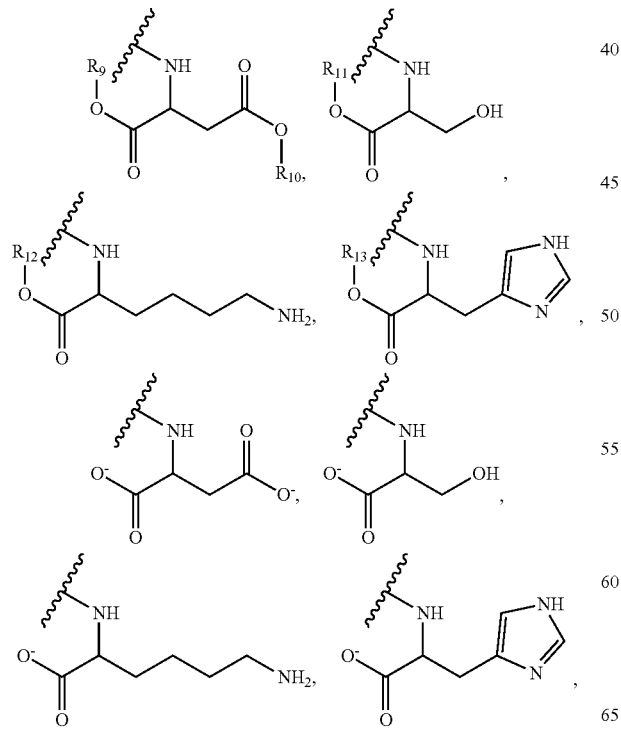
wherein R₉, R₁₀, R₁₁, R₁₂ and R₁₃ are defined as above, and
M is defined as above.
In an embodiment, the chlorin derivative or the pharmaceutically acceptable salt thereof is:
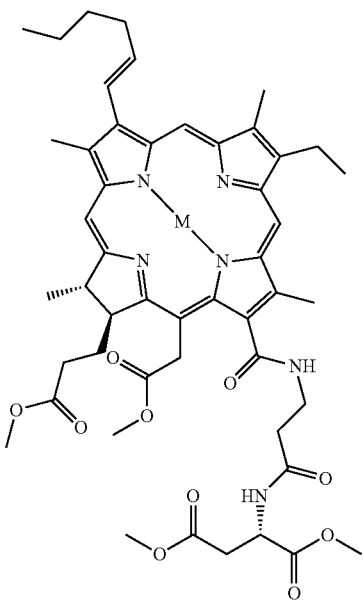
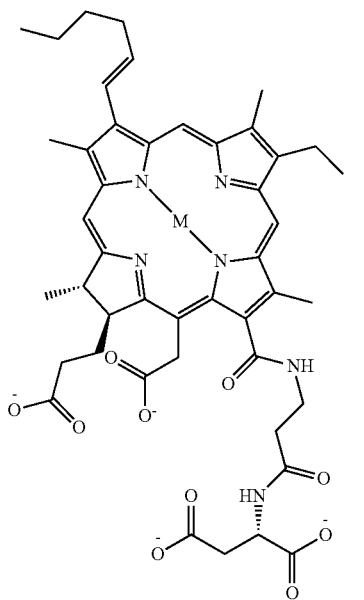

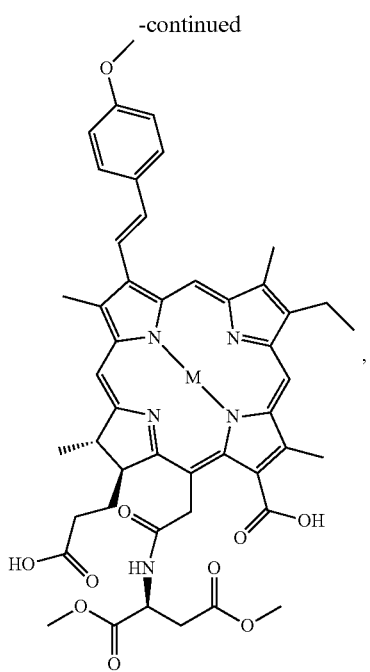

,

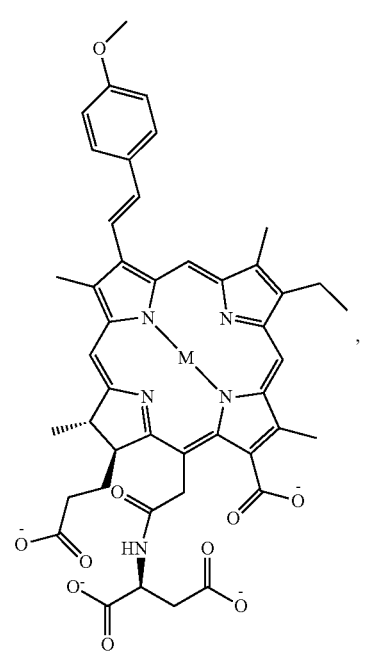

,

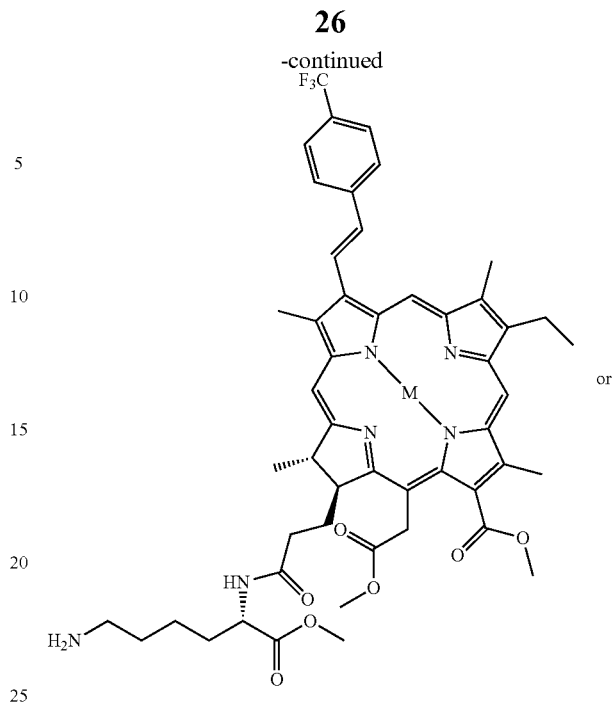

wherein M is defined as above.

According to a second aspect of the present disclosure, the present disclosure provides a method for preparing the chlorin derivative or the pharmaceutically acceptable salt thereof according to the first aspect of the present disclosure, wherein the method comprises the steps of:

a₁: subjecting compound 1, namely chlorin e6, to esterification reaction with an alcohol to obtain compound 2:

27
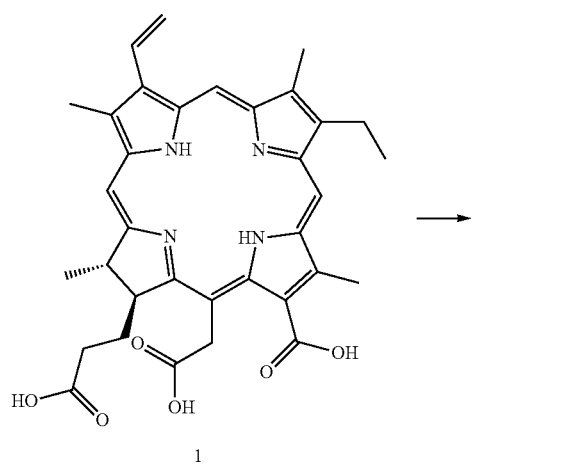
1
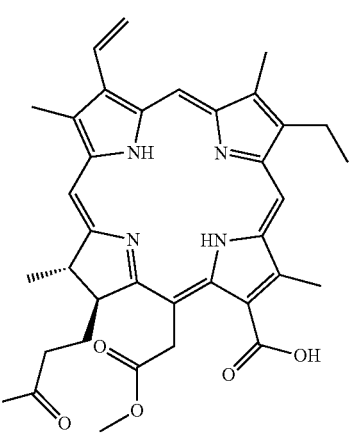
2
b₁: subjecting compound 2 to condensation reaction with β-alanine tert-butyl ester hydrochloride (H-β-Ala-OtBu·HCl) in the presence of a condensation agent to obtain compound 3:
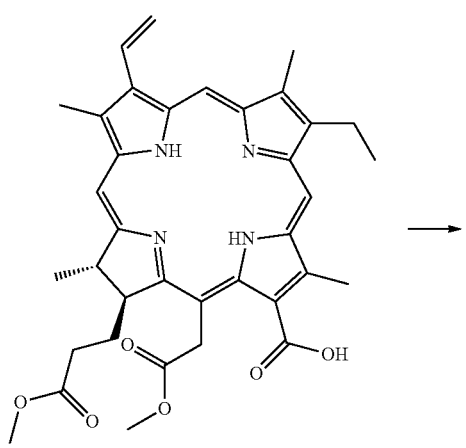
2
28
-continued
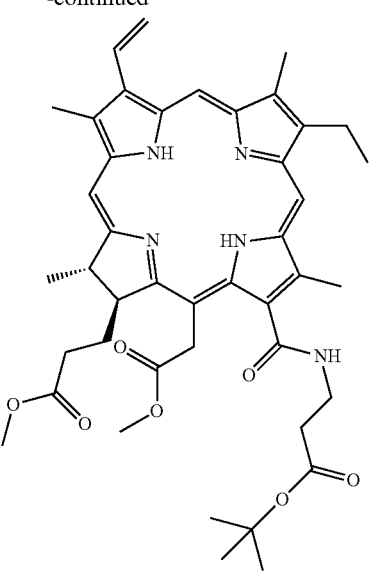
3
c₁: subjecting compound 3 to olefin metathesis reaction with a substituted α-olefin
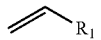
in the presence of a catalyst to obtain compound 4:
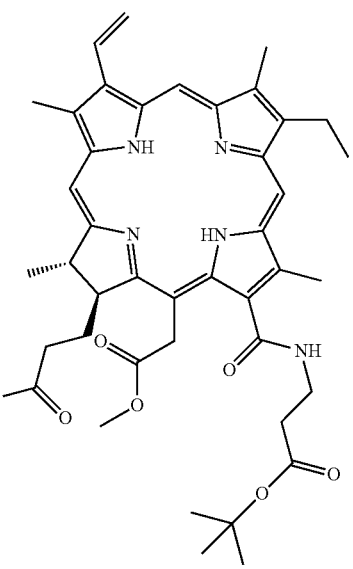 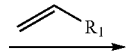
3

-continued
29
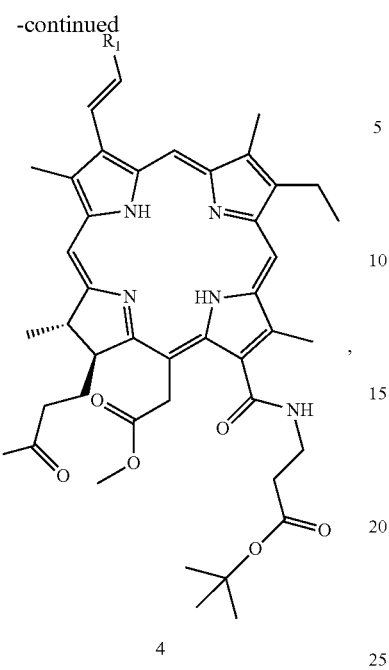
4
wherein $R_1$ is
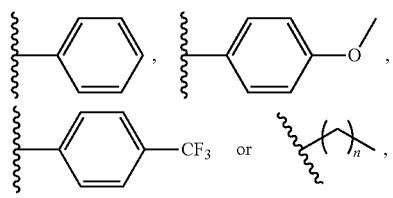
wherein n is any integer from 2 to 7;
$d_1$: subjecting compound 4 to hydrolysis reaction to obtain compound 5:
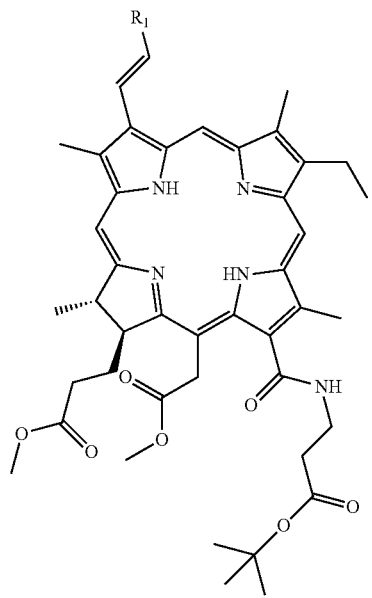
4
-continued
30
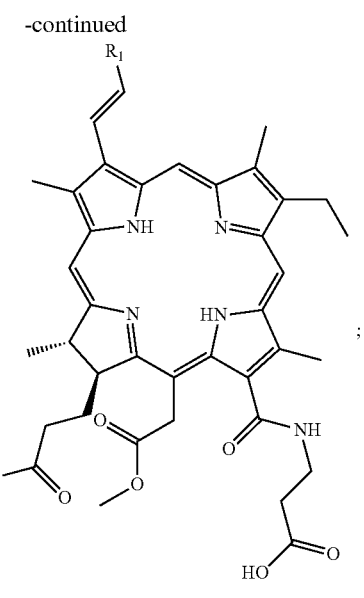
5
$e_1$: subjecting compound 5 to condensation reaction with an amino acid ester hydrochloride in the presence of a condensation agent to obtain a compound of formula II(a):
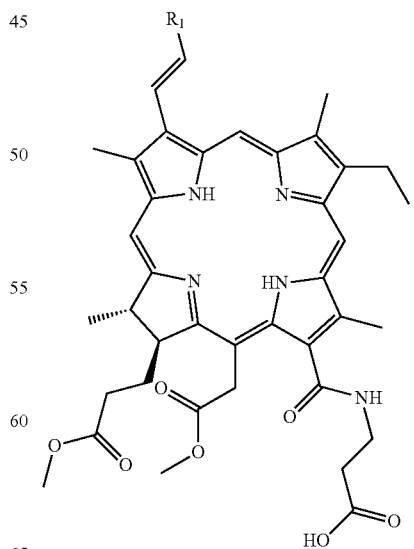
5

-continued

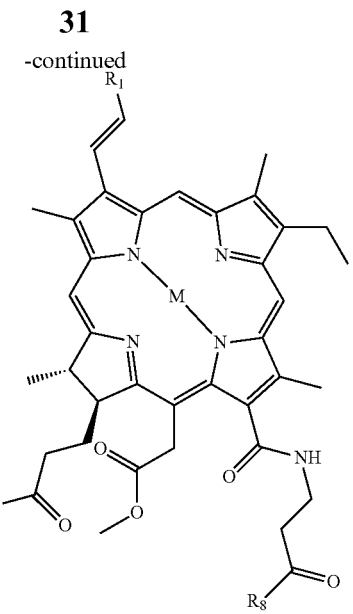

II(a)

wherein M is 2H, or will become a metal ion, for example, a divalent metal ion such as $Cu^{2+}$, $Fe^{2+}$, $Zn^{2+}$, $Mg^{2+}$, $Ni^{2+}$, $Co^{2+}$, $Pt^{2+}$ or $Pd^{2+}$, or a tetravalent metal ion such as $Sn^{4+}$ or $Ti^{4+}$ upon reaction with a metal chloride or acetate complex, and wherein $R_8$ is defined as above;

optionally subjecting the compound of formula II(a) to hydrolysis reaction under alkaline conditions to obtain a corresponding salt, that is, the compound of formula II(b);

or alternatively, $a_2$: subjecting compound 1, namely chlorin e6, to reaction with an alkyl halide under alkaline conditions to obtain compound 10:

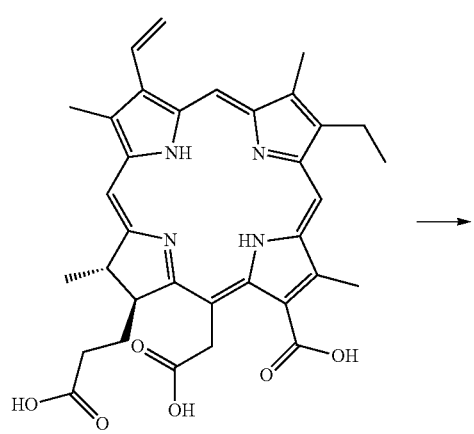

1

-continued

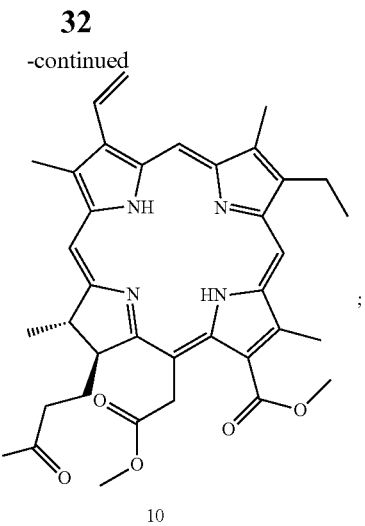

10

$b_2$: subjecting compound 10 to olefin metathesis reaction with a substituted α-olefin

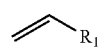

in the presence of a catalyst to obtain compound 11:

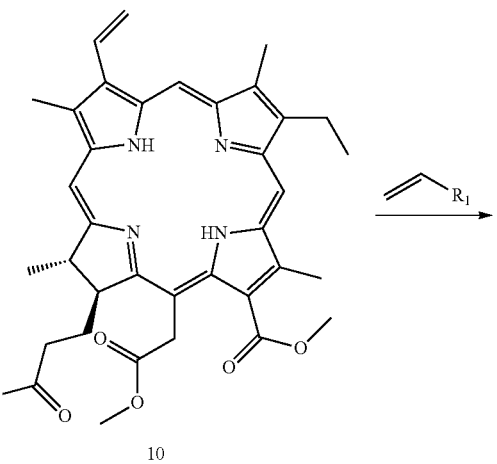

10

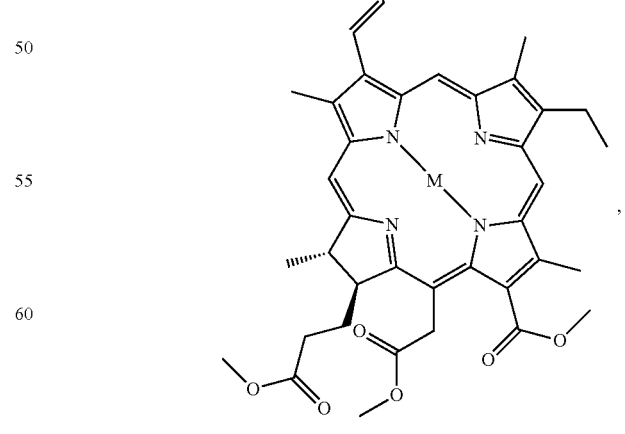

11 wherein $R_1$ is

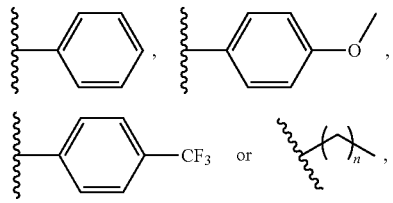

wherein n is any integer from 2 to 7;

wherein M is 2H, or will become a metal ion, for example, a divalent metal ion such as $Cu^{2+}$, $Fe^{2+}$, $Zn^{2+}$, $Mg^{2+}$, $Ni^{2+}$, $Co^{2+}$, $Pt^{2+}$ or $Pd^{2+}$, or a tetravalent metal ion such as $Sn^{4+}$ or $Ti^{4+}$ upon reaction with a metal chloride or acetate complex;

$c_2$: subjecting compound 11 to hydrolysis reaction under alkaline conditions to obtain compound 13:

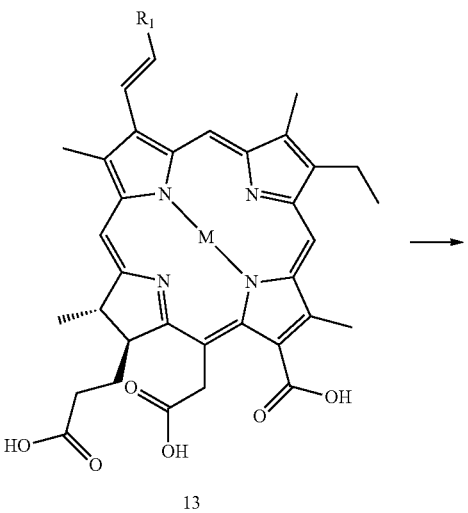

13

$d_2$: subjecting compound 13 to condensation reaction with an amino acid ester hydrochloride to obtain the compound of formula III(a):

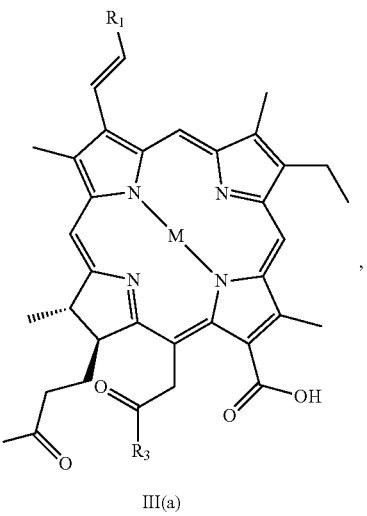

III(a)

wherein M is 2H, or will become a metal ion, for example, a divalent metal ion such as $Cu^{2+}$, $Fe^{2+}$, $Zn^{2+}$, $Mg^{2+}$, $Ni^{2+}$, $Co^{2+}$, $Pt^{2+}$ or $Pd^{2+}$, or a tetravalent metal ion such as $Sn^{4+}$ or $Ti^{4+}$ upon reaction with a metal chloride or acetate complex, and wherein $R_3$ is defined as above;

optionally subjecting the compound of formula III(a) to hydrolysis reaction under alkaline conditions to obtain a corresponding salt, that is, the compound of formula III(b);

or alternatively, $a_3$: subjecting compound 19 to condensation reaction with an amino acid ester hydrochloride in the presence of a condensation agent to obtain compound 20:

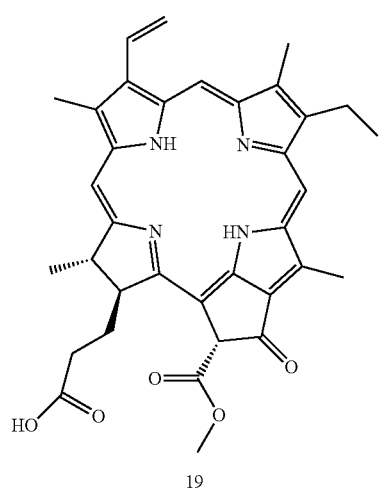

19

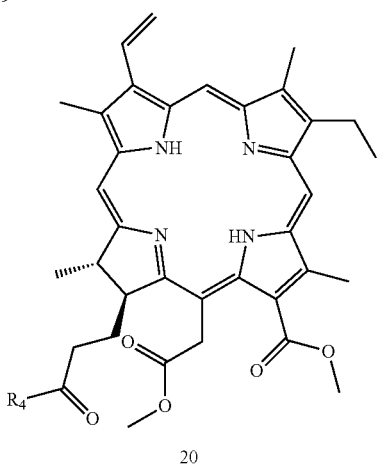

20 b₃: subjecting compound 20 to olefin metathesis reaction with a substituted α-olefin

in the presence of a catalyst to obtain the compound of formula IV(a):

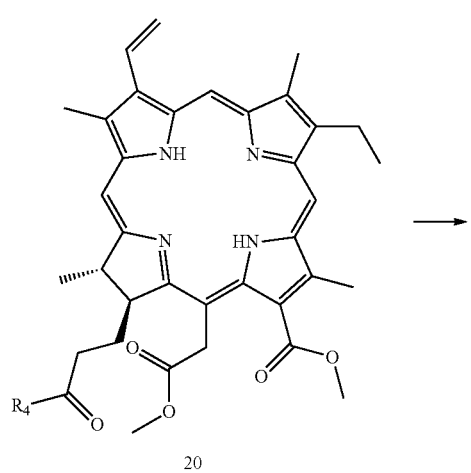

20

-continued

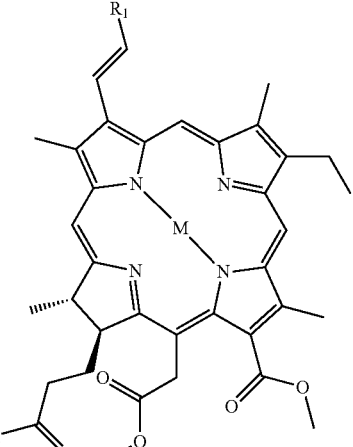

IV(a)

wherein $R_1$ is

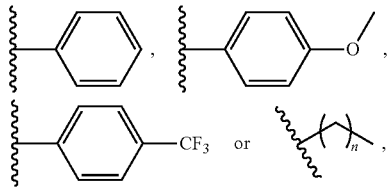

wherein n is any integer from 2 to 7,
wherein M is 2H, or will become a metal ion, for example, a divalent metal ion such as $Cu^{2+}$, $Fe^{2+}$, $Zn^{2+}$, $Mg^{2+}$, $Ni^{2+}$, $Co^{2+}$, $Pt^{2+}$ or $Pd^{2+}$, or a tetravalent metal ion such as $Sn^{4+}$ or $Ti^{4+}$ upon reaction with a metal chloride or acetate complex, and wherein $R_4$ is defined as above;
optionally subjecting the compound of formula IV(a) to hydrolysis reaction under alkaline conditions to obtain a corresponding salt, that is, the compound of formula IV(b).

According to a preferred embodiment of the present disclosure, in step $a_1$ of the method for preparing a chlorin derivative or a pharmaceutically acceptable salt thereof, chlorin e6 undergoes esterification reaction with methanol in 5% sulfuric acid/methanol (MeOH) solution to obtain compound 2.

According to a preferred embodiment of the present disclosure, in step $b_1$ of the method for preparing a chlorin derivative or a pharmaceutically acceptable salt thereof, the reaction solvent is dimethylformamide (DMF), and the condensation agent is o-benzotriazol-1-yl-N,N,N',N'-tetramethyluronium hexafluorophosphate (HBTU), or N,N-diisopropylethylamine (DIEA). In a further preferred embodiment, the molar ratio of compound 2 to HBTU, DIEA and β-alanine tert-butyl ester hydrochloride is 1:1-2:2-5:2-3.

According to a preferred embodiment of the present disclosure, in step $c_1$ of the method for preparing a chlorin derivative or a pharmaceutically acceptable salt thereof, the catalyst is Grubbs' catalyst, and the reaction solvent is dichloromethane (DCM). In a further preferred embodiment, the molar ratio of compound 3 to the substituted α-olefin is 1:10-30.

According to a preferred embodiment of the present disclosure, in step $d_1$ of the method for preparing a chlorin derivative or a pharmaceutically acceptable salt thereof, hydrolysis reaction occurs in dichloromethane (DCM) solution containing trifluoroacetic acid (TFA). In a further preferred embodiment, the solution has a volume fraction of 20%-30%. In a further preferred embodiment, the solution has a volume fraction of 25%.

According to a preferred embodiment of the present disclosure, in step $e_1$ of the method for preparing a chlorin derivative or a pharmaceutically acceptable salt thereof, the amino acid ester hydrochloride is an amino acid methyl ester hydrochloride, the reaction solvent is DMF, and the condensation agent is HBTU or DIEA. In a further preferred embodiment, the amino acid methyl ester hydrochloride may be aspartic acid methyl ester hydrochloride, serine methyl ester hydrochloride, lysine methyl ester hydrochloride or histidine methyl ester hydrochloride. In a further preferred embodiment, compound 5 is dissolved in DMF, then added with HBTU and DIEA, and stirred for reaction. Then, the amino acid methyl ester hydrochloride and DIEA are added for further reaction to obtain compound 6. In a further preferred embodiment, the molar ratio of compound 5 to HBTU, DIEA, and amino acid ester hydrochloride is 1: 1-2:2-5: 2-3.

According to a preferred embodiment of the present disclosure, in step $a_2$ of the method for preparing a chlorin derivative or a pharmaceutically acceptable salt thereof, chlorin is dissolved in DMF, and added with methyl iodide and anhydrous potassium carbonate for reaction to obtain compound 10. In a further preferred embodiment, the molar ratio of chlorin to alkyl halide, and anhydrous potassium carbonate is 1: 2-10:2-10.

According to a preferred embodiment of the present disclosure, in step $b_2$ of the method for preparing a chlorin derivative or a pharmaceutically acceptable salt thereof, the catalyst is Grubbs' catalyst, and the reaction solvent is DCM. In a further preferred embodiment, the molar ratio of compound 10 to substituted α-olefin is 1:10-30.

According to a preferred embodiment of the present disclosure, in step $c_2$ of the method for preparing a chlorin derivative or a pharmaceutically acceptable salt thereof, the reaction solution is tetrahydrofuran and a KOH aqueous solution. In a further preferred embodiment, the concentration of the KOH aqueous solution is 1 M. In a further preferred embodiment, the volume ratio of tetrahydrofuran to 1 M KOH aqueous solution is 1:1.

According to a preferred embodiment of the present disclosure, in step $d_2$ of the method for preparing a chlorin derivative or a pharmaceutically acceptable salt thereof, the amino acid ester hydrochloride is an amino acid methyl ester hydrochloride, the reaction solvent is DMF, and the condensation agent is 1-ethyl-3(3-dimethylpropylamine) carbodiimide (EDCI) or DIEA. In a further preferred embodiment, the molar ratio of compound 13 to EDCI, amino acid ester hydrochloride, and DIEA is 1:1-2:1-2:0.1-0.5.

According to a preferred embodiment of the present disclosure, in step $a_3$ of the method for preparing a chlorin derivative or a pharmaceutically acceptable salt thereof, the amino acid ester hydrochloride is an amino acid methyl ester hydrochloride, the reaction solvent is DMF, and the condensation agent is HBTU, or DIEA. In a further preferred embodiment, compound 19 is dissolved in DMF, then added with HBTU and DIEA, and stirred for reaction. Then, amino acid methyl ester hydrochloride and DIEA are added for further reaction to obtain compound 20. In a further preferred embodiment, the molar ratio of compound 19 to HBTU, DIEA, and amino acid ester hydrochloride is 1: 1-2:2-5: 2-3.

According to a preferred embodiment of the present disclosure, in step $b_3$ of the method for preparing a chlorin derivative or a pharmaceutically acceptable salt thereof, the catalyst is Grubbs' Catalyst, and the reaction solvent is DCM. In a further preferred embodiment, the molar ratio of compound 20 to substituted α-olefin is 1:10-30.

In an optional embodiment, the compound of formula II(a), formula II(b), formula III(a), formula III(b), formula IV(a) or formula IV(b) in which M is a metal ion can be obtained by reacting a corresponding compound in which M is 2H with a metal chloride or acetate complex.

In another optional embodiment, under alkaline conditions, the compound of formula II(a), formula III(a), or formula IV(a) may undergo hydrolysis reaction to obtain a corresponding salt, namely, the compound of formula II (b), formula III(b), or formula IV(b).

As mentioned above, the salt may be a sodium or potassium salt, or any other suitable form of pharmaceutically acceptable salt.

Of course, other solvents, solutions, condensation agents, catalysts, etc., that are well known in the art and can realize the above reactions, can also be used in the steps of the above preparation methods, and are not further defined by the present disclosure.

In a particular embodiment, the method for preparing the chlorin derivative or the pharmaceutically acceptable salt thereof comprises the following steps:

$a_1$: Homemade compound 1, chlorin e6 (Chenghai Chlorin, CHC, equivalent to commercially available chlorin e6) as raw material is dissolved in 5% sulfuric acid/methanol solution to a concentration of 0.1 M, and the reaction is performed for 10 hours and then concentrated at reduced pressure. The obtained acidic solution is diluted with an equal volume of DCM, and washed with water for several times to remove sulfuric acid. Then the organic phase is collected, dried, and concentrated to obtain compound 2.

$b_1$: Compound 2 is dissolved in DMF to a concentration of 0.1M, and then added with HBTU and DIEA. The reaction is carried out under stirring for 0.5-1 hour, and then added in sequence with β-alanine tert-butyl hydrochloride and DIEA, wherein the molar ratio of compound 2 to HBTU, DIEA, and β-alanine tert-butyl ester hydrochloride is 1:1-2:2-5:2-3. The reaction continues for 1-2 hours. After the reaction is completed, DCM is added to dilute the reaction. Then, the reaction is washed with water for several times, and the organic phase is collected, concentrated, and subjected to silica gel column chromatography to obtain compound 3.

$c_1$: Compound 3 and substituted α-olefin in 10-30 times of molar content excess of compound 3 are dissolved in DCM to a concentration of 0.02-0.1 M, and then added with Grubbs' catalyst. The reaction is performed under reflux for 16-24 hours and then filtered, and the obtained filtrate is transferred to a separating funnel, and washed with water for several times. The organic phase is collected, concentrated, and subjected to silica gel column chromatography to obtain a series of compound 4.

$d_1$: Compound 4 is dissolved in 25 vol % TFA/DCM solution to a concentration of 0.1 M. The reaction is carried out under stirring for 2-5 hours and then concentrated, and the residue is dissolved in DCM, and then washed with water. The organic phase is collected, and concentrated to obtain a series of compound 5.

$e_1$: Compound 5 is dissolved in DMF to a concentration of 0.1M, and then added with HBTU and DIEA. The reaction is carried out under stirring for 0.5-1 hour, and then added with an amino acid methyl ester hydrochloride and DIEA, wherein the molar ratio of compound 5 to HBTU, DIEA, and the amino acid methyl ester hydrochloride is 1:1-2:2-5:2-3. Then, the reaction continues for 1-2 hours. After the reaction is completed, DCM is added to dilute the reaction. Then, the reaction is washed with water for several times, and the organic phase is collected, concentrated, and subjected to silica gel column chromatography to obtain compound 6, namely, the chlorin derivative represented by formular (I) wherein M is 2H.

$e_{11}$: Compound 6 is dissolved in DCM to a concentration of 0.1 M, and added with a chloride or acetate complex of selected metal, wherein the molar ratio of compound 6 to the chloride or acetate complex of selected metal is 1:1-6. The reaction is heated to reflux for 2-8 hours and then washed with water, and the organic layer is collected, and concentrated to obtain a corresponding compound 7 wherein M is a metal ion defined as above.

$f_1$: Compound 6 is dissolved in acetone to a concentration of 0.03 M, and added with an equal volume of 0.5 N NaOH or KOH aqueous solution. The reaction is carried out under stirring for 2-10 hours, and then added with anhydrous ethanol to precipitate a solid. Then, the solid is filtered to obtain compound 8, namely, sodium or potassium carboxylate corresponding to compound 6 wherein M is 2H.

$f_{11}$: Compound 9 is synthesized by the synthesis method of compound 8 using compound 7 prepared above as raw material, wherein compound 9 is sodium or potassium carboxylate corresponding to compound 7 wherein M is a metal ion defined as above.

Compounds 6 and 7 here are compounds of formula II(a), and compounds 8 and 9 are compounds of formula II(b).

In the above preparation method, the specific reaction scheme is as follows:

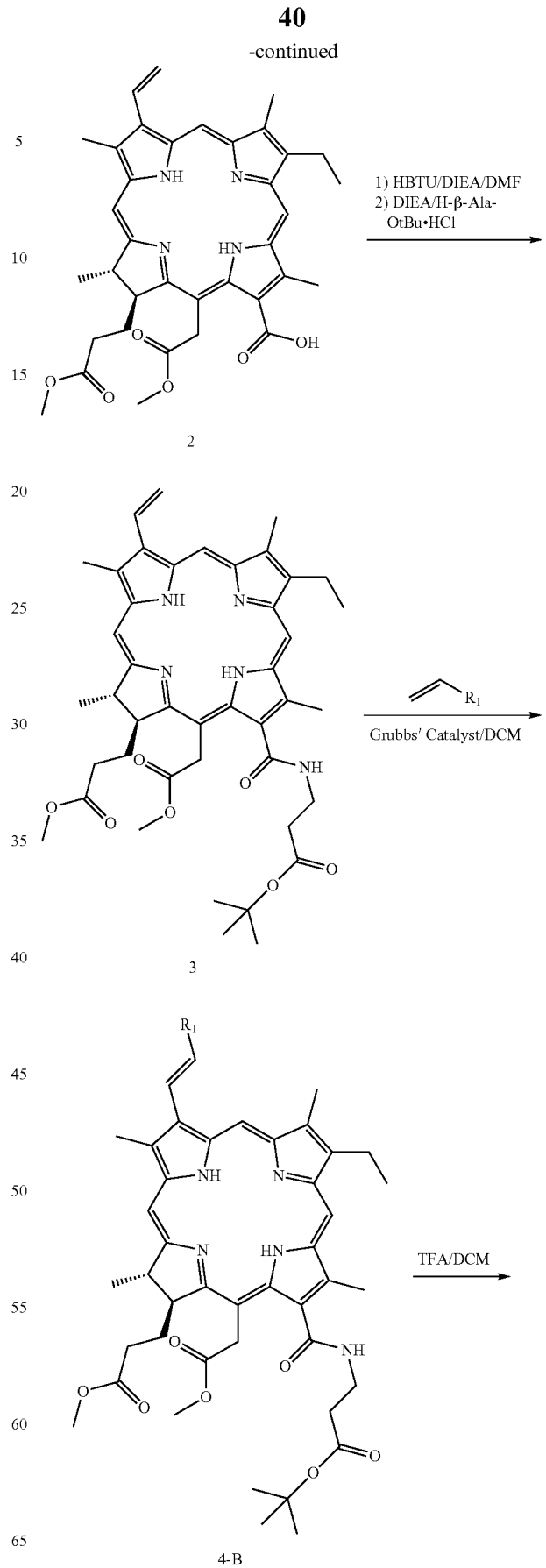

-continued

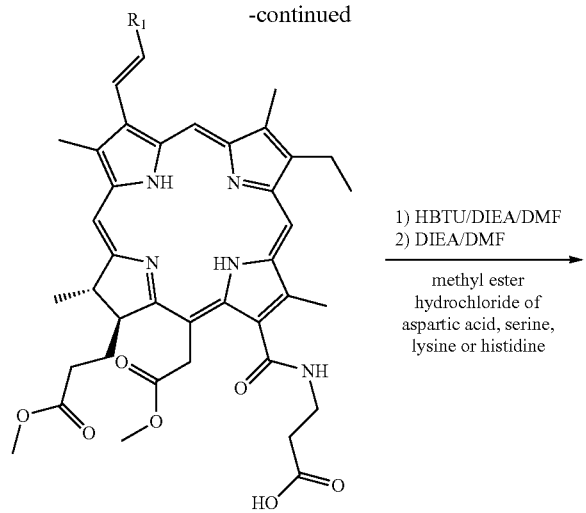

6 M = 2 H  } metal chloride or
7 M = mental ion  acetate complex

1) HBTU/DIEA/DMF
2) DIEA/DMF
——————→
methyl ester
hydrochloride of
aspartic acid, serine,
lysine or histidine NaOH or KOH aq/
Acetone
——————→

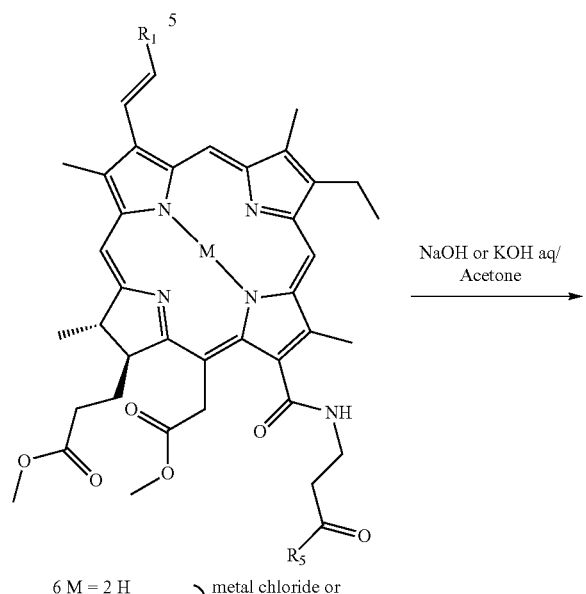

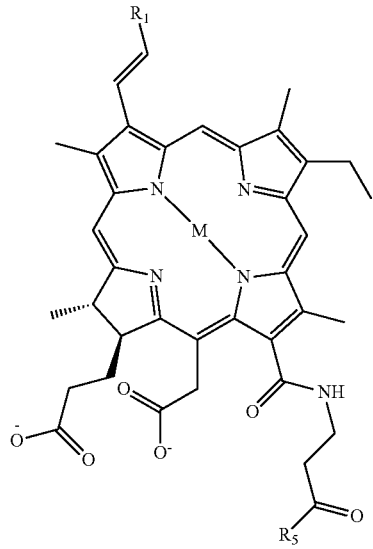

8 M = 2 H
9 M = mental ion wherein,
$R_1$ is

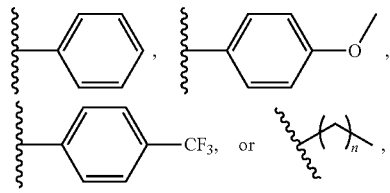

wherein n is any integer from 2 to 7; $R_8$ is any one of the following groups:

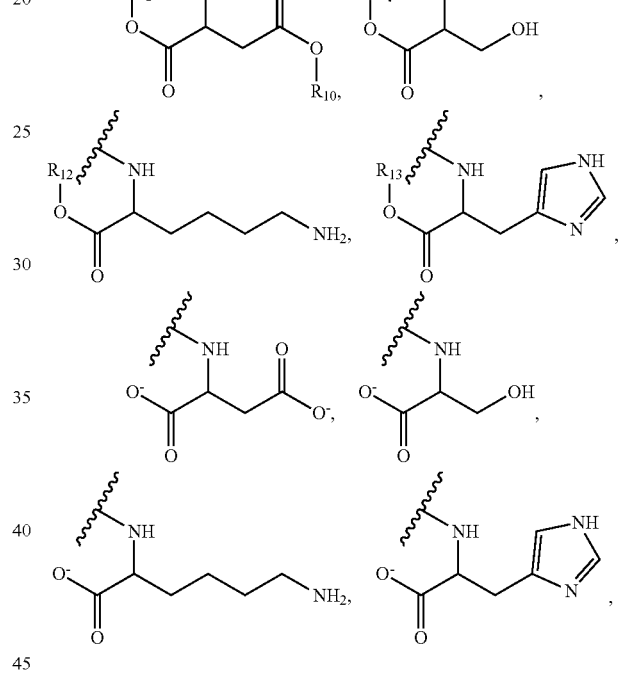

wherein $R_9$, $R_{10}$, $R_{11}$, $R_{12}$ and $R_{13}$ may be the same or different, and are each independently selected from $C_1$-$C_6$ alkyl;

M is 2H or a metal ion, for example, a divalent metal ion such as $Cu^{2+}$, $Fe^{2+}$, $Zn^{2+}$, $Mg^{2+}$, $Ni^{2+}$, $Co^{2+}$, $Pt^{2+}$ or $Pd^{2+}$; or a tetravalent metal ion such as $Sn^{4+}$ or $Ti^{4+}$.

In another particular embodiment, the method for preparing the chlorin derivative or the pharmaceutically acceptable salt thereof comprises the following steps:

$a_2$: Compound 1, chlorin e6, is dissolved in DMF to a concentration of 0.1 M, and then added with methyl iodide and anhydrous potassium carbonate, wherein the molar ratio of compound 1 to methyl iodide, and anhydrous potassium carbonate is 1:2-10: 2-10. The reaction is carried out under stirring for 1-4 hours, and then added with DCM for dilution. Then, the reaction is washed with water, and the organic phase is collected, concentrated, and subjected to silica gel column chromatography to obtain compound 10.

$b_2$: Compound 10 and substituted α-olefin in 10-30 times of molar content excess of compound 10 are dissolved in DCM to a concentration of 0.02-0.1 M, and then added with Grubbs' catalyst. The reaction is performed under reflux for 16-24 hours and then filtered, and the obtained filtrate is transferred into a separating funnel, and washed with water. The organic phase is collected, concentrated, and subjected to silica gel column chromatography to obtain a series of compound 11 wherein M is 2H.

$b_{21}$: Compound 11 is dissolved in DCM to a concentration of 0.1 M, and added with a chloride or acetate complex of selected metal, wherein the molar ratio of compound 11 to the chloride or acetate complex of selected mental is 1:1-6. The reaction is heated to reflux for 2-8 hours, and then washed with water, and the organic layer is collected, and concentrated to obtain a corresponding compound 12 wherein M is a metal ion defined as above.

$c_2$: Compound 11 is dissolved in THF and 1M KOH aqueous solution (v:v=1:1) to a concentration of 0.05 M. The reaction is carried out for 2-5 hours, concentrated at reduced pressure to remove THF, added with water to dilute the remaining alkaline solution, and adjusted to pH 5-6 to precipitate a solid, which is filtered to obtain a series of compound 13 wherein M is 2H.

$d_2$: Compound 13 is dissolved in DMF to a concentration of 0.1 M, and then added in sequence with EDCI, an amino acid methyl ester hydrochloride, triethylamine ($Et_3N$) and DIEA, wherein the molar ratio of compound 13 to EDCI, the amino acid methyl ester hydrochloride and DIEA is 1:1-2:1-2:0.1-0.5. The reaction is carried out under stirring for 0.5-2 hours, added with formic acid aqueous solution to precipitate a product, which is filtered and subjected to silica gel column chromatography to obtain a series of compound 15 wherein M is 2H.

$e_2$: Compound 15 is dissolved in acetone to a concentration of 0.03 M, and then added with equal volume of 0.5 N NaOH or KOH aqueous solution. The reaction is carried out under stirring for 2-10 hours, and then added with anhydrous ethanol to precipitate a solid, which is then filtered to obtain a series of compound 17, namely, sodium or potassium carboxylate corresponding to compound 15 wherein M is 2H.

$e_{21}$: Compounds 16 and 18 are systhesized by the synthesis method of compounds 15 and 17 using compound 12 prepared above as raw material, wherein compound 18 is sodium or potassium carboxylate corresponding to compound 16 wherein M is a metal ion defined as above.

Compounds 15 and 16 here are compounds of formula III(a), and compounds 17 and 18 are compounds of formula III(b).

In the above preparation method, the specific reaction scheme is as follows:

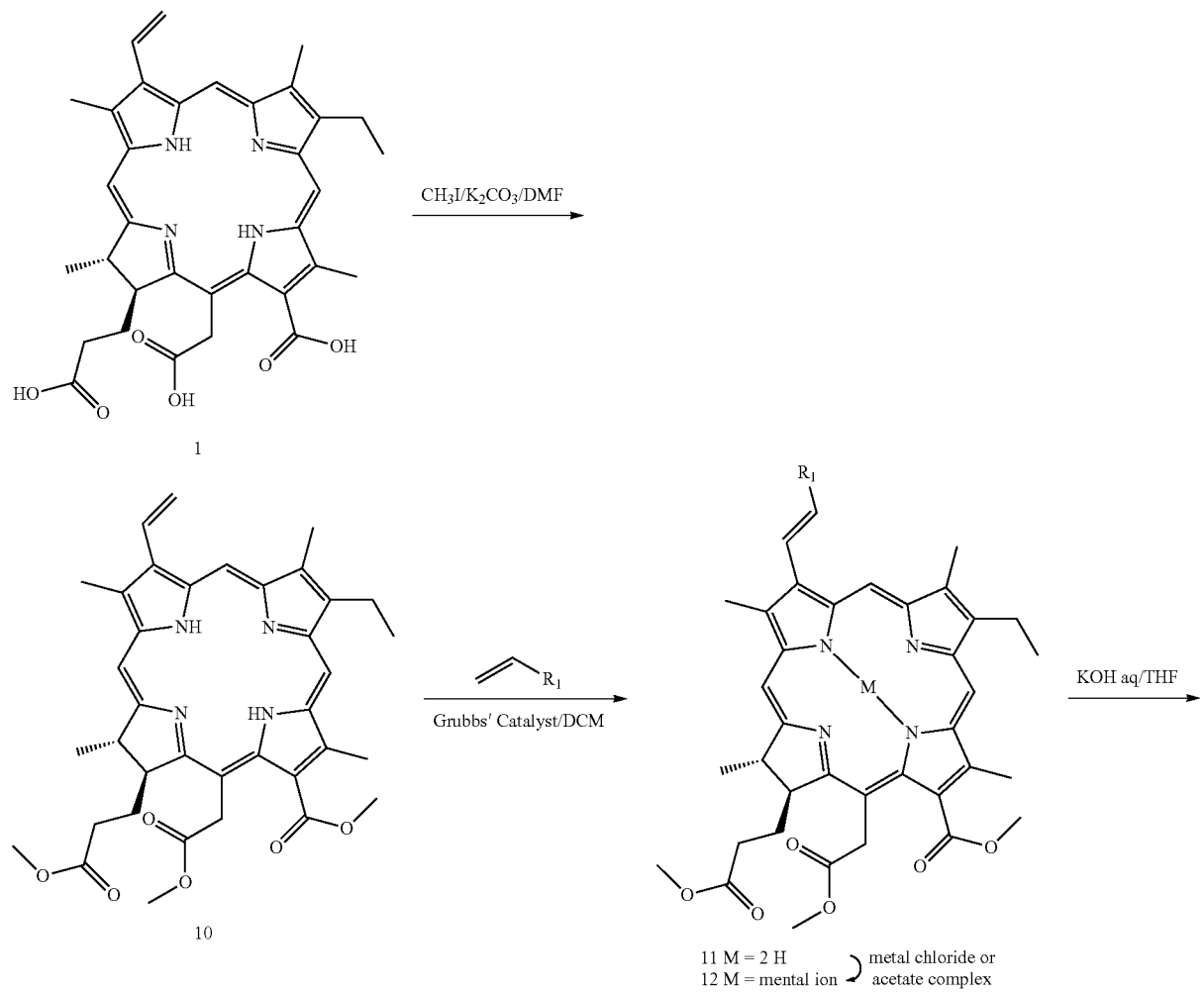

-continued
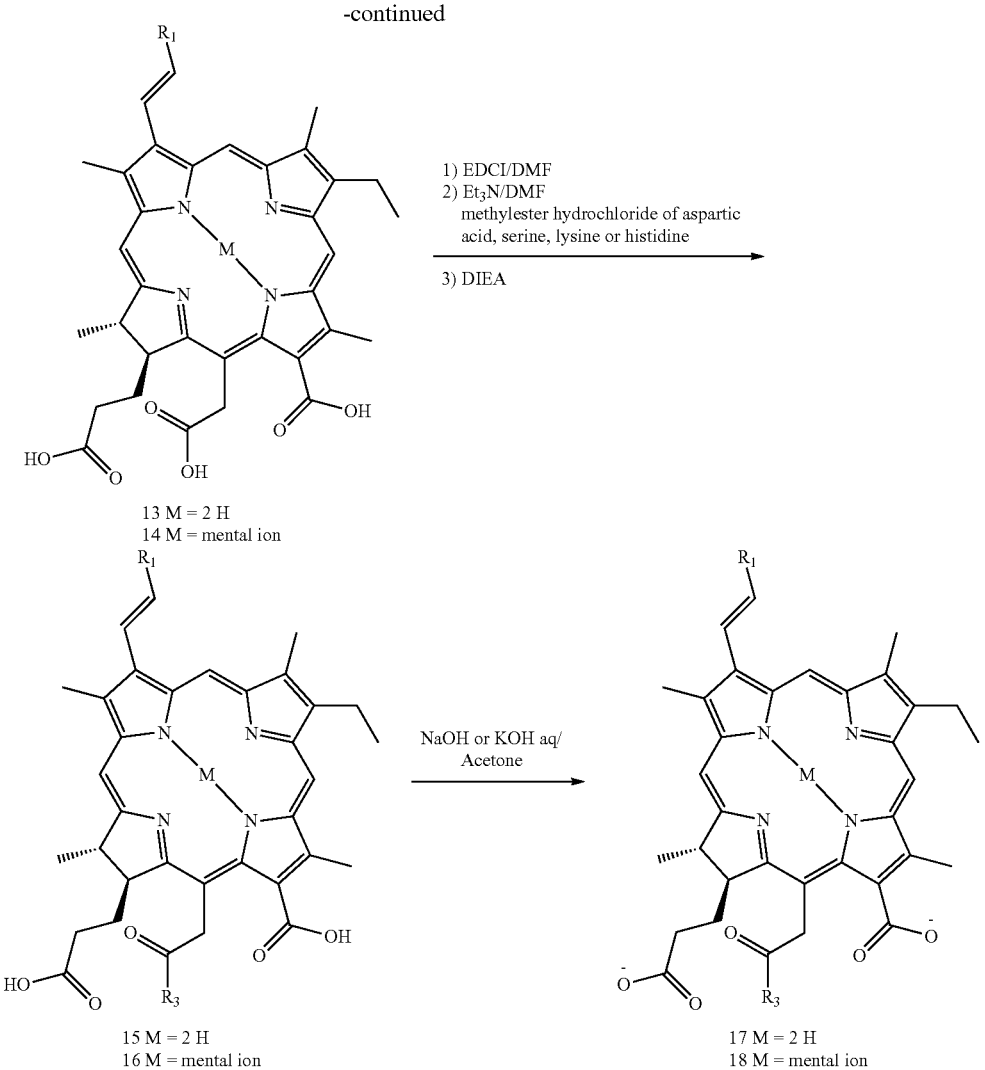
13 M = 2 H
14 M = mental ion
15 M = 2 H
16 M = mental ion
17 M = 2 H
18 M = mental ion
wherein, $R_1$ is
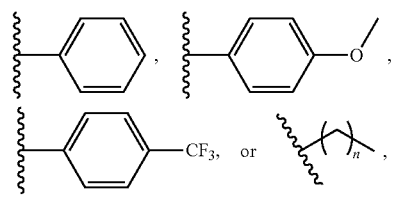
wherein n is any integer from 2 to 7; $R_3$ is any one of the following groups:
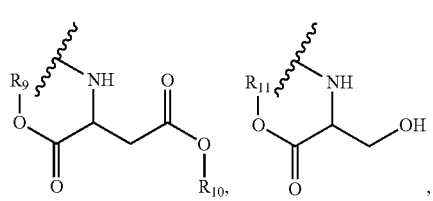
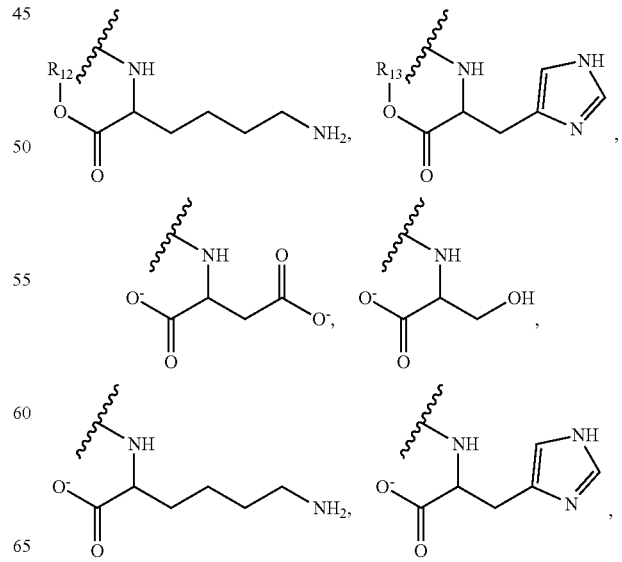

wherein $R_9$, $R_{10}$, $R_{11}$, $R_{12}$ and $R_{13}$ may be the same or different, and are each independently selected from $C_1$-$C_6$ alkyl; M is 2H or a metal ion, for example, a divalent metal ion such as $Cu^{2+}$, $Fe^{2+}$, $Zn^{2+}$, $Mg^{2+}$, $Ni^{2+}$, $Co^{2+}$, $Pt^{2+}$ or $Pd^{2+}$; or a tetravalent metal ion such as $Sn^{4+}$ or $Ti^{4+}$.

In yet another particular embodiment, the method for preparing the chlorin derivative or the pharmaceutically acceptable salt thereof comprises the following steps:

$a_3$: Compound 19 as raw material is dissolved in DMF to a concentration of 0.1M, and then added with HBTU and DIEA. The reaction is carried out under stirring for 0.5-1 hour, and then added with an amino acid methyl ester hydrochloride and DIEA. Then, the reaction continues for 1-2 hours. The molar ratio of compound 19 to HBTU, DIEA, and the amino acid methyl ester hydrochloride is 1:1-2:2-5:2-3. Then, the reaction is diluted with DCM, washed with water, and concentrated. The obtained residue is dissolved in 1% sodium methoxide/methanol solution, and the reaction is carried out under stirring for 5-10 hours, adjusted to pH6-7, and then concentrated at reduced pressure to remove methanol. The obtained residue is dissolved in DCM, and washed with water. The organic phase is collected, concentrated, and subjected to silica gel column chromatography to obtain a series of compound 20.

$b_3$: Compound 20 and substituted α-olefin in 10-30 times of molar content excess of compound 20 are dissolved in DCM to a concentration of 0.02-0.1 M, and then added with Grubbs' catalyst. The reaction is carried out under reflux for 16-24 hours and then filtered, and the obtained filtrate is transferred to a separating funnel, and washed with water for several times. The organic phase is collected, concentrated, and subjected to silica gel column chromatography to obtain a series of compound 21 wherein M is 2H.

$b_{31}$: Compound 21 is dissolved in DCM to a concentration of 0.1 M, and added with chloride or acetate complex of selected metal, wherein the molar ratio of compound 21 to the chloride or acetate complex of selected mental is 1:1-6. The reaction is heated to reflux for 2-8 hours and then washed with water, and the organic layer is collected, and concentrated to obtain corresponding metal complex 22 wherein M is a metal ion defined as above.

$c_3$: Compound 21 is dissolved in acetone to a concentration of 0.03 M, and added with an equal volume of 0.5 N NaOH or KOH aqueous solution. The reaction is carried out under stirring for 2-10 hours, and then added with anhydrous ethanol to precipitate a solid, which is then filtered to obtain the compound 23, namely, sodium or potassium carboxylate corresponding to compound 21 wherein M is 2H.

$c_{31}$: Compound 24 is synthesized by the synthesis method of compound 23 using compound 22 prepared above as raw material, wherein compound 24 is a sodium or potassium salt of corresponding compound 22 wherein M is a metal ion defined as above.

Compounds 21 and 22 here are compounds of formula IV(a), and compounds 23 and 24 are compounds of formula IV(b).

In the above preparation method, the specific reaction scheme is as follows:

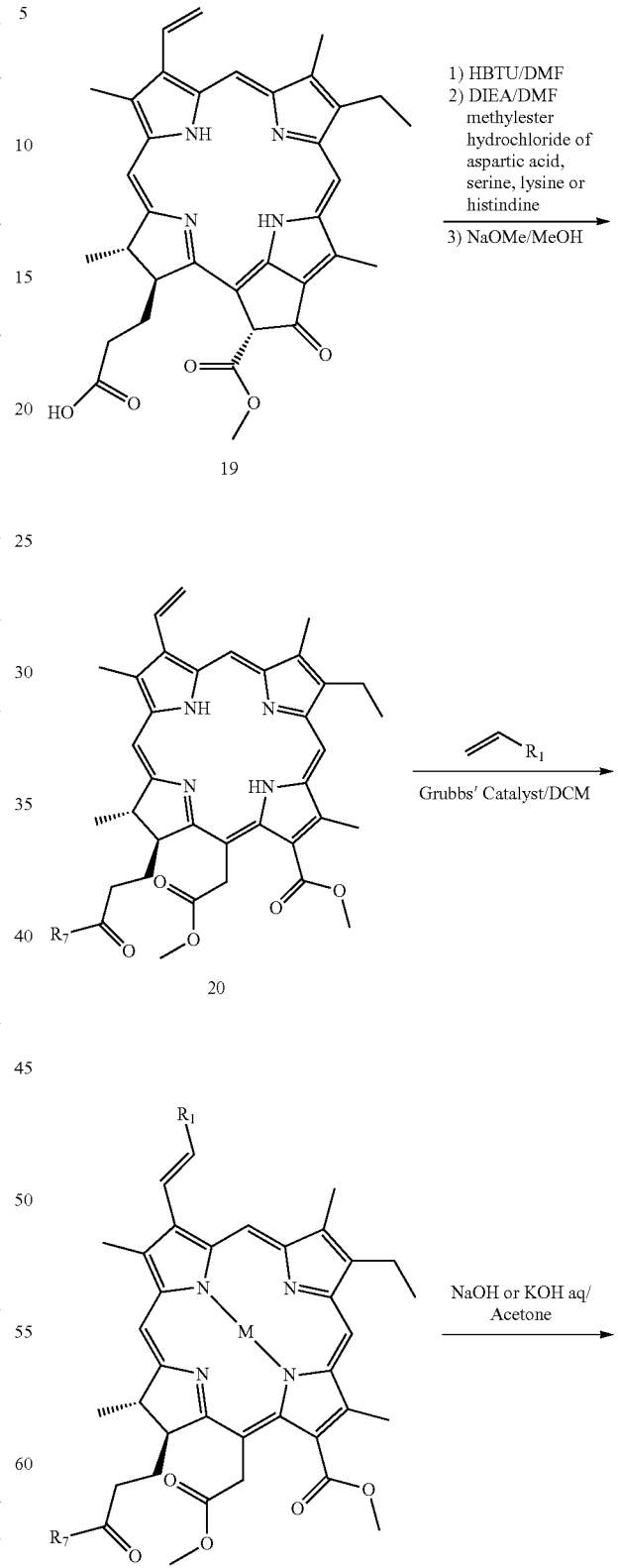

-continued

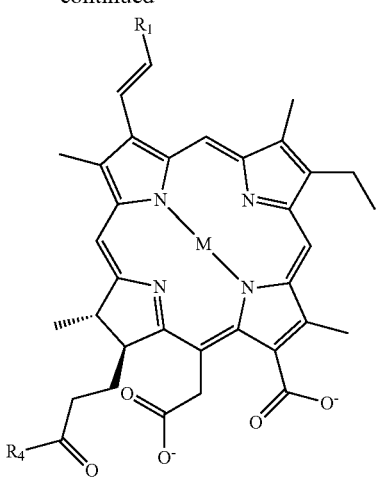

23 M = 2 H
24 M = mental ion wherein, $R_1$ is

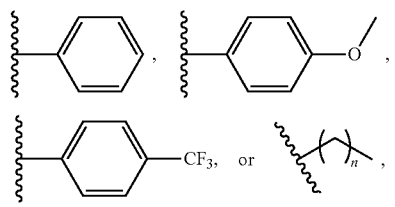

wherein n is any integer from 2 to 7; $R_4$ is any one of the following groups:

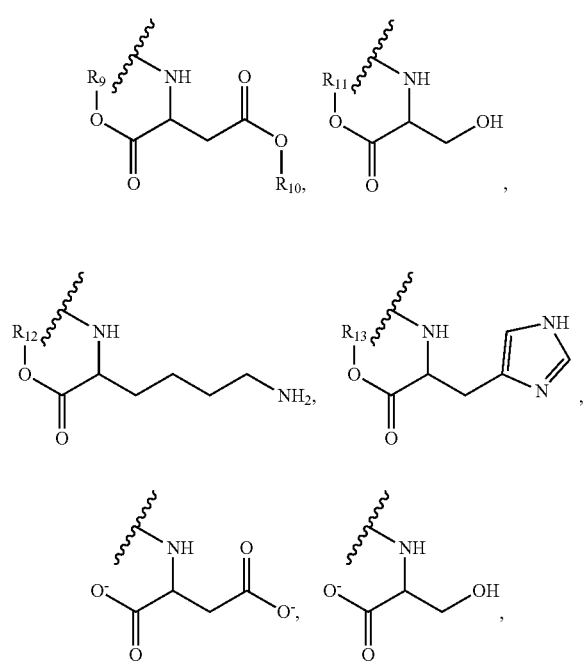

-continued

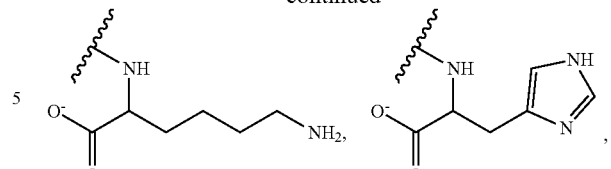

wherein $R_9$, $R_{10}$, $R_{11}$, $R_{12}$ and $R_{13}$ may be the same or different, and are each independently selected from $C_1$-$C_6$ alkyl;

M is 2H or a metal ion, for example. a divalent metal ion such as $Cu^{2+}$, $Fe^{2+}$, $Zn^{2+}$, $Mg^{2+}$, $Ni^{2+}$, $Co^{2+}$, $Pt^{2+}$ or $Pd^{2+}$; or a tetravalent metal ion such as $Sn^{4+}$ or $Ti^{4+}$.

In addition, the chlorin derivative or the pharmaceutically acceptable salt thereof according to the first aspect of the present disclosure can also be used as a photoacoustic sensitizer.

In the present disclosure, the term "photoacoustic sensitizer" specifically refers to a photosensitizer and/or a sonosensitizer.

The so-called "photosensitizer" refers to a compound that can absorb light source at a certain wavelength and then activate a series of photochemical and photophysical reactions to generate fluorescence or oxygen reactive species that can kill cells. The ideal photosensitizer has high selectivity, is highly distributed in lesion tissues as compared with in normal tissues, is uniformly distributed in the target tissues, and the matched light source has a strong ability to penetrate the tissue. The photosensitizer, after administration, can be accumulated in the target tissues to a peak in a short time, exhibits high efficiency of photodynamic reaction after exposure to light, and can be metabolized and eliminated quickly after exposure to light.

In practice, photosensitizers are often used in photodynamic therapy. Photodynamic therapy is a relatively novel non-invasive method for treatment of tumors. It relies on light source at a specific wavelength to excite the photosensitizers in tumor tissues to produce reactive oxygen species (ROS) with biological toxicity such as singlet oxygen, which in turn oxidizes and damages the tumors to inhibit tumor growth or eliminate tumors.

The so-called "sonosensitizer" refers to a type of substance that can be excited under ultrasonic irradiation, and will undergo a series of reactions with surrounding oxygen molecules upon excitation, thereby producing reactive species with high oxidation activity such as singlet oxygen. Singlet oxygen is a highly reactive oxygen free radical, which has cytotoxicity, especially to the sites such as cell membranes, mitochondria and the like. The sonosensitizer can interact with a variety of biological macromolecules in the cell and cause damage to the cell membrane system by binding to the macromolecules.

In practice, sonosensitizer are often used in sonodynamic therapy. Sonodynamic therapy is a novel method for treatment of tumors with sonosensitizers and ultrasound. The therapy utilizes the ultrasound's properties that it has strong penetration in biological tissues, is non-invasive and can accurately focus and transfer energy, thereby transferring energy to the tumor site, so as to excite the sonosensitizer that has specifically bound to the tumor tissue in advance, and thus trigger a chemical reaction to generate chemical energy, thereby destroying the tumor and achieving the purpose of further reducing the survival rate of the tumor.

As described above, the chlorin derivative or the pharmaceutically acceptable salt thereof according to the present disclosure is obtained by modifying the structure of chlorin e6, and the purpose of the modification is to obtain a chlorin derivative with further improved performance (for example, more specific selectivity on tumors, longer absorption wavelength, and better water solubility) in comparison with chlorin e6, and the following examples also further confirm that the performance has been improved, while the intrinsic photosensitivity and ultrasonic sensitivity of chlorin e6 is still retained. Thus, the chlorin derivative or the pharmaceutically acceptable salt thereof according to the present disclosure can be used in photodynamic therapy and sonodynamic therapy.

According to a third aspect of the present disclosure, provided is an anti-tumor composition, comprising: the chlorin derivative or the pharmaceutically acceptable salt thereof according to the first aspect of the present disclosure, and a pharmaceutically acceptable excipient.

The so-called "anti-tumor composition" refers to a class of drugs for treatment of tumor diseases. The term "treatment" mentioned here refers to the process of inhibiting the growth or metastasis of tumors in a subject, or eliminating tumors in a subject.

The term "tumor" herein comprises benign tumor and malignant tumor such as carcinoma in situ and cancer metastasis. Thus, in an embodiment, the tumor comprises benign tumor and malignant tumor, for example, carcinoma in situ and cancer metastasis. In a further embodiment, the carcinoma in situ comprises, for example, breast cancer, liver cancer, lung cancer and colorectal cancer. In another embodiment, the cancer metastasis comprises, for example, breast cancer metastasis, liver cancer metastasis, lung cancer metastasis and colorectal cancer metastasis.

As mentioned above, the chlorin derivative or the pharmaceutically acceptable salt thereof according to the present disclosure has photosensitivity and ultrasonic sensitivity, and thus can be used in photodynamic therapy and sonodynamic therapy, thereby inhibiting tumor growth or metastasis in vivo, and/or eliminate tumors in vivo. Therefore, the chlorin derivative or the pharmaceutically acceptable salt thereof according to the present disclosure is used as an anti-tumor drug.

In addition, in addition to the chlorin derivative or the pharmaceutically acceptable salt thereof of the present disclosure, the anti-tumor composition according to the present disclosure may further comprise a pharmaceutically acceptable excipient.

The term "pharmaceutically acceptable excipient" is intended to comprise solvents, stabilizers, surfactants, fillers, preservatives, dispersion media, buffers, isotonic agents, absorption retarder, and the like. The anti-tumor composition according to the present disclosure can be processed into a solid form, for example, processed into a freeze-dried or vacuum-dried powder that can be reconstituted with a suitable liquid (such as saline or water) before administration to a subject. Alternatively, the anti-tumor composition according to the present disclosure can be directly formulated as a liquid formulation. The use of such pharmaceutically acceptable excipient in active pharmaceutical ingredients is well known in the art. The use of any conventional pharmaceutically acceptable carrier or pharmaceutically acceptable excipient in the anti-tumor composition according to the present disclosure can be expected, unless it is incompatible with the active pharmaceutical ingredient(s).

In the present disclosure, the anti-tumor composition according to the present disclosure can be formulated as an injection first and injected into the subject, and then the corresponding treatment can be performed. Therefore, in an embodiment, the anti-tumor composition can be an injection.

In view of the intrinsic performance of the photoacoustic sensitizer and the anti-tumor drug of the present disclosure, those skilled in the art can understand that they can be used in photodynamic therapy or sonodynamic therapy together with oxygen and light radiation or ultrasound.

According to a fourth aspect of the present disclosure, provided is use of the chlorin derivative or the pharmaceutically acceptable salt thereof according to the first aspect of the present disclosure in the treatment of a tumor.

In an embodiment, the tumor comprises benign tumor and malignant tumor, for example, carcinoma in situ and cancer metastasis. In a further embodiment, the carcinoma in situ comprises, for example, breast cancer, liver cancer, lung cancer and colorectal cancer. In another embodiment, the cancer metastasis comprises, for example, breast cancer metastasis, liver cancer metastasis, lung cancer metastasis and colorectal cancer metastasis.

Similar to the third aspect of the present disclosure, the chlorin derivative or the pharmaceutically acceptable salt thereof can be an injection formulation.

Similarly, in view of the performance of the photoacoustic sensitizer and the anti-tumor drug of the present disclosure, those skilled in the art can understand that they can be used in photodynamic therapy or sonodynamic therapy together with oxygen and light radiation or ultrasound. Thus, in an embodiment, the treatment is performed by photodynamic therapy or sonodynamic therapy.

In an embodiment, the photodynamic therapy is performed with light waves at a wavelength of 600-800 nm, such as 660 nm, and the sonodynamic therapy is performed with ultrasounds at an intensity of 1.88 $W/cm^2$.

According to a fifth aspect of the present disclosure, provided is a combination of the chlorin derivative or the pharmaceutically acceptable salt thereof according to the first aspect of the present disclosure and an ultrasonic medical system, the ultrasonic medical system comprises a transducer ultrasonic bed and a contact agent, wherein the transducer ultrasonic bed comprises a bottom and a wall extending upward from the bottom; the bottom is provided, at positions corresponding to head, torso, and limbs of a subject, respectively, with at least one transducer for transmitting ultrasonic waves to the subject thereon; the wall is provided, at positions corresponding to the head and limbs of the subject, respectively, with at least one ultrasonic transducer for transmitting ultrasonic waves to the subject; and the contact agent is used to transmit ultrasonic waves between the subject and the ultrasonic transducers.

In an embodiment, the ultrasonic medical system further comprises a transducer module assembly, wherein the transducer module assembly is installed above the transducer ultrasonic bed and comprises at least one transducer for transmitting ultrasonic waves to the subject therebelow; and the contact agent is also used to transmit ultrasonic waves between the subject and the at least one ultrasonic transducer.

In an embodiment, the transducer module assembly further comprises a numerically controlled motion device for controlling the movement of the transducer module assembly in a horizontal and/or vertical direction.

In an embodiment, the ultrasonic wave is a pulse wave or a continuous wave.

In an embodiment, the ultrasonic wave has a frequency of 0.3-3 MHz; and preferably, the ultrasonic wave has an ultrasound intensity of 0.1-3 W/cm².

In an embodiment, the contact agent is at least one of water and vacuum degassed cold/hot water.

In an embodiment, the ultrasonic medical system further comprises an automatic control system with a programmable logic controller, and a contact agent supply system, wherein the contact agent supply system is connected to the transducer ultrasonic bed, so as to supply the contact agent to the transducer ultrasonic bed; the automatic control system with a programmable logic controller is respectively connected to the transducer ultrasonic bed, the transducer module assembly and the contact agent supply system, so as to control the supply of the contact agent from the contact agent supply system to the transducer ultrasonic bed, and to control the operation of at least some of the ultrasonic transducers of the transducer ultrasonic bed and the transducer module assembly.

In an embodiment, the automatic control system with a programmable logic controller further comprises a monitoring system for displaying at least one of the following: a. working parameters of at least some of the ultrasonic transducers in the transducer ultrasonic bed and in the transducer module assembly; and b. lesion information within the subject.

In an embodiment, the chlorin derivative or the pharmaceutically acceptable salt thereof is prepared by the method according to the second aspect of the present disclosure.

The present disclosure will be described in further detail below in combination with the specific examples.

EXAMPLES

Example 1: Preparation of Compounds 8-BA and 9-BA(Pd)

The synthetic routes of compounds 8-BA and 9-BA(Pd) are as follows:

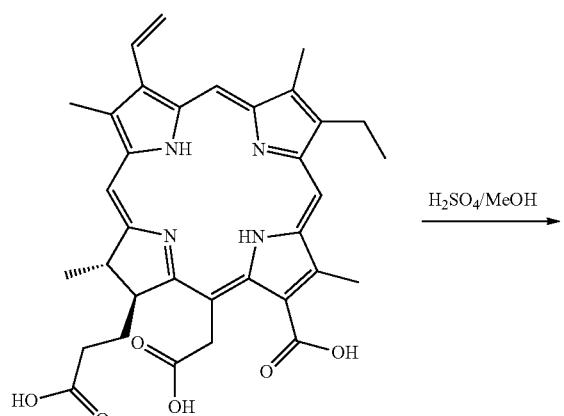

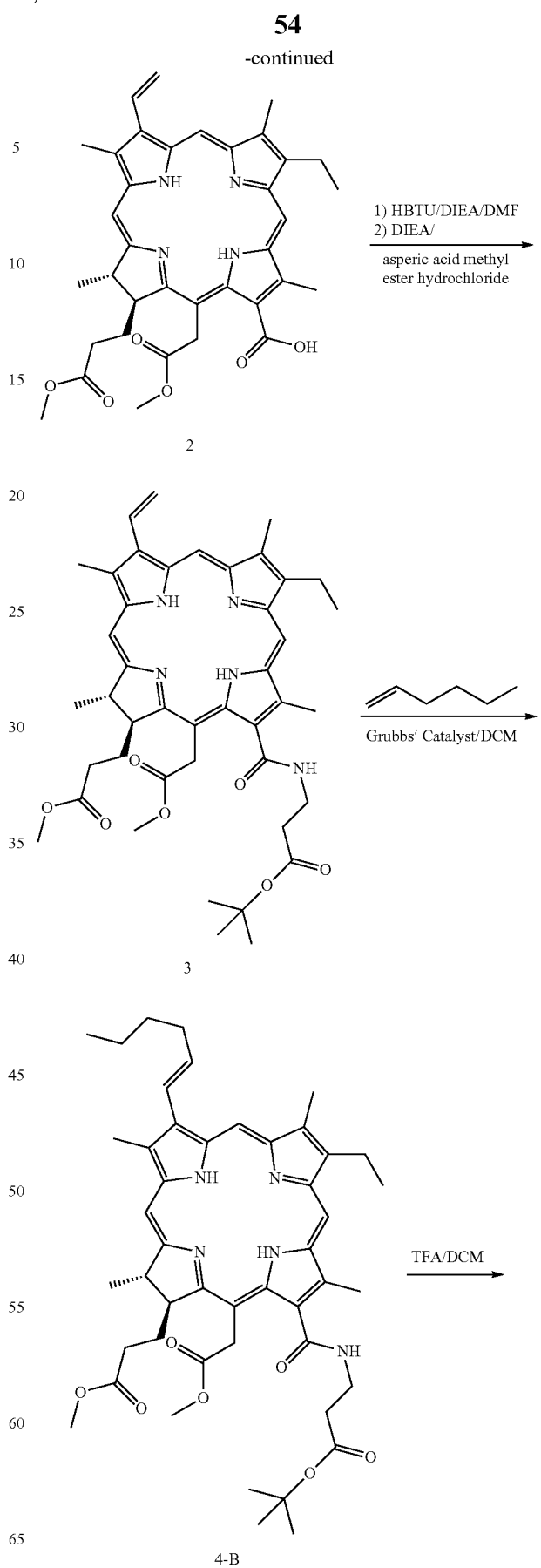

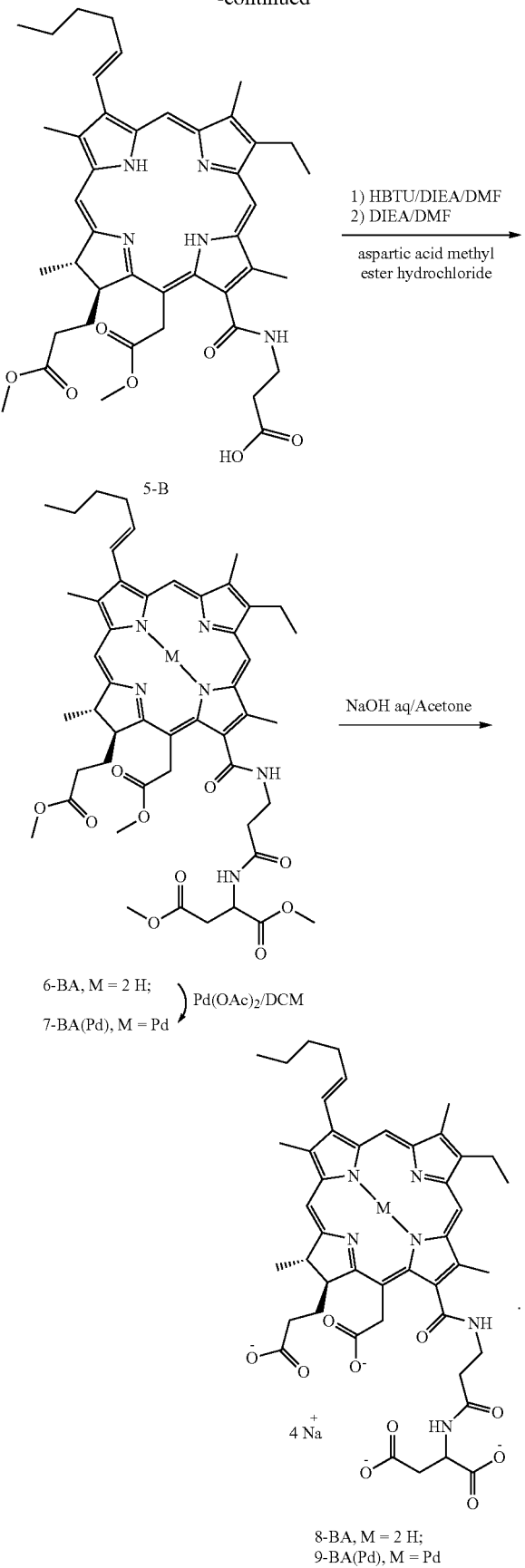

The steps in the above synthetic route are as follows:

541 mg of compound 1 was dissolved in 5% sulfuric acid/methanol solution to a concentration of 0.1 M. The reaction was performed for 10 hours and then concentrated at reduced pressure. The obtained acidic solution was diluted with an equal volume of dichloromethane (DCM), and washed with water. Then, the organic phase was collected and concentrated to obtain compound 2, which was to be directly used in the next reaction without separation.

Compound 2 as product obtained in the previous step was dissolved in dimethylformamide (DMF) to a concentration of 0.1M, and then added with 435 mg of o-benzotriazole-1-yl-N,N,N',N'-tetramethyluronium hexafluorophosphate (HBTU) and 189 μL of N,N-diisopropylethylamine (DIEA). The reaction was stirred for 0.5-1 hour, and then added in sequence with 417 mg of β-alanine tert-butyl hydrochloride and 379 μL of DIEA. The reaction continued for 1-2 hours. After being completed, the reaction was added with dichloromethane (DCM) for dilution, and then washed with water, and the organic phase was collected, concentrated, and subjected to 200-300 mesh silica gel column chromatography (eluted with petroleum ether/acetone=3:1) to obtain 545 mg of compound 3. The two-step yield was 80%.

Compound 3 ($C_{43}H_{55}N_6O_7$, MW=766.4127): $^1$H NMR (400 MHz, CD3COCD3) δ 9.59 (1H, s), 9.57 (1H, s), 9.07 (1H, s), 8.14 (1H, m), 8.05 (1H, dd, J=11.6, 17.8 Hz), 6.35 (1H, m), 6.25 (1H, dd, J=1.3, 17.8 Hz), 6.98 (1H, dd, J=1.3, 17.8 Hz), 5.65 (1H, d, J=19.1 Hz), 5.38 (1H, d, J=19.1 Hz), 4.65 (1H, q, J=7.2 Hz), 4.50 (1H, m), 3.91 (1H, m), 3.79 (1H, m), 3.75 (3H, s), 3.60 (3H, s), 3.56 (2H, m), 3.54 (2H, q, J=7.6 Hz), 3.47 (3H, s), 3.42 (3H, s), 3.14 (3H, s), 2.69 (1H, m), 2.34 (1H, m), 2.26 (1H, m), 1.79 (1H, m), 1.70 (3H, d, J=7.2 Hz), 1.59 (3H, t, J=7.6 Hz), 1.44 (9H, s), −1.66 (1H, s), −1.95 (1H, s). ESI-MS m/z: $C_{43}H_{55}N_6O_7$ [M+H]+, calculated value: 767.4127, and measured value: 767.4143.

500 mg of compound 3 and 1.660 mL of 1-hexene were dissolved in dichloromethane (DCM) to a concentration of 0.03 M, and added with 169 mg of second-generation Grubbs' catalyst. The reaction was performed under reflux for 20 hours and then filtered, and the filtrate was transferred to a separating funnel, and washed with saturated ammonium chloride aqueous solution. Then, the organic phase was collected, concentrated, and subjected to 200-300 mesh silica gel column chromatography (eluted with petroleum ether/acetone=9:2) to obtain 376 mg of compound 4-B ($C_{47}H_{61}N_5O_7$, MW=807.4571): $^1$H NMR (400 MHz, $CD_3COCD_3$) δ 9.59 (1H, s), 9.55 (1H, s), 9.03 (1H, s), 8.13 (1H, m), 8.01 (1H, dd, J=11.6, 17.8 Hz), 6.31 (1H, m), 6.22 (1H, dd, J=1.3, 17.8 Hz), 6.97 (1H, dd, J=1.3, 17.8 Hz), 6.44 (1H, d, J=19.1 Hz), 6.06 (1H, d, J=19.1 Hz), 4.59 (1H, q, J=7.2 Hz), 4.49 (1H, m), 3.90 (1H, m), 3.77 (1H, m), 3.74 (3H, s), 3.59 (3H, s), 3.54 (2H, m), 3.51 (2H, q, J=7.6 Hz), 3.45 (3H, s), 3.42 (3H, s), 3.13 (3H, s), 2.67 (1H, m), 2.34 (1H, m), 2.25 (1H, m), 2.16 (2H, m), 1.77 (1H, m), 1.68 (3H, d, J=7.2 Hz), 1.57 (3H, t, J=7.6 Hz), 1.42 (9H, s), 1.38 (2H, m), 1.29 (2H, m), 0.98 (3H, m), −1.65 (1H, s), −1.93 (1H, s). ESI-MS m/z: $C_{47}H_{62}N_5O_7$ [M+H]$^+$, calculated value: 808.4571, and measured value: 808.4577.

300 mg of compound 4 was dissolved in 25 vol % trifluoroacetic acid (TFA)/dichloromethane (DCM) solution to a concentration of 0.1 M. The reaction was carried out under stirring for 2-5 hours, and then concentrated, and the residue was dissolved in DCM, and then washed with water. The organic phase was collected, and concentrated to obtain 279 mg of compound 5-B.

250 mg of compound 5-B was weighted directly and dissolved in dimethylformamide (DMF) to a concentration of 0.1 M, and then added with 189 mg of o-benzotriazole-1-yl-N,N,N',N'-tetramethyluronium hexafluorophosphate (HBTU) and 87 μL of N,N-diisopropylethylamine (DIEA). Then the reaction was carried out under stirring for 0.5-1 hours, and then added with 197 mg of L-aspartic acid methyl ester hydrochloride and 174 μL of N,N-diisopropylethylamine (DIEA). Then the reaction continued for 1 hour. After being completed, the reaction was added with dichloromethane (DCM) for dilution, and then washed with water for several times, and the organic phase was collected, concentrated, and subjected to 200-300 mesh silica gel column chromatography (eluted with petroleum ether/acetone=1:1) to obtain 253 mg of compound 6-BA ($C_{49}H_{62}N_6O_{10}$, MW=894.4527) with a yield of 85%; compound 6-BA: H NMR (400 MHz, $CD_3COCD_3$) δ 8.41 (1H, s), 8.32 (1H, s), 8.13 (1H, m), 8.01 (1H, dd, J=11.6, 17.8 Hz), 6.31 (1H, m), 6.22 (1H, dd, J=1.3, 17.8 Hz), 6.97 (1H, dd, J=1.3, 17.8 Hz), 6.44 (1H, d, J=19.1 Hz), 6.06 (1H, d, J=19.1 Hz), 5.03 (1H, m), 4.59 (1H, q, J=7.2 Hz), 4.49 (1H, m), 3.90 (1H, m), 3.77 (1H, m), 3.74 (3H, s), 3.59 (3H, s), 3.66 (6H, s), 3.54 (2H, m), 3.51 (2H, q, J=7.6 Hz), 3.45 (3H, s), 3.42 (3H, s), 3.13 (3H, s), 3.04 (2H, m), 2.79 (1H, m), 2.34 (1H, m), 2.25 (1H, m), 2.16 (2H, m), 1.77 (1H, m), 1.68 (3H, d, J=7.2 Hz), 1.57 (3H, t, J=7.6 Hz), 1.38 (2H, m), 1.29 (2H, m), 0.98 (3H, m), −1.65 (1H, s), −1.93 (1H, s). ESI-MS m/z: $C_{49}H_{61}N_6O_{10}$ [M−H]$^-$, calculated value: 893.4527, and measured value: 893.4523.

200 mg of compound 6-BA was dissolved in dichloromethane (DCM) to a concentration of 0.1 M, and then added with 79 mg of palladium dichloride. The reaction was heated to reflux for 5 hours, and then washed with water. The organic layer was collected, concentrated, and subjected to 200-300 mesh silica gel column chromatography (eluted with petroleum ether/acetone=3:1) to obtain 239 mg of metal complex 7-BA, which is easily soluble in water, and the yield was 90%.

200 mg of compounds 6-BA and 200 mg of 7-BA were respectively dissolved in acetone to a concentration of 0.03 M, and added with equal volume of 0.5N NaOH aqueous solution. The reaction was carried out under stirring for 5 hours, and then added with anhydrous ethanol to precipitate a solid. Then, the precipitated solid was filtered to obtain 205 mg of compound 8-BA and 206 mg of compound 9-BA(Pd), respectively. Compound 9-BA(Pd): $C_{45}H_{48}N_6Na_4O_{19}Pd$, MW=1030.2058. $^1$H NMR (400 MHz, MeOD): δ 8.44 (1H, s), 8.37 (1H, s), 6.70 (1H, s), 6.40 (1H, s), 6.43 (1H, d, J=19.1 Hz), 6.09 (1H, d, J=19.1 Hz), 5.03 (1H, m), 4.30 (1H, s), 3.90 (1H, m), 3.44 (2H, m), 3.44 (2H, m), 2.90 (2H, m), 2.65 (1H, m), 2.44 (4H, m), 2.42 (3H, s), 2.33 (2H, m), 2.37 (3H, s), 2.20 (1H, m), 2.12 (3H, s), 1.79 (2H, m), 1.88 (1H, m), 1.38 (2H, m), 1.29 (2H, m), 0.93 (3H, m), 0.89 (3H, m), 0.86 (3H, d, J=7.2 Hz). HRMS (ESI) m/z: $C_{45}H_{48}N_6Na_2O_{19}Pd$[M−2Na]$^-$, calculated value: 984.2262, measured value: 984.2269.

Example 2: Effect of Compound 9-BA(Pd) on Breast Cancer and Breast Cancer Metastasis The sonodynamic therapy with the water-soluble chlorin derivative 9-BA(Pd) synthesized in Example 1 as a ultrasonic sensitizer (sonosensitizer for short) was evaluated on tumor-bearing mice suffering from lung metastasis of breast cancer in ultrasound field.

The water-soluble chlorin derivative 9-BA(Pd) was dissolved in normal saline to prepare a drug solution for administration. Balb/c mice (female, 18-22 g) were injected with 4T1 mice breast cancer cells directly under the second pair of nipples on the left side, to construct a model of mice suffering from lung metastasis of breast cancer. Tumor volume and body weight of the mice were recorded from the 7$^{th}$ day of tumor injection, and measured every other day. The tumor-bearing mice were randomly divided into 4 groups: (1) a: control group (saline alone), (2) b: ultrasound group (ultrasound alone), (3) c: administration (9-BA(Pd)) group, (4) d: administration+ultrasound (9-BA(Pd)+ultrasound) group (i.e., sonodynamic therapy group). The administration and/or ultrasound treatment was/were performed on the 12$^{th}$, 14$^{th}$, 18$^{th}$, 20$^{th}$, 24$^{th}$, and 26$^{th}$ days after tumor injection. Mice were injected with 16 mg/kg of the sonosensitizer via tail vein, and subjected to ultrasound treatment 2 hours after administration. After 24 hours, the mice were administered again, and subjected to ultrasound treatment after 2 hours again. The ultrasound treatment was conducted by ultrasound irradiation of 1.88 W/cm$^2$ for 30 min. The tumor tissue was dissected for analysis and weight recording. The lung tissue was stained with Bouin's fixative and decolorized with ethanol, and then the number of lung nodules was recorded and subjected to statistical analysis.

It was observed that the mice in the control group and in the ultrasound group had an average tumor volume increased at a faster rate, while the administration group (sonosensitizer 9-BA(Pd) alone) had a slightly inhibitory effect on the tumor growth, and the mice in the sonodynamic therapy group showed the most significant inhibitory effect on the tumor growth and had the slowest tumor growth (compared with other groups, P<0.01).

After the experiment was completed, the dissected tumor tissues were weighed. FIG. 1 shows the effect of the treatment in the groups on the weight of tumor tissue in mice suffering from primary breast cancer. It can be seen from FIG. 1 that after administration of compound 9-BA(Pd) in combination with ultrasound treatment (i.e., the sonodynamic therapy group), the weight of the tumor tissue was reduced compared with the other groups, and there was a significant difference. Correspondingly, from observation of the dissected tumor tissues, it can be found that the size of tumor tissue in the sonodynamic therapy group was significantly reduced, with a statistical significance of P<0.01-0.001.

Figure 2:
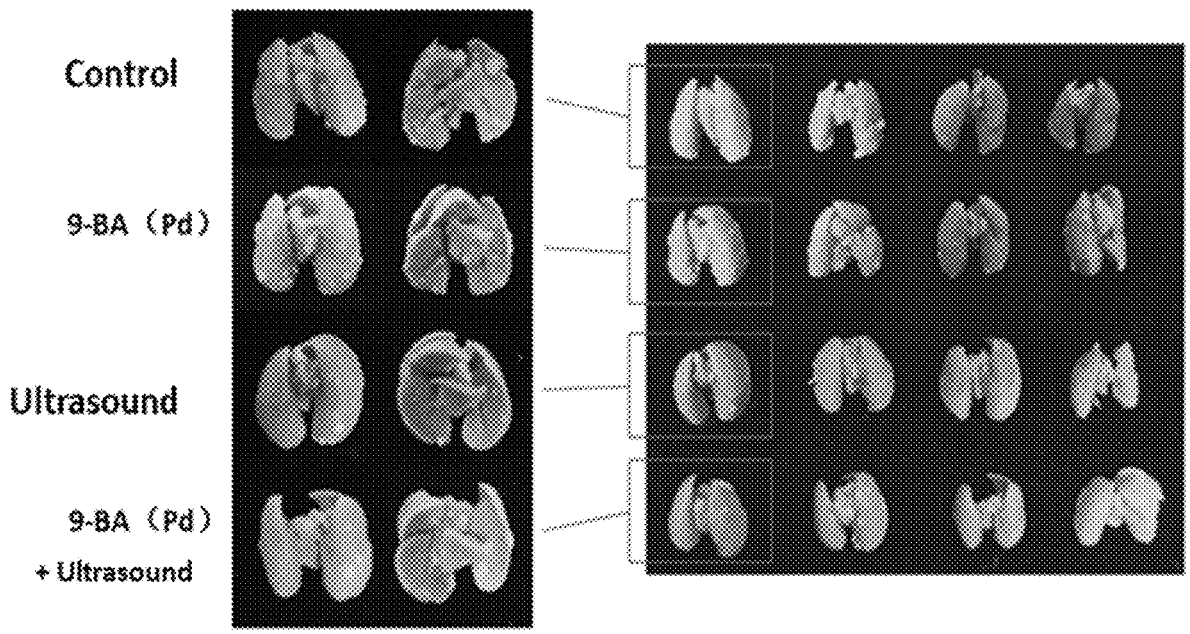
FIG. 2 is a photograph showing the inhibitory effect of compound 9-BA(Pd) according to the present disclosure and the ultrasonic treatment, alone or in combination, on lung metastasis of primary breast cancer.

FIG. 2 is a photograph showing the inhibitory effect of the treatment in the groups on lung metastasis of primary breast cancer. It can be seen from FIG. 2 that the tumor-bearing mice in the groups developed lung metastasis of tumor to a different extent and the mice in the control group had more serious lung metastasis and more tumor nodules in the lung; after treatment, the number of tumor nodules in the lung of mice was decreased, and the extent of lung metastasis of tumor in the sonodynamic therapy group was significantly reduced, indicating that the administration of compound 9-BA(Pd) in combination with ultrasound treatment in free field can inhibit the lung metastasis of breast tumor.

To sum up, a series of water-soluble chlorin-based sonosensitizers such as compound 9-BA(Pd) as provided by the present disclosure can be combined with ultrasound to perform sonodynamic therapy, which shows a significant inhibitory effect on tumors and tumor tissues, and can inhibit lung metastasis of primary breast cancer in mice, showing clinical value.

Example 3: Preparation of Compounds 17-MPA and 18-MPA(Pd)
The synthetic routes of compounds 17-MPA and 18-MPA(Pd) are as follows:
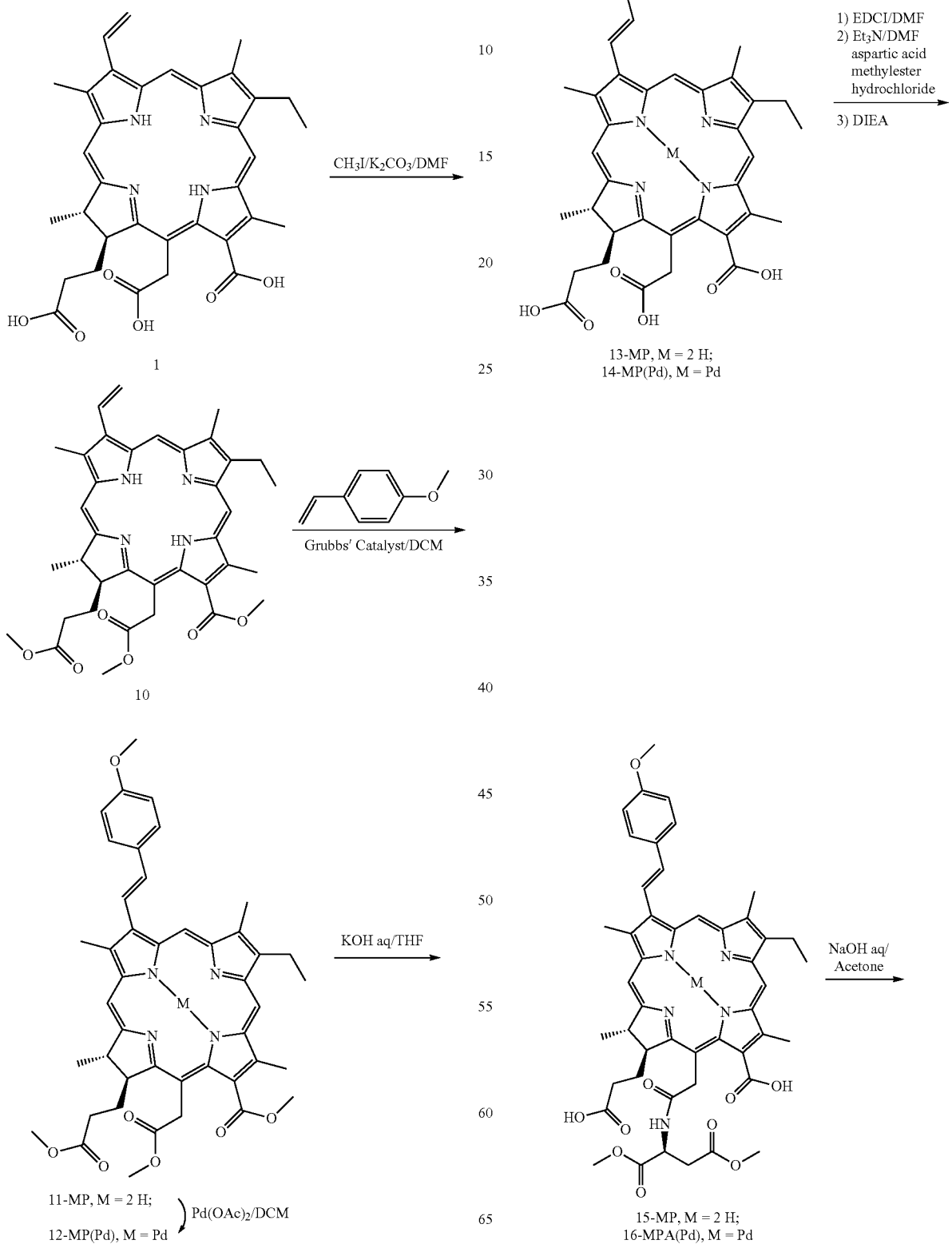

-continued

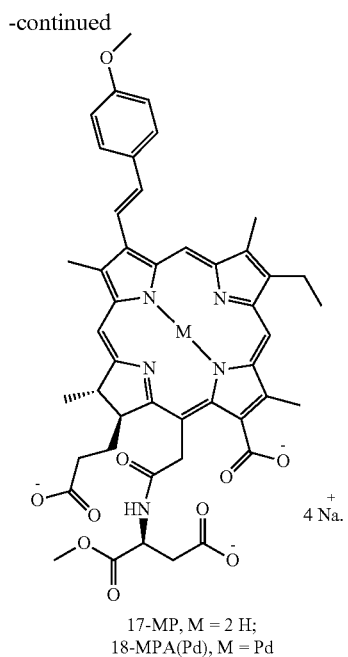

17-MP, M = 2 H;
18-MPA(Pd), M = Pd

The steps in the above synthetic route are as follows:

1000 mg of compound 1, chlorin e6, was dissolved in dimethylformamide (DMF) to a concentration of 0.1 M, and added with 1043 µL of methyl iodide and 4633 mg of anhydrous potassium carbonate. The reaction was carried out under stirring for 2 hours, added with dichloromethane (DCM) for dilution, and then washed with water. Then, the organic phase was collected, concentrated, and subjected to 200-300 mesh silica gel column chromatography (eluted with ethyl acetate/dichloromethane=1:100) to obtain 962 mg of compound 10 with a yield of 90%.

800 mg of compound 10 and 675 µL of p-methoxystyrene were dissolved in dichloromethane (DCM) to a concentration of 0.03 M, and then added with 319 mg of Grubbs' catalyst. The reaction was performed under reflux for 20 hours and then filtered, and the obtained filtrate was transferred to a separating funnel, and washed with water for several times. The organic phase was collected, concentrated, and subjected to 200-300 mesh silica gel column chromatography (eluted with ethyl acetate/dichloromethane=1:100) to obtain 654 mg of compound 11-MP with a yield of 70%.

500 mg of compound 11-MP was dissolved in dichloromethane (DCM) to a concentration of 0.1 M, and then added with 79 mg of palladium acetate. The reaction was heated to reflux for 5 hours, and then washed with water, and the organic layer was collected, concentrated, and subjected to 200-300 mesh silica gel column chromatography (eluted with petroleum ether/acetone=5:1) to obtain 490 mg of metal complex 12-MP(Pd) with a yield of 86%.

400 mg of compound 11-MP and metal complex 12-MP(Pd) were respectively dissolved in tetrahydrofuran (THF) and 1M KOH aqueous solution (v:v=1:1) to a concentration of 0.05 M. The reaction was carried out under stirring for 4 hours, concentrated at reduced pressure to remove THF, added with water and adjusted to pH 5-6 to precipitate a solid, which was then filtered to obtain 350 mg of compound 13-MP and 345 mg of compound 14-MP(Pd), which were directly used for the next step without separation.

The above compound 13-MP and compound 14-MP(Pd) were respectively dissolved in dimethylformamide (DMF) to a concentration of 0.1 M, and then added in sequence with 170 mg of 1-ethyl-3(3-dimethylpropylamine) carbodiimide (EDCI), 318 mg of aspartic acid methyl ester hydrochloride, 452 µL of $Et_3N$ and 466 µL of N,N-diisopropylethylamine (DIEA). The reaction was carried out under stirring for 1 hour, and then added gradually with formic acid aqueous solution to precipitate a solid. The obtained residue was filtered and subjected to 200-300 mesh silica gel column chromatography (eluted with methanol/dichloromethane=1:20) to obtain 215 mg of compound 15-MPA and 210 mg of compound 16-MPA(Pd).

200 mg of compounds 15-MPA and 16-MPA(Pd) were respectively dissolved in acetone to a concentration of 0.03 M, and added with an equal volume of 0.5 N NaOH aqueous solution. The reaction was carried out under stirring for 10 hours, and then added with anhydrous ethanol to precipitate a solid, which was filtered to obtain 180 mg of compound 17-MPA and 175 mg of compound 18-MPA(Pd), both of which are soluble in water.

Compound 17-MPA: $C_{45}H_{43}N_5Na_4O_{10}$, MW:=905.2601. $^1$H NMR (400 MHz, DMSO-d6) δ8.58 (m, 1H), 8.21 (m, 1H), 8.09 (m, 1H), 7.98 (m, 2H), 7.71 (m, 1H), 7.54 (m, 2H), 7.44 (m, 1H), 6.70 (s, 1H), 5.32 (m, 2H), 4.62 (m, 1H), 4.55 (m, 1H), 4.38 (m, 1H), 3.66 (m, 2H), 3.52 (s, 6H), 3.36 (m, 2H), 3.20 (s, 3H), 2.71 (m, 1H), 2.58 (m, 2H), 2.40 (m, 2H), 2.18 (m, 2H), 1.73 (d, J=7.0 Hz, 3H), 1.61 (m, 4H), −1.81 (1H, s), −2.10 (1H, s). HRMS (ESI) m/z: $C_{45}H_{46}N_5O_{10}$[M−4Na−H]$^-$, calculated value: 816.3250, measured value: 816.3255.

Example 4: Effect of Compound 17-MPA on Colorectal Cancer and Colorectal Cancer Metastasis The sonodynamic therapy with water-soluble chlorin derivative 17-MPA synthesized in Example 3 as a sonosensitizer was evaluated on tumor-bearing mice suffering from hepatic metastasis of colorectal cancer in ultrasound field.

The water-soluble chlorin derivative 17-MPA was dissolved in normal saline to prepare a drug solution for administration. In this protocol, Balb/c (female, 18-22 g) mice were injected with CT26 mouse colorectal carcinoma cells into the hemispleen to construct a model of mouse suffering from hepatic metastasis of hemisplenic colorectal cancer. The body weight of the mice was recorded from the 7$^{th}$ day of tumor injection, and measured every other day. The mice with liver cancer were randomly divided into 4 groups: (1) control group (saline alone), (2) administration (17-MPA) group, (3) ultrasound group (ultrasound alone), (4) administration+ultrasound (17-MPA+ultrasound) group, (5) control drug group (Talaporfin sodium, a drug for photodynamic therapy). On the 12$^{th}$ day of tumor injection, the mice were injected with 16 mg/kg of 17-MPA via tail vein, and subjected to ultrasound radiation of 1.88 W/cm$^2$ for 30 minutes after 4 hours. The administration and ultrasonic treatment were continued, with three days as one course of treatment. The second and third courses of treatment were performed on 17$^{th}$ and 22$^{th}$ days, respectively. The effect of compound 17-MPA-mediated sonodynamic therapy (SDT) on tumors deep in animals was evaluated.

Figure 3:
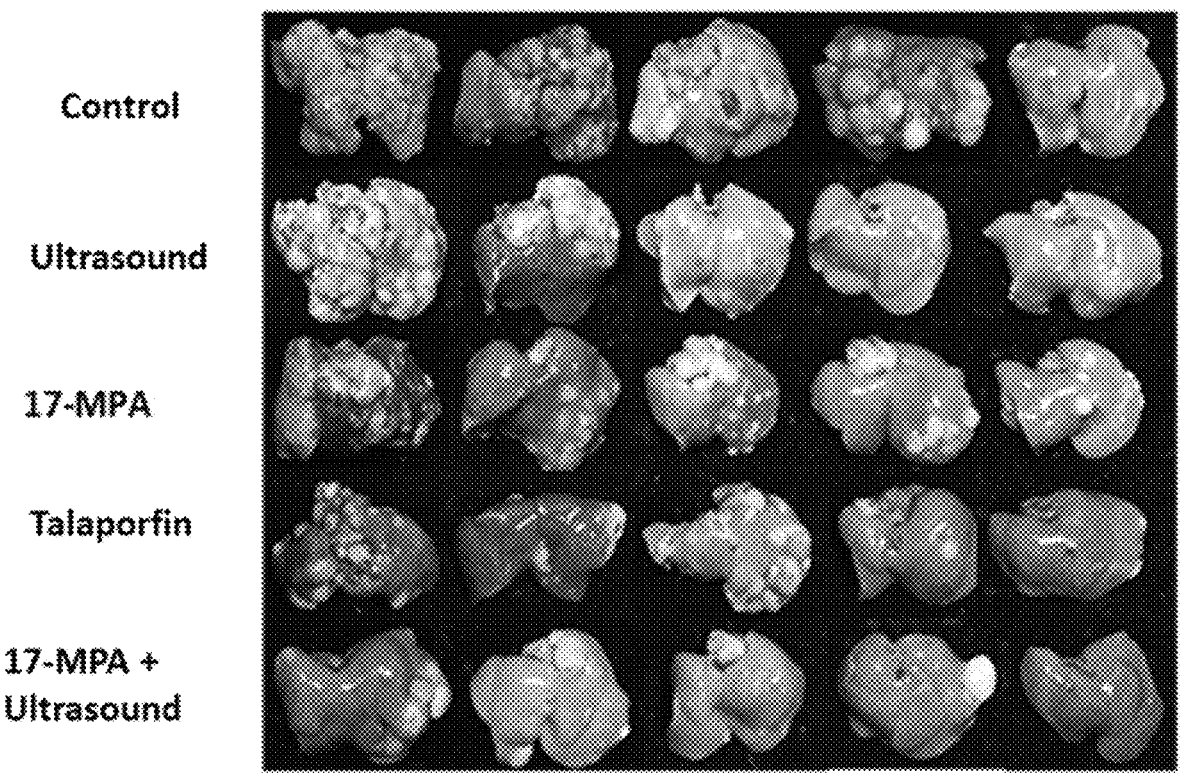
FIG. 3 is a photograph showing the inhibitory effect of compound 17-MPA according to the present disclosure and the ultrasonic treatment, alone or in combination, on hepatic metastasis of colon cancer tumor.

It can be seen from FIG. 3 that the mice in the control group and the ultrasound group developed a large number of macroscopic hepatic metastasis of tumors, the mice in the administration (17-MPA) group have slightly reduced tumor tissues, and the mice in the administration+ultrasound (17-MPA+ultrasound) group possessed significantly reduced metastatic lesions.

Figure 4:
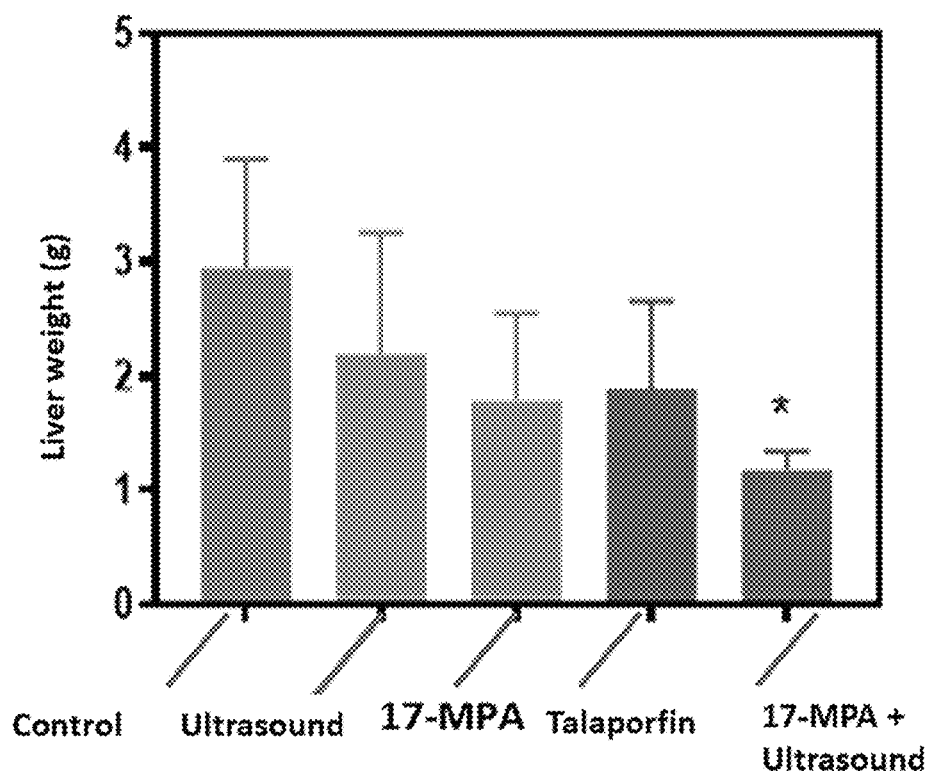
FIG. 4 is a bar graph showing the effect of compound 17-MPA according to the present disclosure and the ultrasonic treatment, alone or in combination, on liver weight of mice (*$P<0.01$~$0.001$).

FIG. 4 shows the average weight of liver tissue in mice of the groups. It can be seen from FIG. 4 that the mice in the 17-MPA+ultrasound group had a significantly lower average weight of liver tissue than that of the control group, and also that of the administration group, the ultrasound group, and the control drug group.

From the above experiments, it can be seen that compound 17-MPA can be used in combination with ultrasound for sonodynamic therapy to effectively reduce and/or cure colon cancer metastasis.

Example 5. Experimental Study on the Pharmacokinetics of Compound 17-MPA

High performance liquid chromatography was used to study the pharmacokinetic properties of compound 17-MPA in SD rats and the distribution of 17-MPA in ICR tumor-bearing mice, so as to provide basis for the timing for continuous administration in pharmacodynamics study and the intervention timing of sonodynamic and photodynamic therapy.

The inter-day and intra-day precision and stability (in terms of room temperature storage, low temperature storage, and repeated freezing and thawing) for detection of plasma samples with high performance liquid chromatography method was determined. In the inter-day and intra-day precision experiments and stability experiments on plasma samples, the precision as obtained was less than 15%, and the accuracy was within ±20%. The extraction recoveries of 17-MPA at the high, medium, low and lowest lower limit of detection concentration in plasma were 65.89±2.38%, 69.71±0.22%, 74.39±1.13% and 80.73±0.35%, respectively. The extraction recovery of the internal standard was 68.10±0.99%. According to the established quantitative analysis method, the drug concentration in the plasma of SD rats after tail vein injection was detected, and the pharmacokinetic compartment model of 17-MPA in SD rats was determined to conform to the two-compartment model, and the distribution half-life (t1/2α) was 0.627±0.256 h, and the elimination half-life (t1/2β) was 7.421±0.802 h. In addition, the equilibrium dialysis method was used to determine the binding rate of DYSP-C07 to the plasma protein of SD rats, and finally it was found that the binding rates of DYSP-C07 at high, medium and low concentrations to the plasma proteins of SD rats were 90.94±1.90%, 92.25±1.40%, and 95.78±1.20%, respectively. 17-MPA was detected in the heart, liver, spleen, lung, kidney and tumor tissues of ICR tumor-bearing mice, in which 17-MPA showed high concentration in liver and kidney tissues, and gradually accumulated in tumor tissues and maintained a higher concentration from 6 h to 12 h.

Through pharmacokinetics experiments, it was verified that the pharmacokinetic of compound 17-MPA in SD rats conformed to the two-compartment model. The compound bound to plasma proteins of SD rats in a high amount, accumulated in the liver and kidney of the ICR tumor-bearing mice in a relatively high degree, and showed a tendency of gradual accumulation in tumor tissues. Finally, a high performance liquid chromatography/ultraviolet detection method was established which can be used in the study on the pharmacokinetics and tissue distribution of 17-MPA in mice after intravenous injection. According to the obtained pharmacokinetics data, it was recommended to use elimination half-life of compound 17-MPA as the reference starting point of the time for light irradiation treatment, so as to conduct a systematic pharmacodynamics evaluation of compound 17-MPA.

The mice were administered 16 mg/kg of compound 17-MPA via tail vein, and detected for the distribution of compound 17-MPA in various tissues of ICR mice and the concentration of compound 17-MPA in the tissues in the periods from 1 h to 12 h. The results were as follows:

1 h: kidney>lung>spleen, heart>tumor, liver;
2 h: liver>kidney>lung, heart, spleen>tumor;
4 h: liver>kidney>lung, heart, spleen, tumor;
6 h: liver>kidney>tumor, lung, spleen, heart;
8 h: liver>kidney>spleen, tumor, heart, lung;
12 h: liver>kidney>tumor, lung, spleen, heart.

Example 6: Preparation of Compounds 25-tFPL and 26-tFPL(Pd)

The synthetic routes of compounds 25-tFPL and 26-tFPL(Pd) are as follows:

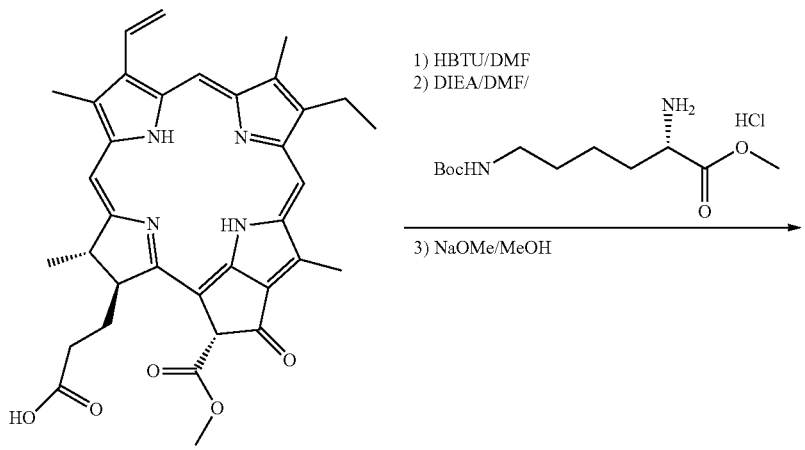

19

-continued
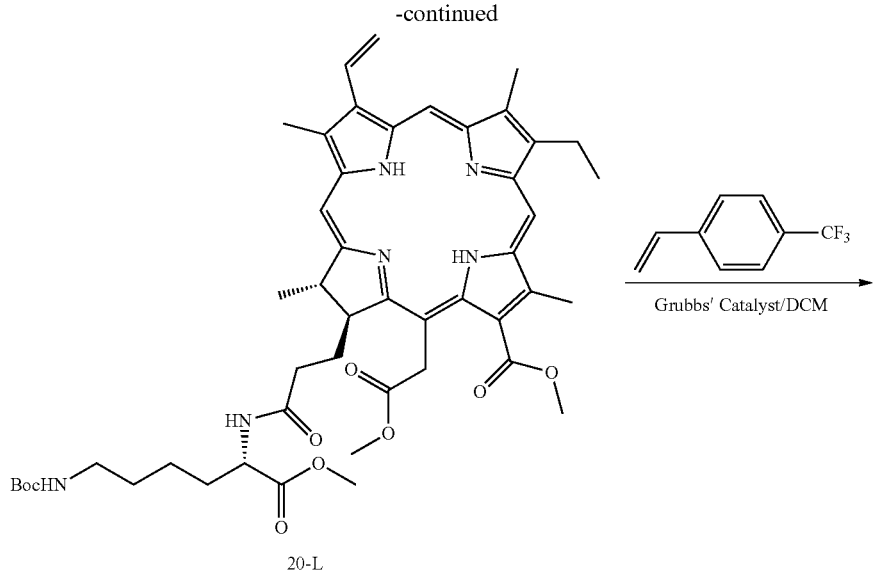
20-L
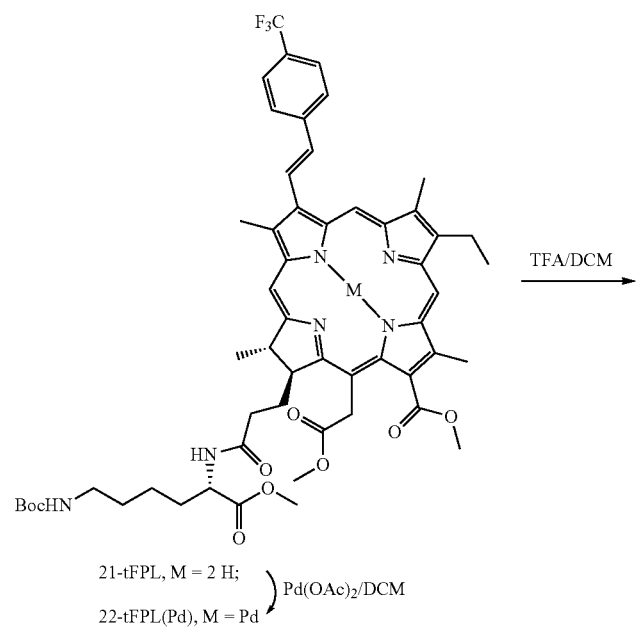
21-tFPL, M = 2 H;
22-tFPL(Pd), M = Pd  } Pd(OAc)₂/DCM
TFA/DCM →

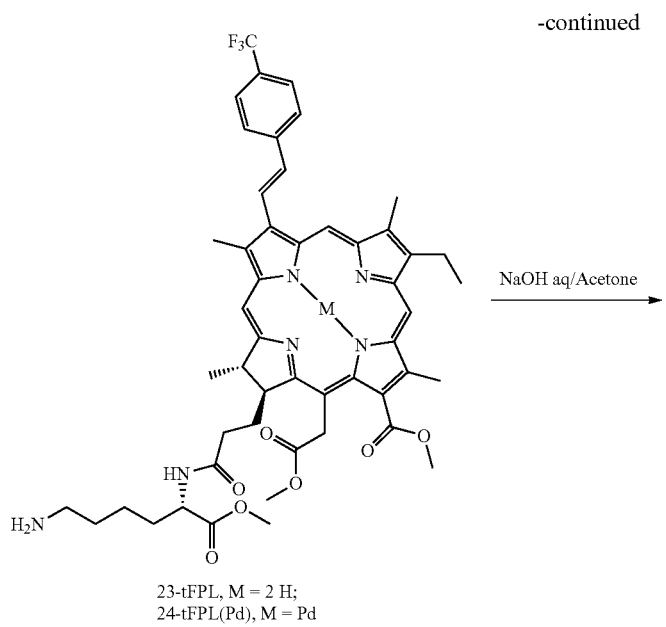 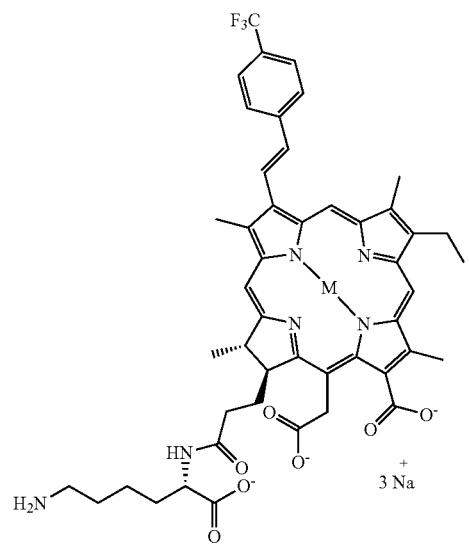

23-tFPL, M = 2 H;
24-tFPL(Pd), M = Pd 25-tFPL, M = 2 H;
26-tFPL(Pd), M = Pd

The steps in the above synthetic route are as follows.

500 mg of compound 19 as raw material was dissolved in dimethylformamide (DMF) to a concentration of 0.1 M, and then added with 479 mg of o-benzotriazole-1-yl-N,N,N',N'-tetramethyluronium hexafluorophosphate (HBTU) and 220 μL of N,N-diisopropylethylamine (DIEA). The reaction was carried out under stirring for 0.5 hour, and then added with 393 mg of lysine methyl ester hydrochloride and 293 μL of N,N-diisopropylethylamine (DIEA). The reaction continued for 1 hour, then diluted with dichloromethane (DCM), washed with water, and concentrated. The resulting residue was dissolved in 1% sodium methoxide/methanol solution, stirred for 8 hours, adjusted to pH 6-7, and then concentrated at reduced pressure. The obtained residue was dissolved in dichloromethane (DCM), and washed with water, and the organic phase was collected, concentrated, and subjected to 200-300 mesh silica gel column chromatography (eluted with methanol/dichloromethane=1:15) to obtain 550 mg of compound 20-L with a yield of 85%.

400 mg of compound 20-L and 1540 μL of p-trifluoromethylstyrene were dissolved in dichloromethane (DCM) to a concentration of 0.03 M, and then added with 133 mg of Grubbs' catalyst. The reaction was performed under reflux for 24 hours and then filtered, and the obtained filtrate was transferred to a separating funnel, and washed with water for several times. The organic phase was collected, concentrated, and subjected to 200-300 mesh silica gel column chromatography (eluted with methanol/dichloromethane=1:15) to obtain 309 mg of compound 21-tFPL with a yield of 65%.

200 mg of compound 21-tFPL was dissolved in DCM to a concentration of 0.1 M, and added with 79 mg of palladium acetate. The reaction was heated to reflux for 5 hours, and then washed with water. The organic layer was collected, concentrated, and subjected to 200-300 mesh silica gel column chromatography (eluted with petroleum ether/acetone=3:1) to obtain 205 mg of metal complex 22-tFPL (Pd) with a yield of 93%.

200 mg of compound 21-tFPL and 22-tFPL(Pd) were dissolved in 3 mL of dichloromethane (DCM), respectively, and added with 1 mL of trifluoroacetic acid (TFA). Then the reaction was carried out under stirring for 1 h, and then concentrated to dryness at reduced pressure to obtain 190 mg of compound 23-tFPL and 185 mg of compound 24-tFPL(Pd) crude product (TFA salt), respectively.

150 mg of compound 23-tFPL and compound 24-tFPL (Pd) were dissolved in acetone, respectively, to a concentration of 0.03 M, and then added with an equal volume of 0.5 N NaOH aqueous solution. The reaction was carried out under stirring for 5 hours, and then added with anhydrous ethanol to precipitate a solid, which was then filtered to obtain 140 mg of compound 25-tFPL and 143 mg of water-soluble compound 26-tFPL(Pd), respectively.

Compound 26-tFPL(Pd): $C_{47}H_{46}F_3N_6Na_3O_7Pd$, MW=1038.2108: $^1$H NMR (400 MHz, DMSO-d$_6$) δ 8.72 (d, J=16.6 Hz, 1H), 8.06 (d, J=7.5 Hz, 2H), 8.03 (s, 1H), 7.29 (s, 1H), 7.82 (d, J=16.6 Hz, 1H), 7.58 (t, J=7.5 Hz, 2H), 7.45 (m, 1H), 5.28 (m, 2H), 4.60 (m, 1H), 3.77 (q, J=7.5 Hz, 2H), 3.57 (s, 3H), 3.53 (s, 3H), 3.51 (m, 2H), 3.28 (s, 3H), 3.15 (m, 4H), 3.07 (m, 1H), 2.59 (m, 1H), 2.46 (m, 1H), 2.12 (m, 2H), 1.71 (d, J=7.1 Hz, 3H), 1.65 (t, J=7.5 Hz, 3H), 1.57 (m, 2H), 1.33 (m, 4H). HRMS (ESI) m/z: $C_{47}H_{46}F_3NsNa_2O_7Pd$ [M−Na]$^-$, calculated value: 1015.2216, measured value: 1015.2221.

Example 7. Effect of Compound 26-tFPL(Pd) on Liver Cancer (1) Experiment on Survival Rate of Cancer Cells In Vitro:

In this experiment, CHC (chlorin e6) was used as a control compound, and the MTT method was used to evaluate the dark toxicity and phototoxicity of compound 26-tFPL(Pd) on HepG2 cells. Particularly, HepG2 cells were cultured in DMEM medium supplemented with 10% (v/v) fetal bovine serum (FBS), 100 IU·mL$^{-1}$ penicillin and 100 mg·mL$^{-1}$ streptomycin, and were seeded in a 96-well plate at a density of $5\times10^3$ cells/well. Before the experiment, the cells were cultured in an incubator at 37° C. and 5% $CO_2$ for 24 hours. The drugs at different concentrations (0-25 μM) were evaluated for dark toxicity. The cells were added with different doses of chlorin e6 (CHC) and compound 26-tFPL (Pd) and determined for the survival rates immediately after 24 hours by 3-(4,5-dimethylthiazol-2-yl)-2,5-diphenyl tetrazolium-ammonium bromide (MTT) spectrophotometry in triplicate. The evaluation of phototoxicity of the drugs at different concentrations (0-25 μM) was similar to the evaluation of dark toxicity. Particularly, after being incubated with the drug for 24 hours, the cells were irradiated with LED light having a wavelength of 660 nm and a light intensity of 1.7 J·cm$^{-2}$ for 10 min. 2 hours after treatment, the cells were determined for the survival rates by MTT method in triplicate.

Figure 5:
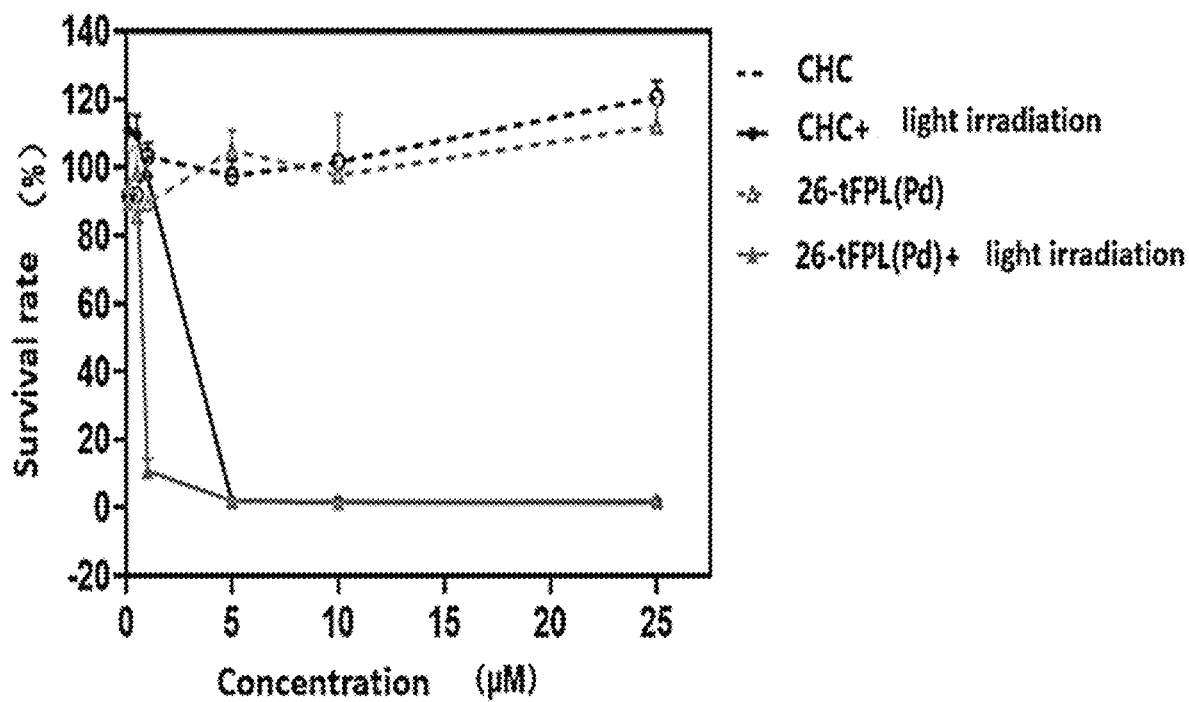
FIG. 5 shows the effect of compound 26-tFPL(Pd) according to the present disclosure and CHC, with or without light irradiation, on cell survival.

FIG. 5 shows the cell survival after the treatment of compound 26-tFPL(Pd) according to the present disclosure and CHC, respectively, with or without light irradiation. The results showed that in the absence of light irradiation, when compound 26-tFPL(Pd) was 0-25 μM, the cell survival rate was above 80%. In the presence of light irradiation (1.7 J·cm$^{-2}$, 660 nm, 10 min), compound 26-tFPL(Pd) had increased treatment efficacy with the increased concentration. When the concentration was 1 μM, the cell survival rate under the treatment with compound 26-tFPL(Pd) and light irradiation was only 10%, while the cell survival rate under the treatment with CHC was still above 80%. The above data shows that compound 26-tFPL(Pd) as a photosensitizer can effectively kill cancer cells under light irradiation.

(2) Measurement of Intracellular Singlet Oxygen ($^1O_2$):

After co-cultured with compound 26-tFPL(Pd), HepG2 cells were irradiated with LED light at a wavelength of 660 nm for 0, 1, 3, 5 and 10 minutes (660 nm, 25 mW·cm$^{-2}$), Lanthanide rare earth fluorescent probe ATTA-EU3+, which can produce long-lived fluorescent signal with larger stokes shift after combining with intracellular $^1O_2$, was used. $^1O_2$ level in living cells was detected with time-resolved fluorescence.

Figure 6:
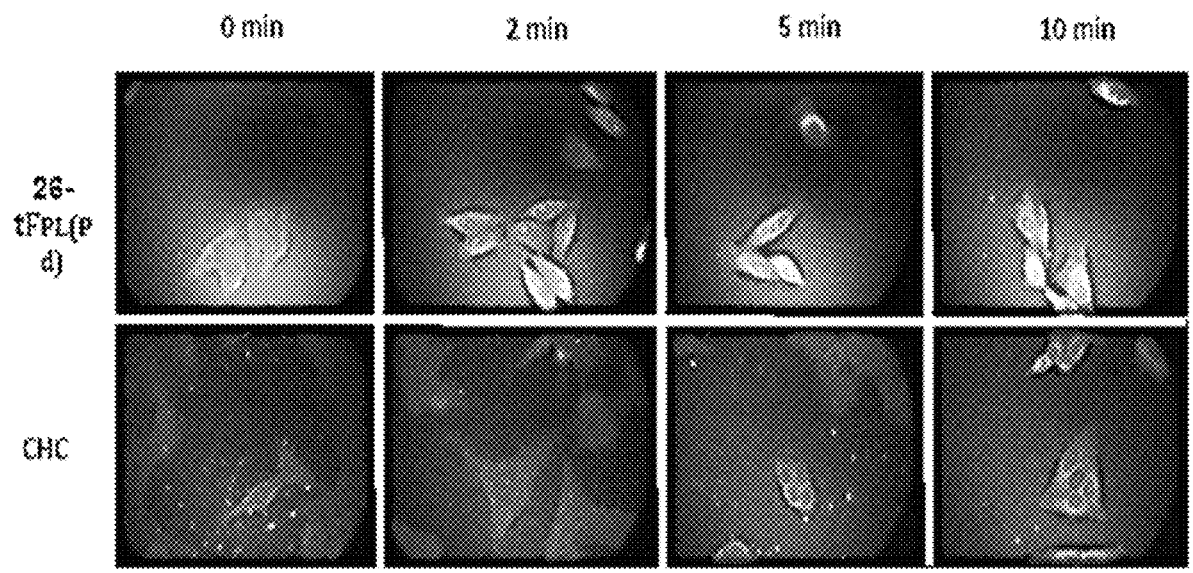
FIG. 6 is an image showing intracellular singlet oxygen ($^1O_2$) generated in the presence of the backbone molecule chlorin (CHC) and compound 26-tFPL(Pd) according to the present disclosure.

FIG. 6 shows the experimental results of the measurement of intracellular singlet oxygen ($^1O_2$). It can be seen from FIG. 6 that compound 26-tFPL(Pd) had a significantly higher yield of $^1O_2$ in cells in comparison with the original molecular backbone CHC.

(2) Photodynamic Therapy for Tumor-Bearing Mice:

H22 mouse hepatoma cell line was cultured in vitro, and then 3×10$^5$ H22 cells were injected into the right back of ICR male mice. On the eighth day of injection (the tumor grew to 200 mm$^3$), photodynamic therapy was performed.

The water-soluble chlorin derivative 26-tFPL(Pd) was dissolved in normal saline to prepare a drug solution for administration. The mice were randomly divided into four groups, namely the control group, the administration (26-tFPL(Pd)) group, the light irradiation group, and the administration (26-tFPL(Pd))+light irradiation group (PDT group). Mice in the PDT group were subjected to light irradiation treatment 4 hours after injection via tail vein (8 mg·kg$^{-1}$), the intensity of light radiation is 20 mW·cm$^{-2}$, the time for light irradiation is 5 min, and the final amount for light radiation is 6 J·cm$^{-2}$. The control group was untreated. The administration (26-tFPL(Pd)) group had the same dose as the PDT group, and the light irradiation group had the same light irradiation intensity and time as the PDT group. After treatment, the body weight and tumor volume of mice in the groups were recorded.

Figure 7:
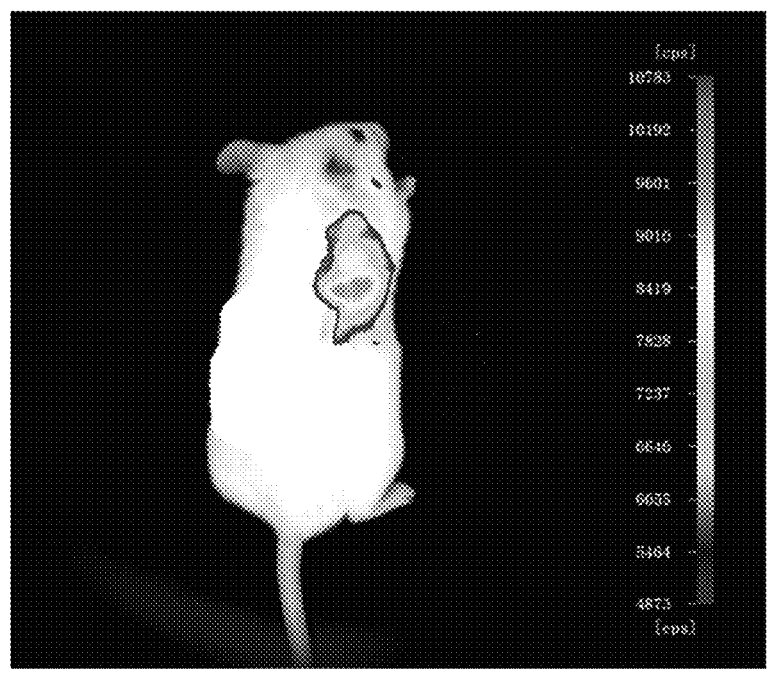
FIG. 7 is a fluorescence imaging of a tumor site after intravenous injection of compound 26-tFPL(Pd) according to the present disclosure.

After mice were injected with compound 26-tFPL(Pd) via tail vein, the fluorescence imaging of the tumors with compound 26-tFPL(Pd) enriched was acquired by a live animal optical imaging instrument (NightOWL II LB983). FIG. 7 shows an example of the fluorescence imaging.

Figure 8:
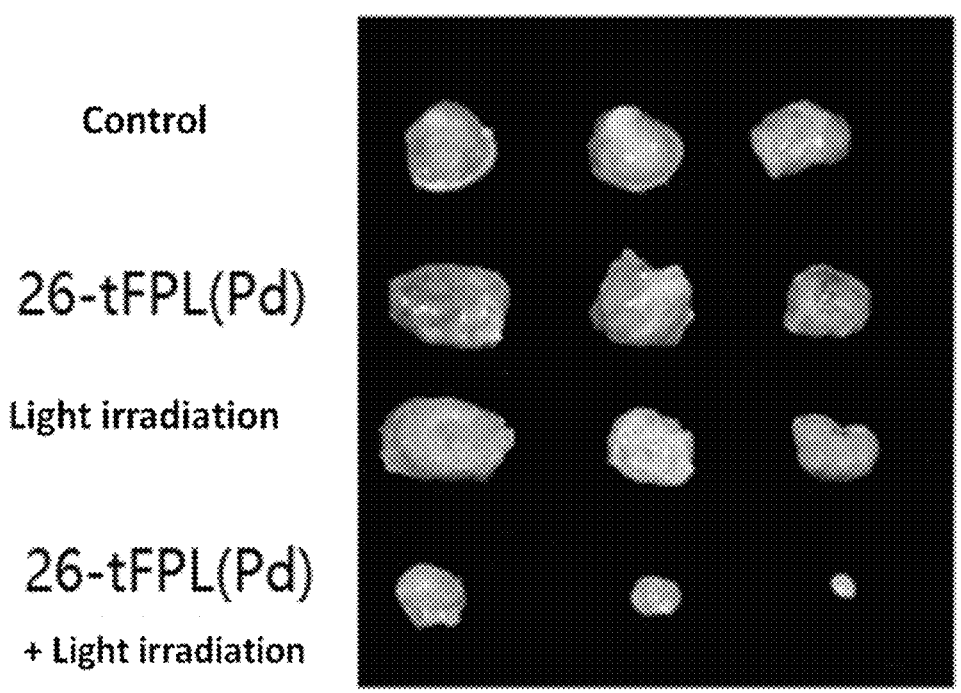
FIG. 8 is a photograph showing the effect of compound 26-tFPL(Pd) according to the present invention and the light irradiation, alone or in combination, on tumor volume in mice.
Figure 9:
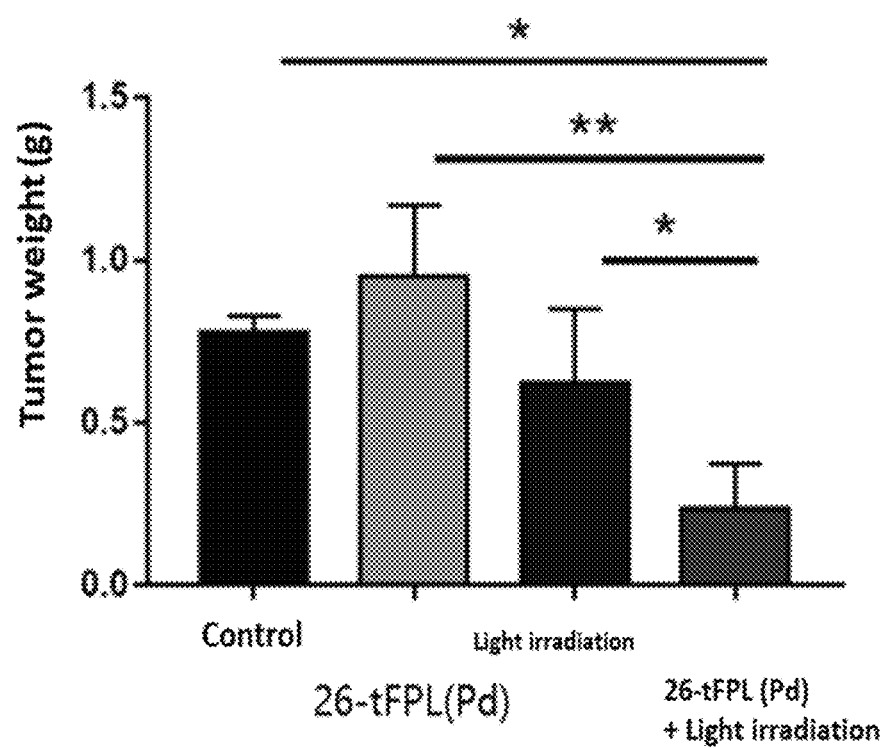
FIG. 9 a bar graph showing the effect of compound 26-tFPL(Pd) according to the present invention and the light irradiation, alone or in combination, on the weight of tumor ($p<0.05$(*), $p<0.005$(**) and $p<0.05$(*)).

FIG. 8 shows the changes in tumor volume in the control group, the administration (26-tFPL(Pd)) group, the light irradiation group, and the 26-tFPL(Pd)+light irradiation group. It can be seen from FIG. 8 that the 26-tFPL(Pd)+light irradiation group had significantly reduced tumor volume compared with the control group, the administration group, and the light irradiation group. As shown in FIG. 9, the statistical difference analysis showed that, after treatment, there was a significant difference in tumor weight between the 26-tFPL(Pd)+light irradiation group and the other groups: the 26-tFPL(Pd)+light irradiation group had a statistical significance of $p<0.05$ versus the control group, $p<0.05$ versus the light irradiation group, and $p<0.005$ versus the administration group.

Example 8: Ultrasonic Medical System

Figure 10:
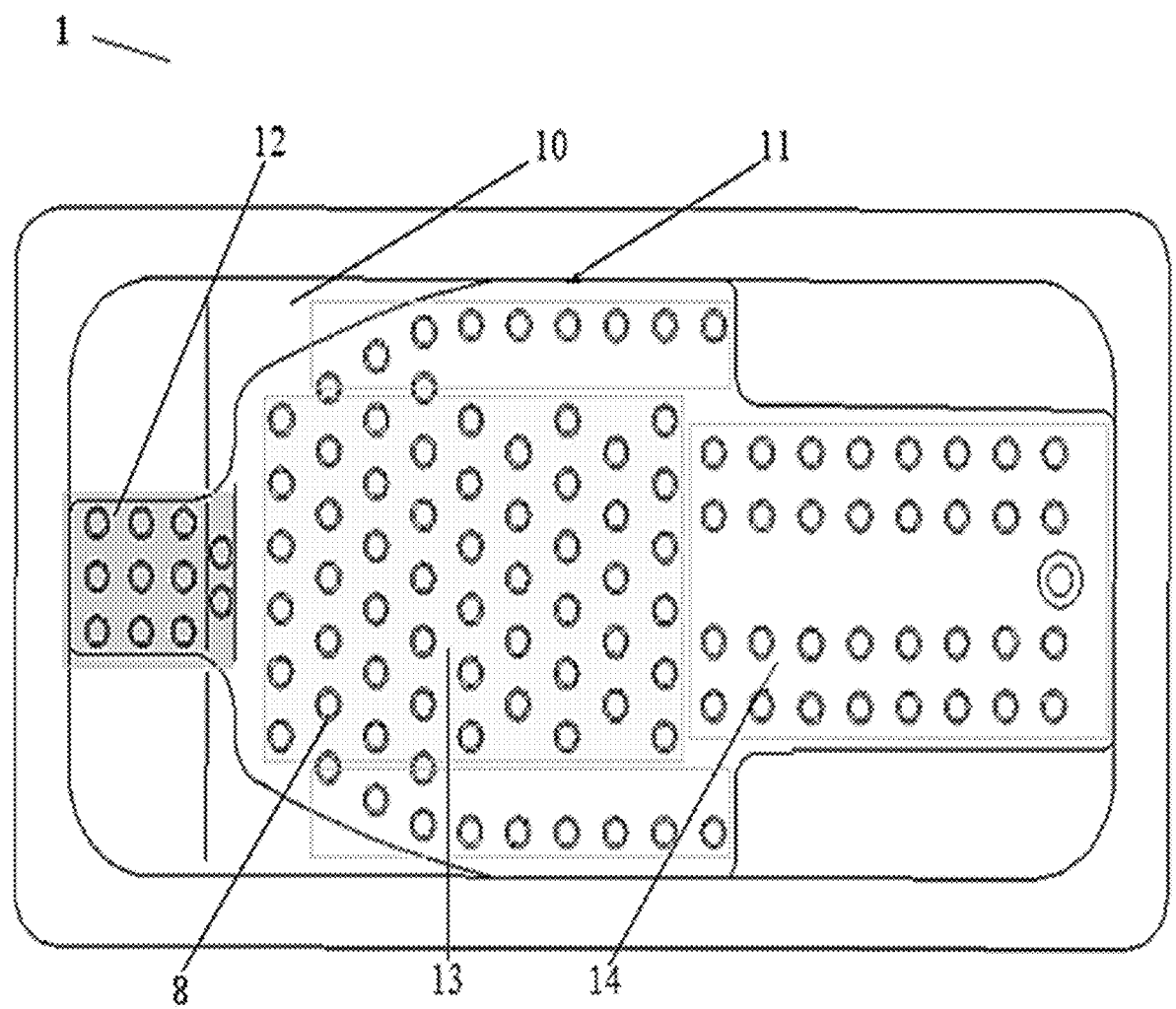
FIG. 10 shows a top view of a transducer ultrasonic bed 1 according to an embodiment of the present disclosure.

FIG. 10 shows a top view of a transducer ultrasonic bed 1 according to an embodiment of the present disclosure. As shown in FIG. 10, the transducer ultrasonic bed 1 comprises a bottom 10 and a wall 11 extending upward from the bottom 10. The bottom 10 is divided into three regions, namely the head region 12, the trunk region 13 and the limbs region 14, according to the shape of the human body, and a number of ultrasonic transducers 8 are arranged in the three regions, respectively. Although FIG. 10 shows a particular number of ultrasonic transducers 8, this is only for the purpose of illustration, and is not intended to limitation. Based on the required treatment effect and the mechanical strength of the transducer ultrasonic bed 1, the number of ultrasonic transducers 8 arranged in the regions can be increased or decreased. Preferably, 127 ultrasonic transducers 8 are uniformly arranged in the bottom 10. In addition, the bottom 10 of the transducer ultrasonic bed 1 shown in FIG. 10 is a flat shape in which the trunk region 13 and limbs region 14 are slightly lower than other regions, but the bottom of other shapes (such as concave, curved, or even wavy shape) that is well known to those skilled in the art and allows the patient to lie and receive ultrasonic radiation thereon is also suitable. Although not shown in the figure, the bottom of the transducer ultrasonic bed 1 may also have a recess corresponding to the shape of the human body, so that the human body can be accommodated therein. In this case, a plurality of ultrasonic transducers 8 as mentioned above are preferably arranged in the recess.

Figure 11:
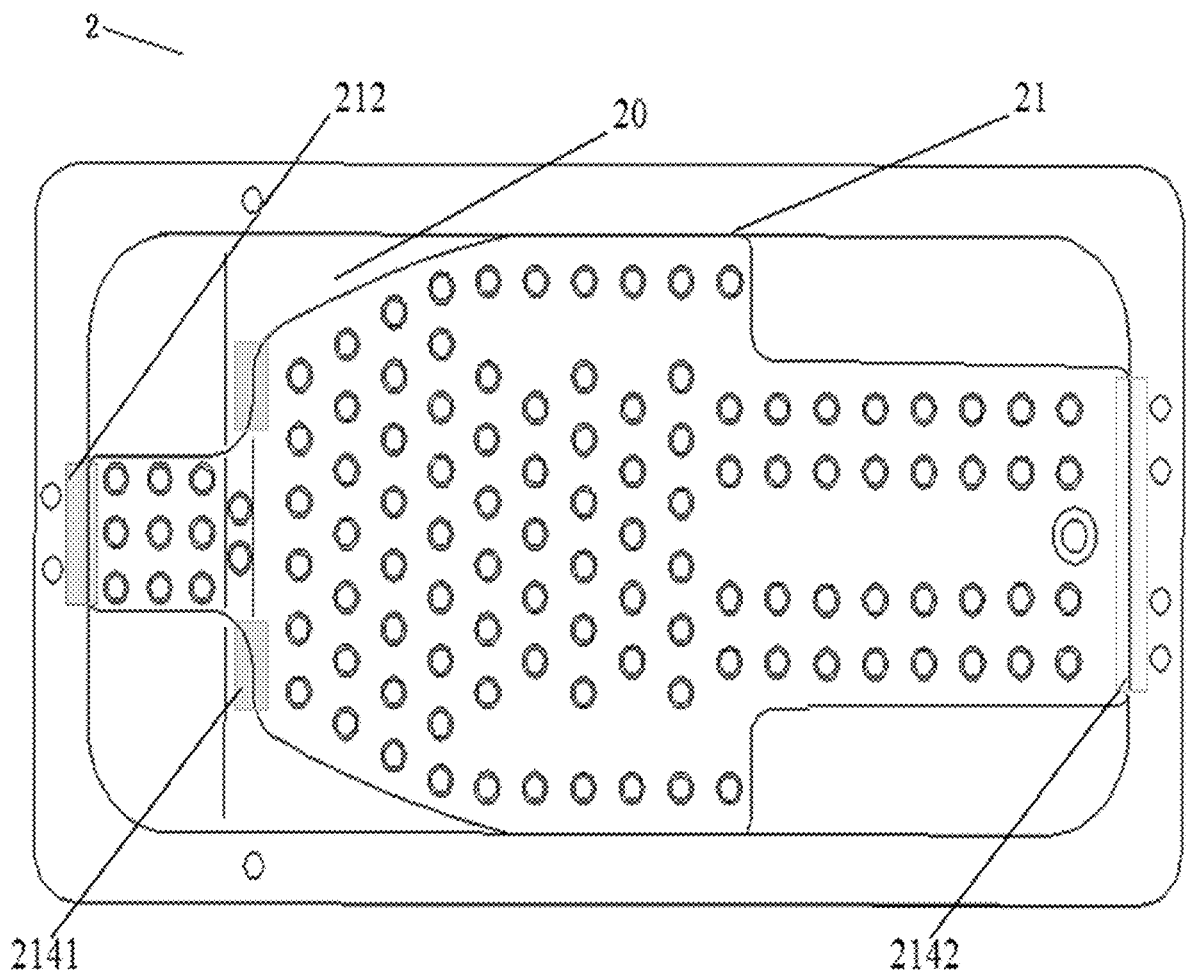
FIG. 11 shows a top view of a transducer ultrasonic bed 2 according to another embodiment of the present disclosure.

FIG. 11 shows a top view of a transducer ultrasonic bed 2 according to another embodiment of the present disclosure. As shown in FIG. 11, the transducer ultrasonic bed 2 comprises a bottom 20 and a wall 21 extending upward from the bottom 20. Both the bottom 20 and the wall 21 are arranged with ultrasonic transducers 8. The arrangement and shape of the bottom 20 are the same as those of the bottom 10 in FIG. 10, and thus will not be repeated for the sake of brevity. According to the shape of the human body, the wall 21 may be divided into three regions, namely the above-head region 212, the shoulders region 2141, and below-foot region 2142. A number of ultrasonic transducers 8 are arranged in the three regions, respectively. Although FIG. 11 shows the particular number of ultrasonic transducers 8, this is only for illustrative purposes, and is not intended to limitation. Based on the required treatment effect and the mechanical strength of the transducer ultrasonic bed 2, the number of ultrasonic transducers 8 arranged in these regions may be increased or decreased. Preferably, the number of ultrasonic transducers 8 arranged in the above-head region 212, the shoulders region 2141, and the below-foot region 2142 are 2, 2 and 4, respectively.

It should be noted that although the transducer ultrasonic beds shown in FIGS. 10 and 11 is in a bathtub form of basically rectangular shape, the transducer ultrasonic bed can also be in other shapes, such as an oval shape and the like. The wall of the transducer ultrasonic bed may have an inclination angle varied relative to the vertical direction, and may also be in various shapes such as a curved-surface shape. These variations should be considered to be within the scope of the present disclosure.

Figure 12:
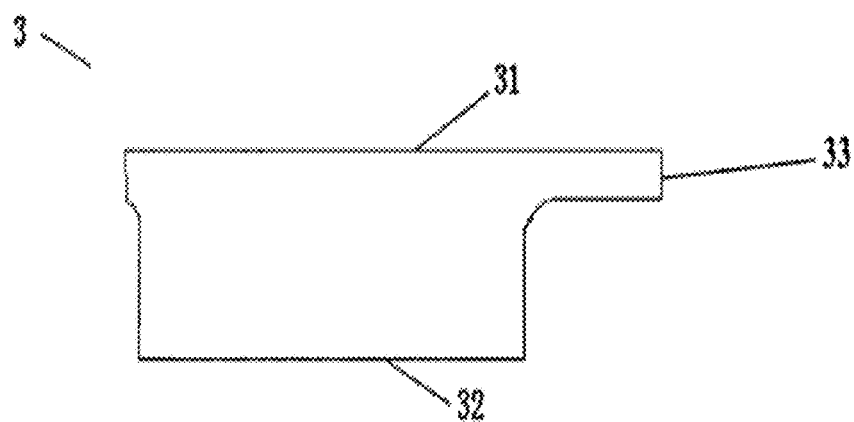
FIG. 12 shows a side view of a transducer module assembly 3 according to an embodiment of the present disclosure.

FIG. 12 shows a side view of a transducer module assembly 3 according to an embodiment of the present disclosure. As shown in FIG. 12, the transducer module assembly 3 comprises an upper surface 31 and a lower surface 32. The upper surface 31 is provided with a cooling fan, and the side 33 is used to connect with a fixing device. The fixation means can be any means that is well-known in the art and suitable for fixing the transducer module assembly 3. A number of ultrasonic transducers 8 are arranged in the lower surface 32. Based on the required treatment effect and the mechanical strength of the transducer module assembly 3, the number of arranged ultrasonic transducers 8 may be increased or decreased. Preferably, 28 ultrasonic transducers 8 are uniformly arranged in the lower surface 32.

Although the transducer module assembly 3 shown in FIG. 12 is a structure of rectangular shape and has a flat lower surface 32, it should be understood that the transducer module assembly is not limited to such structure and shape, and it may also has a structure of gate shape and has a lower surface of arc-shape or other shape.

Figure 13:
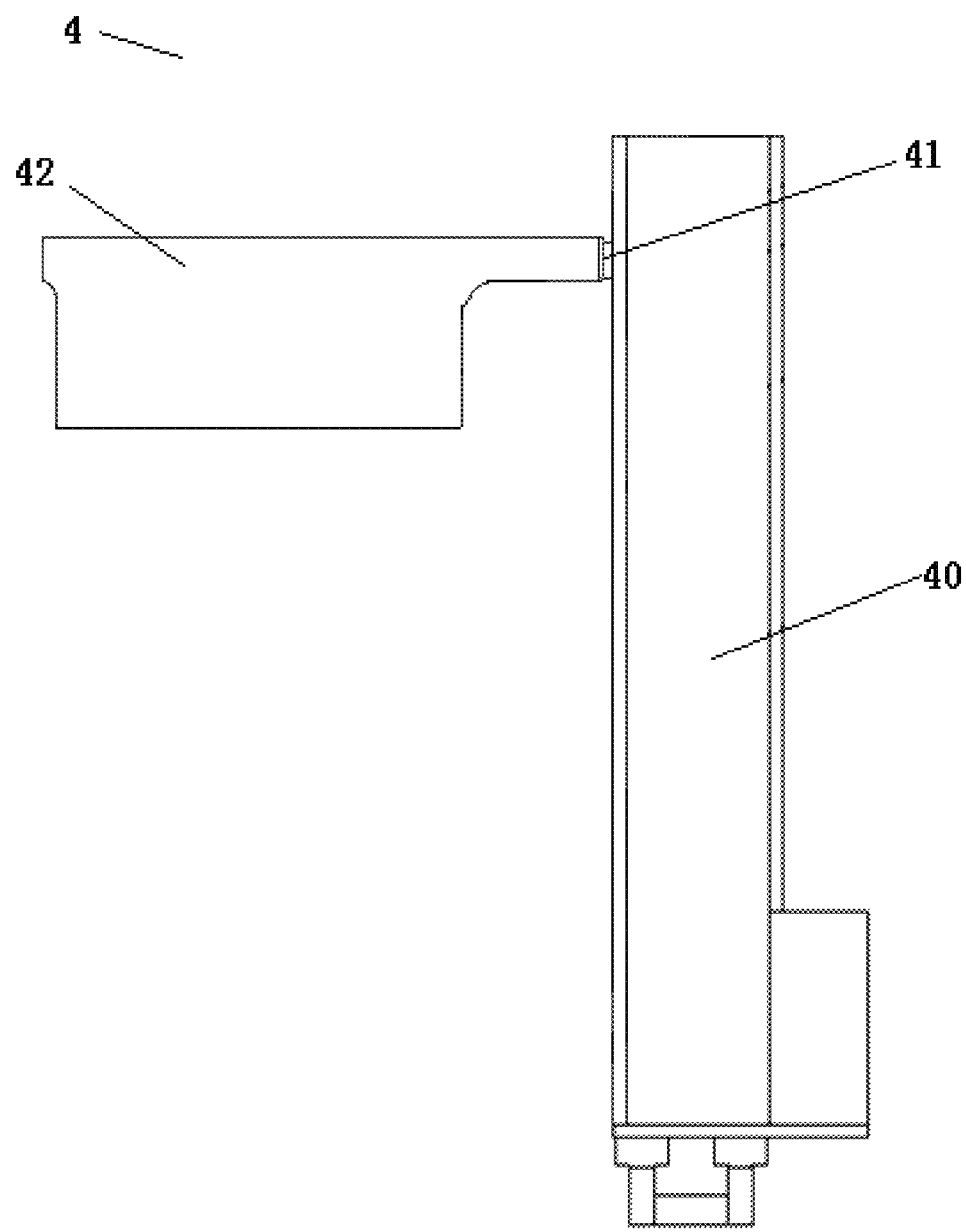
FIG. 13 shows a side view of a transducer module assembly 4 with a two-dimensional numerically controlled motion device according to another embodiment of the present disclosure.

FIG. 13 shows a side view of a transducer module assembly 4 with a two-dimensional numerically controlled motion device 40 according to another embodiment of the present disclosure. As shown in FIG. 13, the two-dimensional numerically controlled motion device 40 is connected to the transducer module 42 through a cantilever 41 mounted thereon. During operation, the transducer module 42 can move along the X axis and the Y axis under the control of the two-dimensional numerically controlled motion device 40. Here, the X axis refers to an axis extending in a horizontal direction parallel to the longitudinal direction of the transducer ultrasonic bed, and the Y axis refers to an axis extending in a vertical direction perpendicular to the horizontal plane of the transducer ultrasonic bed. In the exemplary embodiment, the shape of the transducer module 42 and the arrangement of the ultrasonic transducers 8 are the same as those of the transducer module assembly 3 shown in FIG. 12, and thus will not be repeated for the sake of brevity.

It should be pointed out that although the transducer module 42 shown in FIG. 13 only moves longitudinally along the transducer ultrasonic bed in the horizontal direction, the transducer module 42 can be designed to move laterally along the transducer ultrasonic bed, according to the need, for example, when the lateral size of the transducer ultrasonic bed is relatively large, or when multiple subjects are treated at the same time. At this time, the two-dimensional numerically controlled motion device 40 will be replaced by a three-dimensional numerically controlled motion device.

Figure 14:
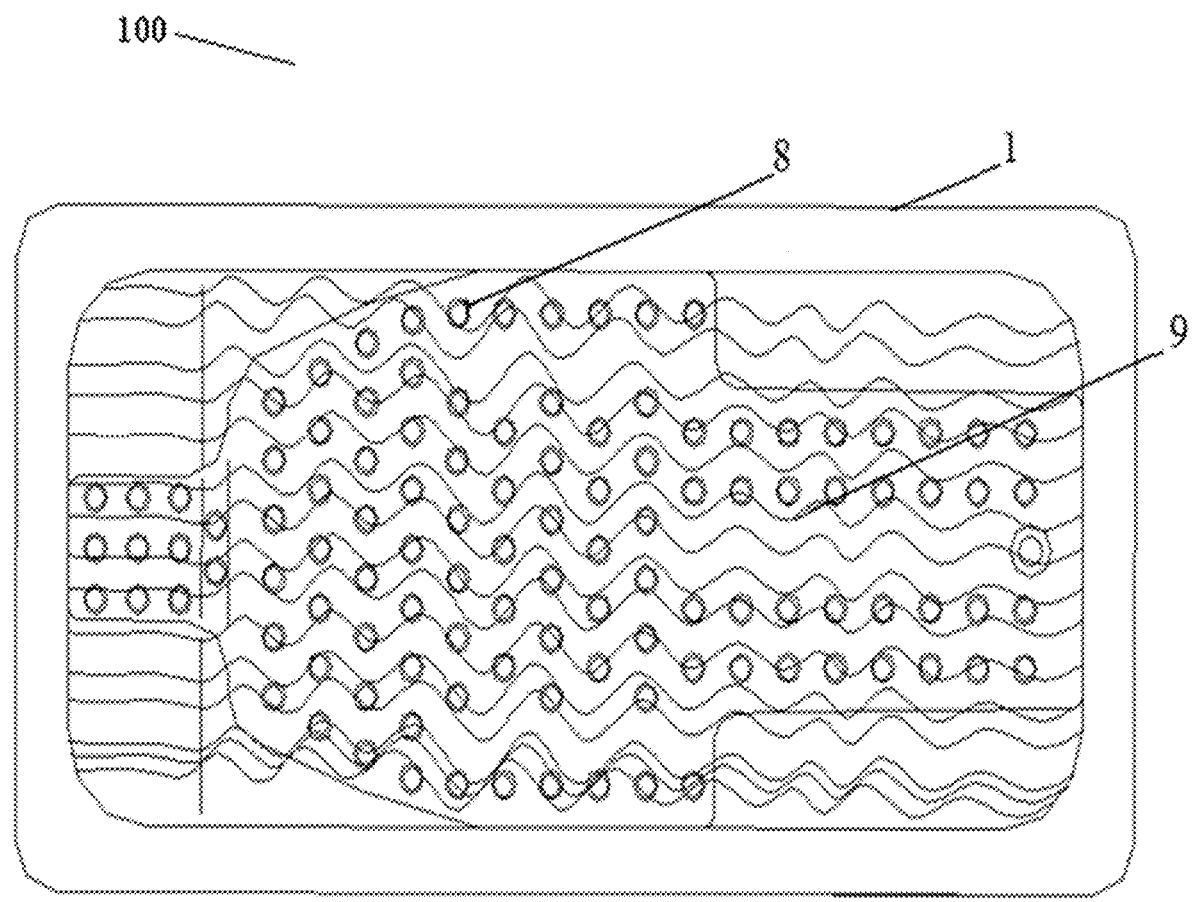
FIG. 14 shows a top view of an ultrasonic medical system 100 according to an embodiment of the present disclosure.

FIG. 14 shows a top view of an ultrasonic medical system 100 according to an embodiment of the present disclosure. As shown in FIG. 14, the ultrasonic medical system 100 comprises a transducer ultrasonic bed 1 and a contact agent 9, and ultrasonic transducer 8 is immersed in the contact agent 9. The contact agent 9 may be a coupling substance (contact agent) whose acoustic resistance is between that of the ultrasonic transducer 8 and that of the human tissue to form an acoustic interface, and may be water, vacuum degassed (cold, hot) water and the like. Preferably, vacuum degassed (cold, hot) water is used. Since the transducer ultrasonic bed 1 has been described in detail above, it will not be repeated for the sake of brevity. Alternatively, the transducer ultrasonic bed 1 may be replaced by the transducer ultrasonic bed 2.

Figure 15:
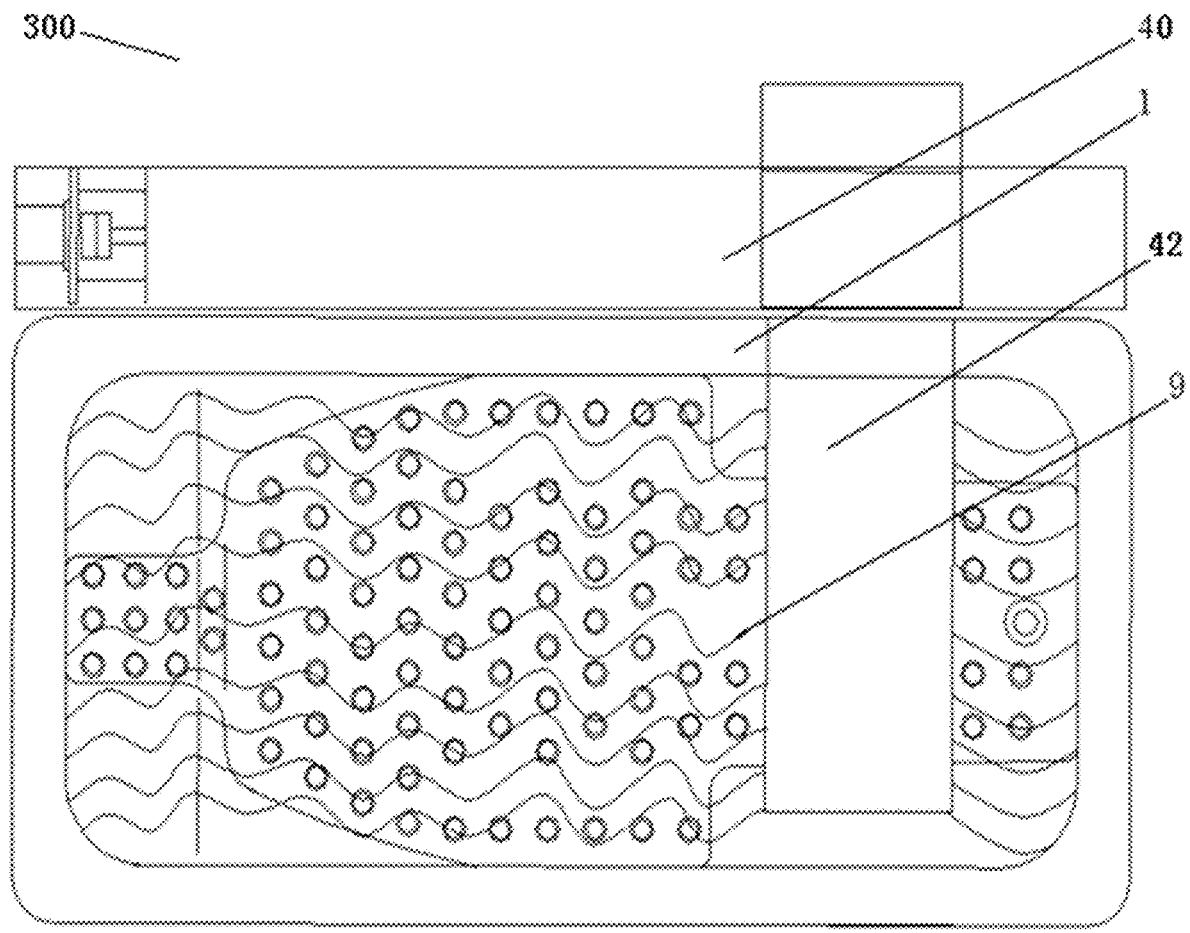
FIG. 15 shows a top view of an ultrasonic medical system 300 according to another embodiment of the present disclosure.

FIG. 15 shows a top view of an ultrasonic medical system 300 according to another embodiment of the present disclosure. As shown in FIG. 15, the ultrasonic medical system 300 comprises a transducer ultrasonic bed 1, a transducer module assembly 4 and a contact agent 9, wherein a transducer module 42 is located above the transducer ultrasonic bed 1, and the ultrasonic transducer 8 is immersed in the contact agent 9. The transducer ultrasonic bed 1, the transducer module assembly 4 and the contact agent 9 have been described in detail above, and thus will not be repeated for the sake of brevity. Alternatively, the transducer ultrasonic bed 1 may be replaced by the transducer ultrasonic bed 2; or the transducer module assembly 4 may be replaced by the transducer module assembly 3, or both two may be replaced.

Figure 16:
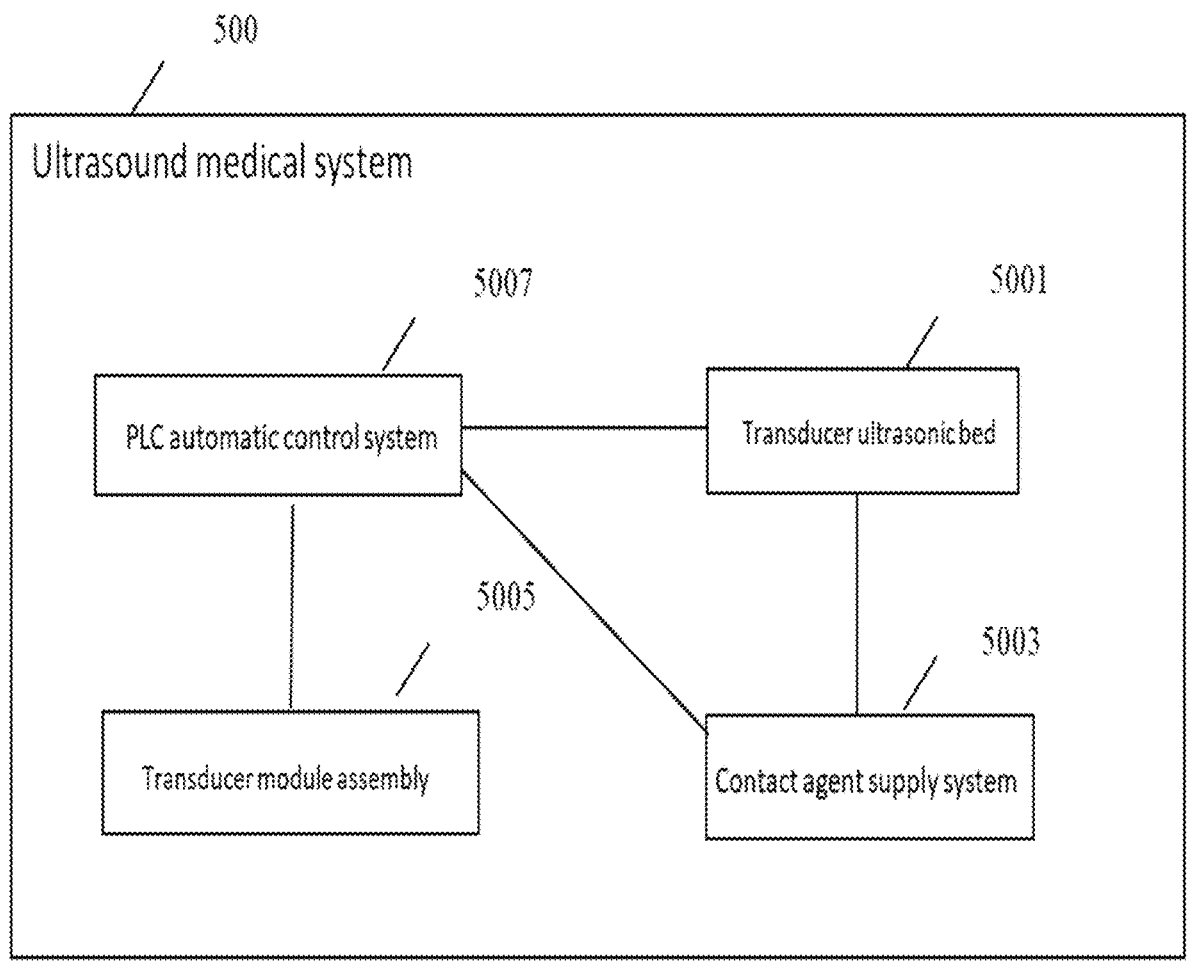
FIG. 16 shows a block diagram of an ultrasonic medical system 500 with a PLC automatic control system according to yet another embodiment of the present disclosure.

FIG. 16 shows a block diagram of an ultrasonic medical system 500 with a PLC automatic control system according to yet another embodiment of the present disclosure. As shown in FIG. 16, the ultrasonic medical system 500 comprises a transducer ultrasonic bed 5001, a contact agent supply system 5003, a transducer module assembly 5005, and a PLC automatic control system 5007. The PLC automatic control system 5007 is connected to the transducer ultrasonic bed 5001, the contact agent supply system 5003 and the transducer module assembly 5005, respectively, to control the cooperative work of the later three according to the treatment need. The contact agent supply system 5003 is connected to the transducer ultrasonic bed 5001 so that the contact agent 9 can be supplied to the transducer ultrasonic bed 5001 under the control of the PLC automatic control system 5007. The connection may be a wired connection or a wireless connection. The transducer ultrasonic bed 5001 may be the transducer ultrasonic bed 1 or 2, or may be any other suitable variant of the transducer ultrasonic bed 1 or 2. The transducer module assembly 5005 may be the transducer module assembly 3 or assembly 4, or may be any other suitable variant of the transducer module assembly 3 or 4.

Figure 22:
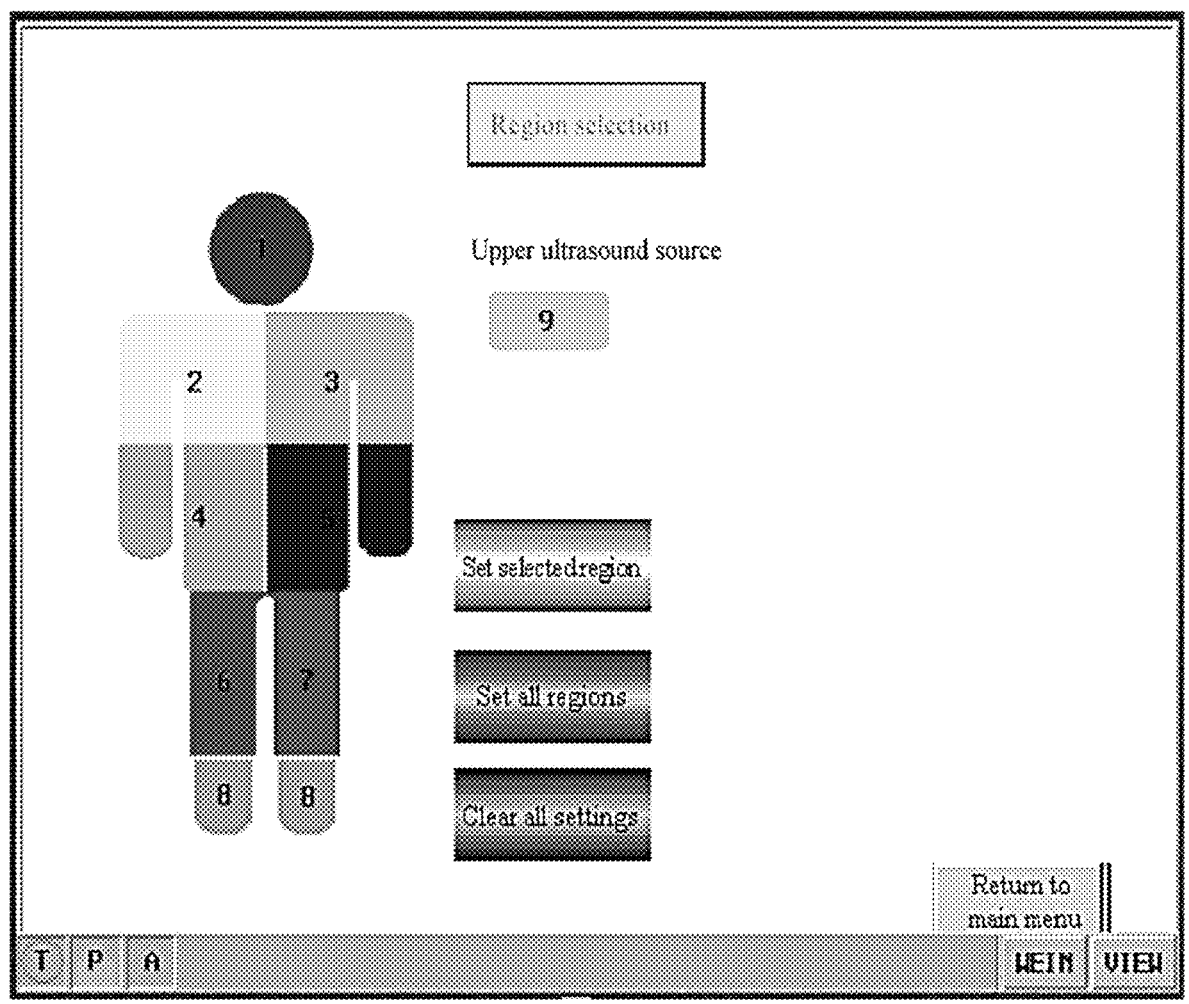
FIG. 22 shows a human-computer interface for selecting patient's region for treatment of the PLC automatic control system according to the present disclosure.
Figure 23:
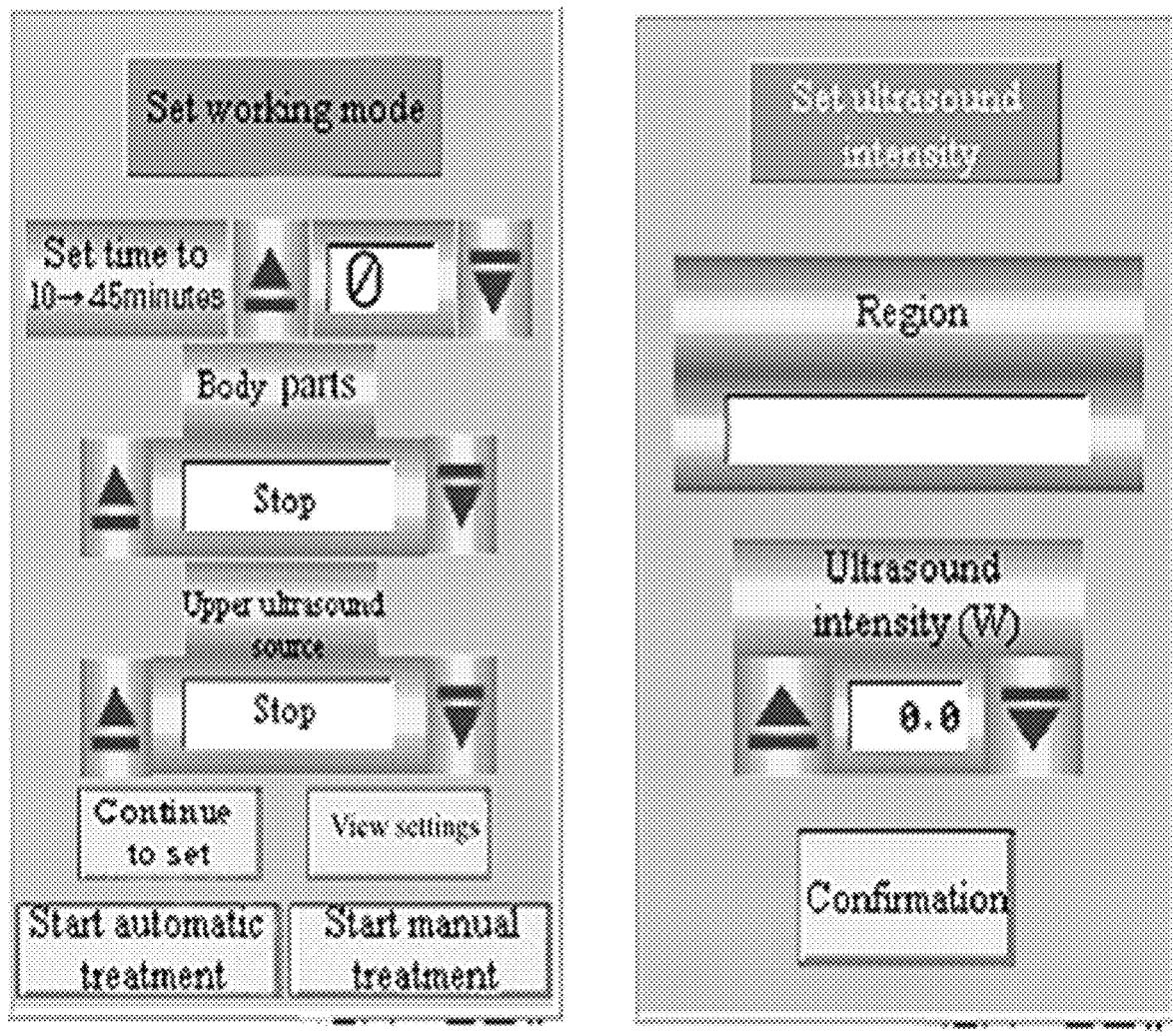
FIG. 23 shows a human-computer interface showing the working mode and the setting of ultrasound intensity of the PLC automatic control system according to the present disclosure.
Figure 24:
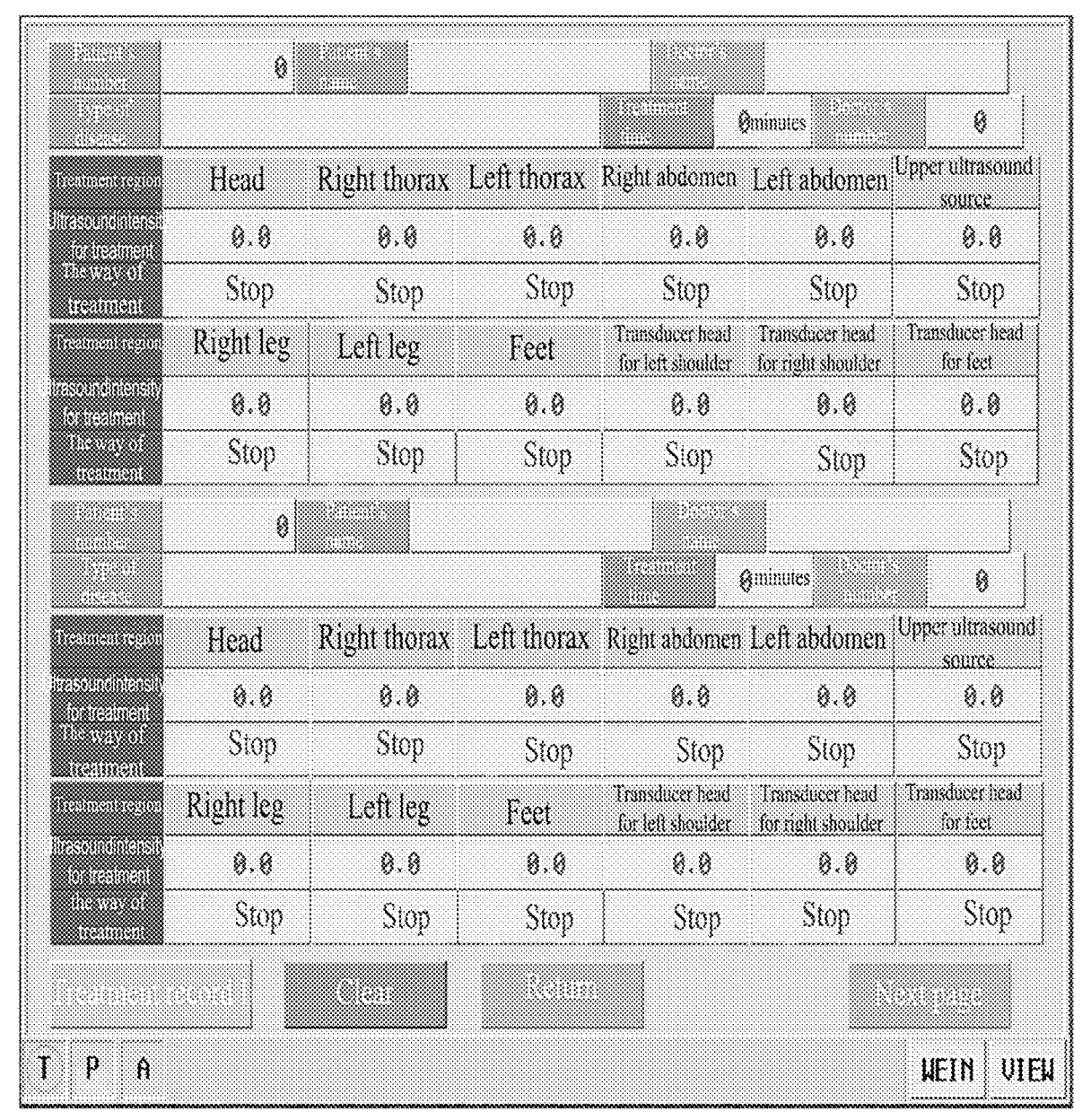

Preferably, the PLC automatic control system 5007 further comprises a monitoring system 5008 (not shown). The monitoring system 5008 comprises a monitor 5009, such as a 10.4 touch screen, for displaying the working parameters of at least some of the ultrasonic transducers in the transducer ultrasonic bed and in the transducer module assembly. The working parameters may be options for the treatment regions of the patient as shown in FIG. 22, and working mode and the setting of ultrasound intensity as shown in FIG. 23. More preferably, the monitor 5009 can also display lesion information in the human body. The lesion information may be a therapeutic regimen for patient as shown in FIG. 24, so that the treatment parameters can be changed at any time during the treatment according to the patient's feelings, to achieve the best curative effect.

Figure 17:
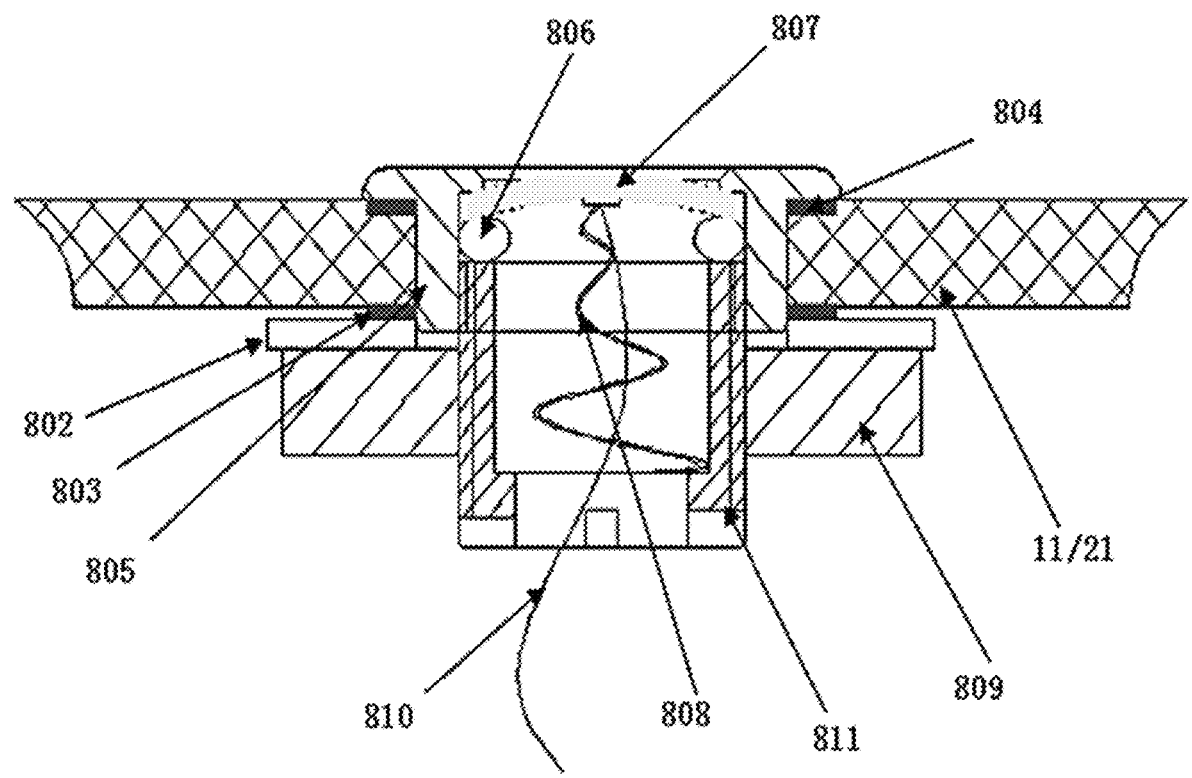
FIG. 17 shows a transducer head of an ultrasonic transducer 8 according to an embodiment of the present disclosure.

FIG. 17 shows a transducer head of an ultrasonic transducer 8 according to an embodiment of the present disclosure. As shown in FIG. 17, a wafer 807 is put into the inner cavity of a wafer base, the outer spherical surface of the wafer is in close contact with the inner cavity surface of the wafer base, and a conductor and a limit position are formed between the two. An O-type rubber ring 806 is put on the inner surface of the wafer. After a compression spring 808 with a wire 810 welded on the upper part is put into the inner hole for fastening a copper bolt 811, and the copper bolt 811 is tightened with a wafer base 805. The assembled wafer base 805 is put into the reserved round hole of the transducer head on the wall 11 or 21 of the transducer ultrasonic bed 1 or 2, and a rubber flat washer 804 is put between the two. The copper bolt 811 has the function of connecting to and fixing the transducer sound bed 1 or 2, and after putting sealing rubber ring 803 and flat washer 802 on it, the round nut 809 is screw into the copper bolt 811 to fasten the transducer head to the wall 11 or 21 of the transducer sound bed 1 or 2.

The various components of the ultrasound medical system are described in detail above, and the specific working flow of the ultrasound medical system will be described by way of examples.

Figure 18:
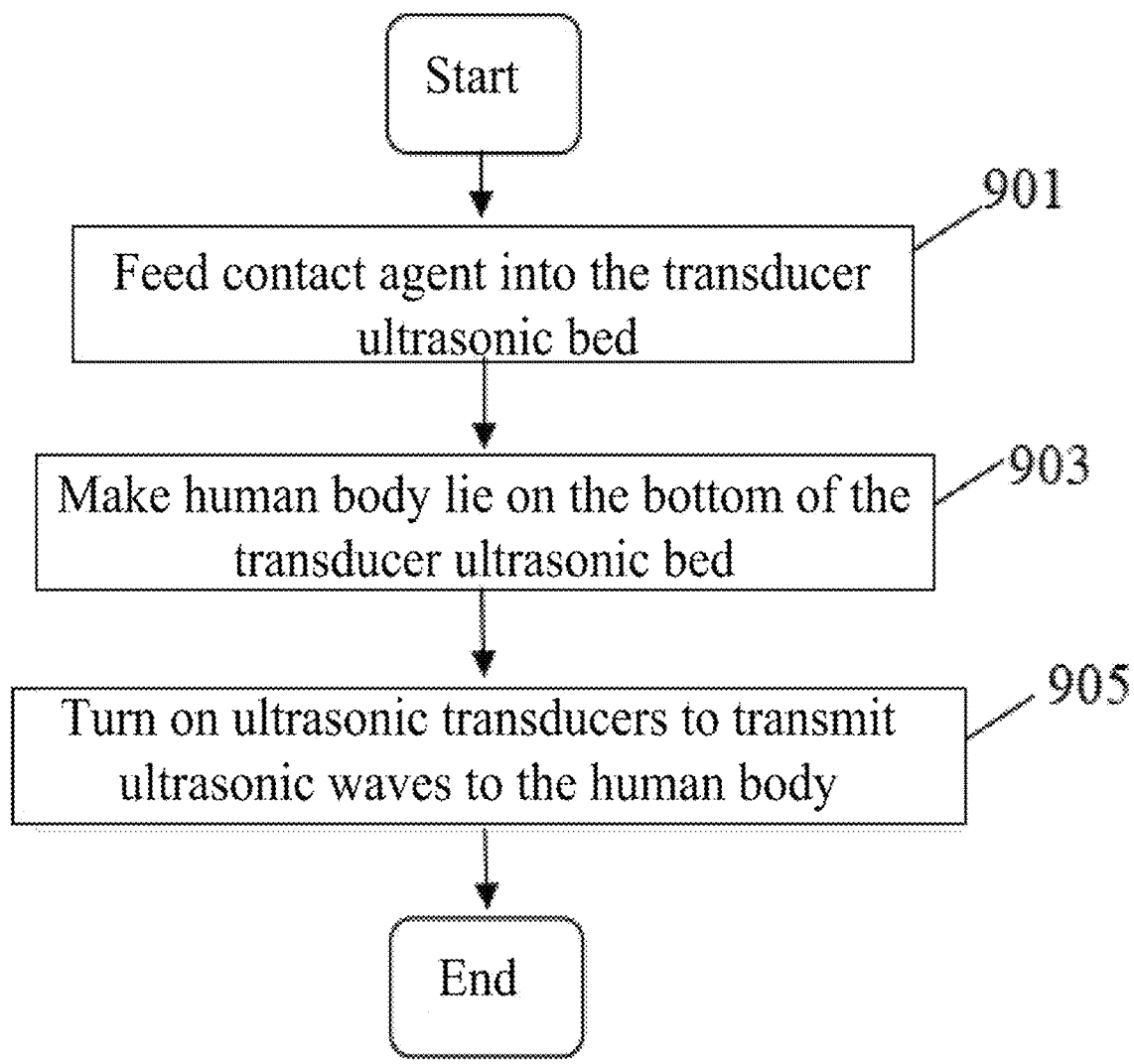
FIG. 18 shows a working flow chart of an ultrasonic medical system 100 according to an embodiment of the present disclosure.

FIG. 18 shows a working flow chart of an ultrasonic medical system 100. As shown in FIG. 18, in step 901, the contact agent is fed into the transducer ultrasonic bed, so that all the ultrasonic transducers in the transducer ultrasonic bed are immersed in the contact agent. In step 903, the human body is made lie on the bottom of the transducer ultrasonic bed. In step 905, the ultrasonic transducers are turned on to transmit ultrasonic waves to the human body. The intensity of the ultrasonic waves should be within the range that the human body can bear and can effectively excite the sonosensitizer. For example, the ultrasound intensity can be set in the range of 0.1-3 $W/cm^2$ at an interval of 0.1 $W/cm^2$, such as 0.1, 0.2, 0.3 . . . , 1.0, 1.1, 1.2 . . . , 2.5, 2.6, 2.7, 2.8, 2.9, 3.0 $W/cm^2$, and the waveform is continuous wave or pulse wave. Preferably, enough contact agent is fed into the transducer ultrasonic bed, so that the human body can float in it, and a slight lateral drift thus occurs. The floatation and lateral drift can make the human body receive more intensive ultrasonic irradiation in the transducer ultrasonic bed. Preferably, the contact agent is vacuum degassed (cold, hot) water. Preferably, the transmitted ultrasonic wave is a pulse wave at a frequency of 0.3 MHz to 3 MHz. Preferably, the ultrasonic waves are simultaneously transmitted to the human body from the wall and the bottom of the transducer ultrasonic bed.

Figure 19:
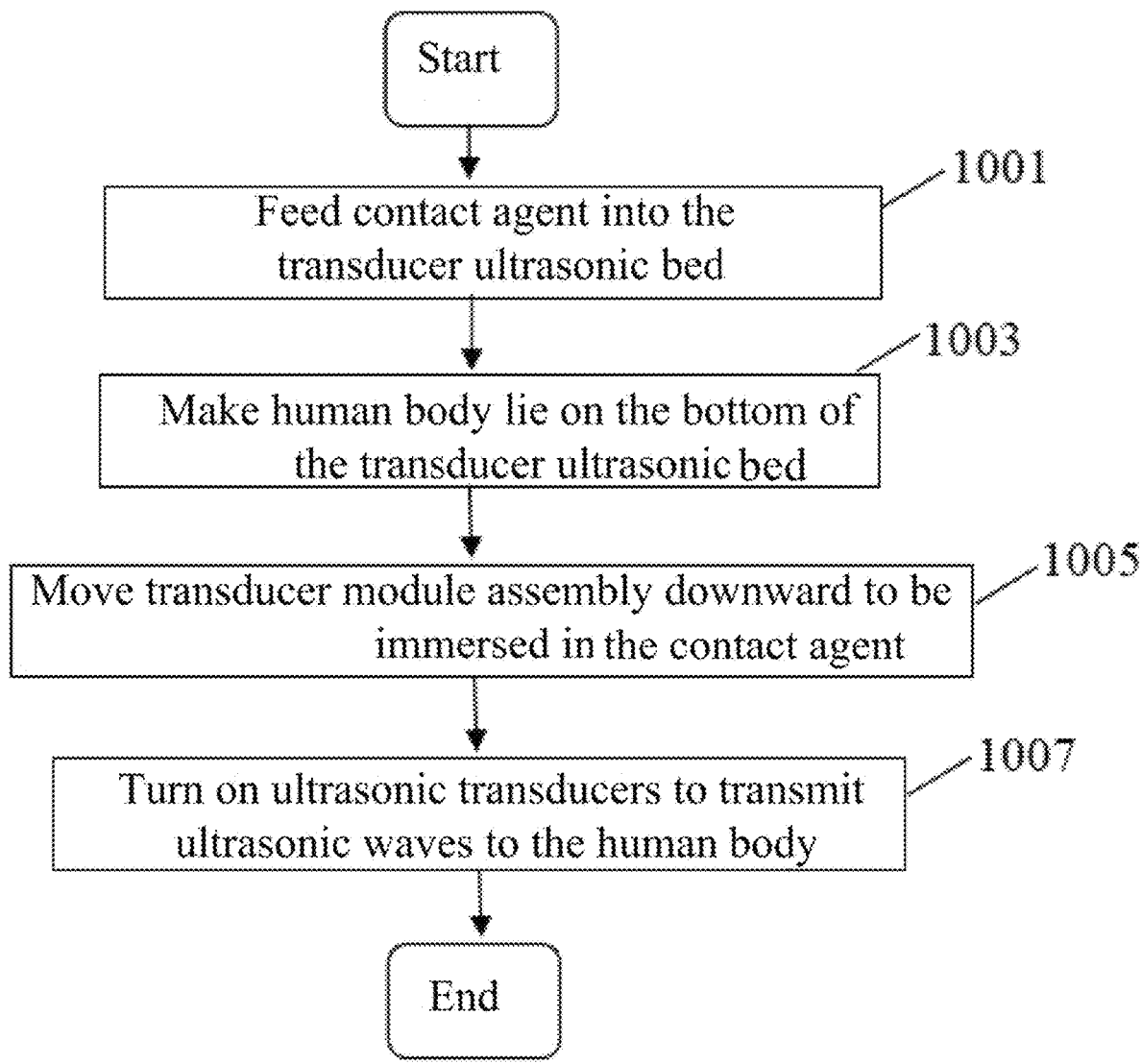
FIG. 19 shows a working flow chart of an ultrasound medical system 300 according to another embodiment of the present disclosure.

FIG. 19 shows a working flow chart of an ultrasonic medical system 300. As shown in FIG. 19, in step 1001, the contact agent is fed into the transducer ultrasonic bed, so that all the ultrasonic transducers in the transducer ultrasonic bed are immersed into the contact agent. In step 1003, the human body is made lie on the bottom of the transducer ultrasonic bed. In step 1005, the transducer module assembly is moved downward to be immersed in the contact agent. In step 1007, the ultrasonic transducers are turned on to transmit ultrasonic waves to the human body. The ultrasonic waves emitted from the ultrasonic transducers and the transducer module assembly have a frequency of 0.3-3 MHz and a waveform of continuous or a pulse wave. Preferably, enough contact agent is fed into the transducer ultrasonic bed, so that the human body can float in it, and a slight lateral drift thus occurs. The floatation and lateral drift can make the human body receive more intensive ultrasonic radiation in the transducer ultrasonic bed. Preferably, the contact agent is vacuum degassed (cold, hot) water. Preferably, the ultrasonic waves emitted from the ultrasonic bed is a pulse wave at a frequency of 1 MHz. Preferably, the ultrasonic waves emitted from the transducer ultrasonic bed are continuous waves at a frequency of 1 MHz. Preferably, the ultrasonic waves are simultaneously transmitted to the human body from the wall and bottom of the transducer ultrasonic bed. Preferably, the transducer module assembly transmits ultrasonic waves to the human body during horizontal movement.

Figure 20:
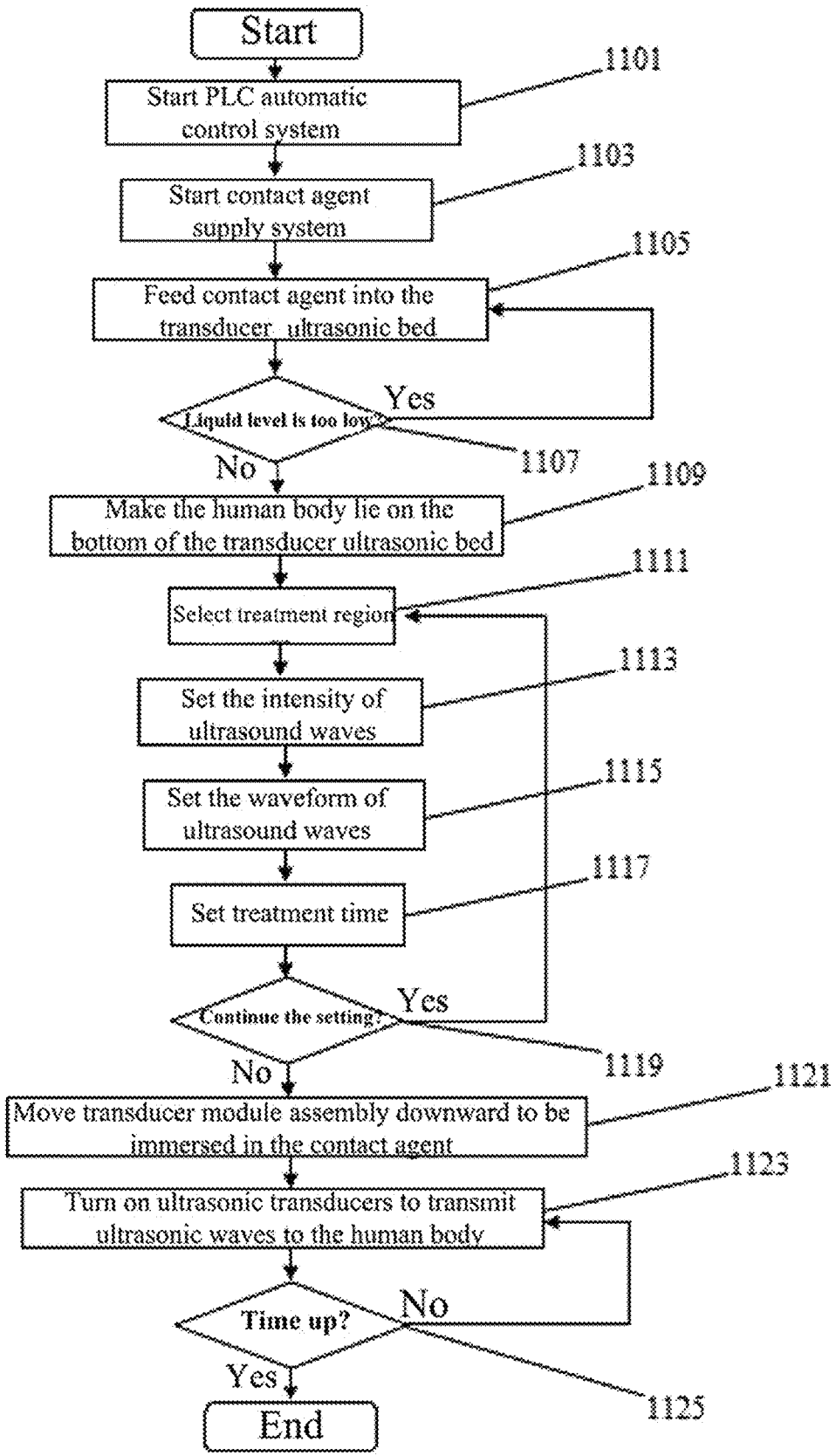
FIG. 20 shows a working flow chart of an ultrasound medical system 500 with a PLC automatic control system according to another embodiment of the present disclosure.
Figure 21:
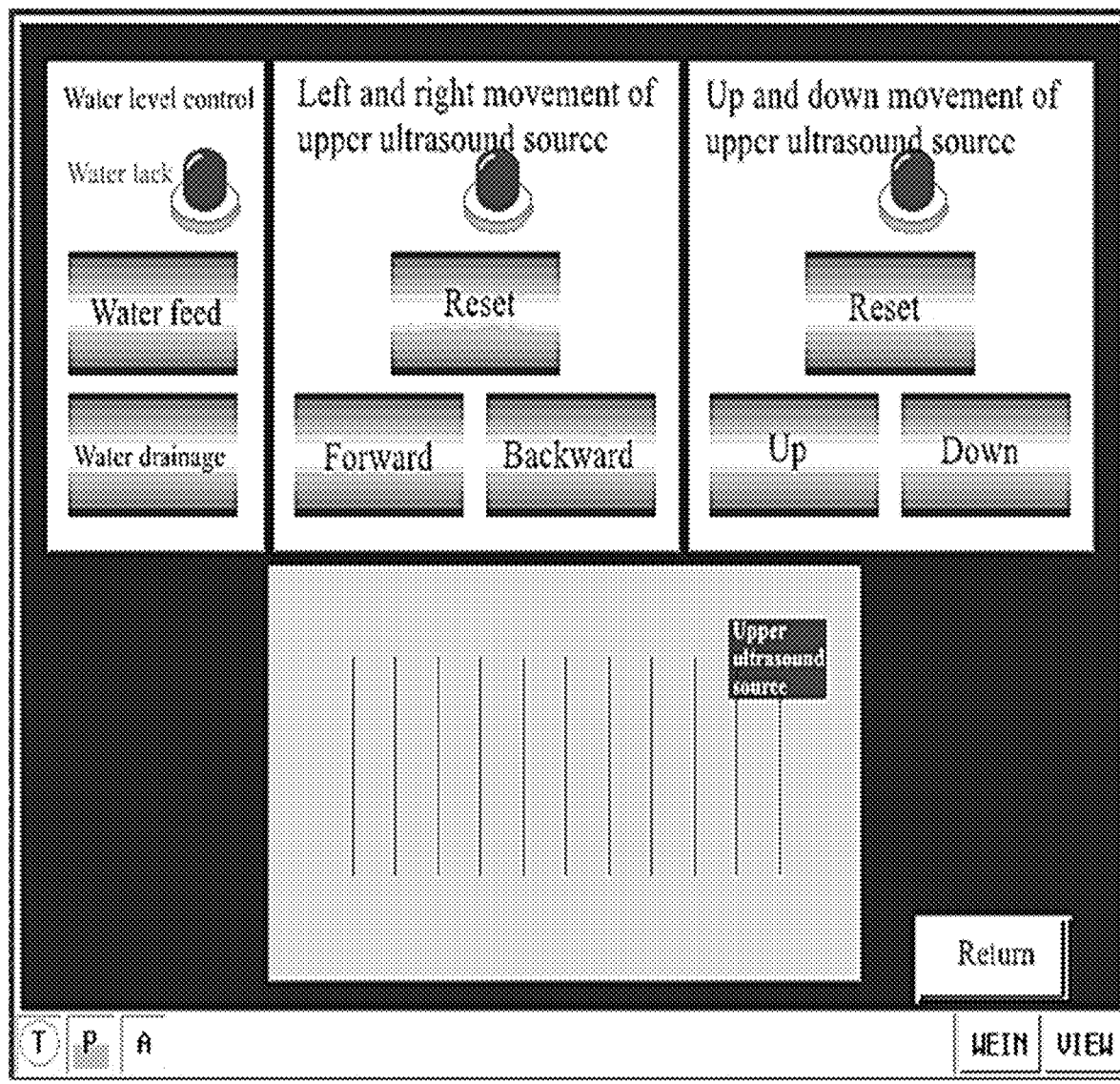
FIG. 21 shows a human-computer interface of the main screen of the PLC automatic control system according to the present disclosure.

FIG. 20 shows a working flow chart of an ultrasonic medical system 500. As shown in FIG. 20, in step 1101, the PLC automatic control system is started so that the medical system is remotely controlled through the human-machine interface, for example, the color touch screen as shown in FIG. 21, of the PLC automatic control system. In step 1103, the contact agent supply system is started. In step 1105, the contact agent supply system is started to feed the contact agent into the transducer ultrasonic bed. In step 1107, it is determined whether the liquid level of the contact agent in the transducer ultrasonic bed reaches the predetermined level, and if the liquid level is too low, go to step 1105, in order to continue to feed the contact agent into the transducer ultrasonic bed; otherwise, go to step 1109 to make the human body lie on the bottom of the transducer ultrasonic bed. In step 1111, the patient's region for treatment is selected, as shown in FIG. 22, for example, a local region may be selected for treatment, or systemic treatment may be selected according to the patient's condition. In step 1113, the intensity of the ultrasound waves is set for the selected region for treatment, for example, the ultrasound intensity is set to be in a range of 0.1-3 $W/cm^2$ at an interval of 0.1 $W/cm^2$, such as 0.1, 0.2, 0.3 . . . , 1.0, 1.1, 1.2 . . . , 2.5, 2.6, 2.7, 2.8, 2.9, 3.0 $W/cm^2$. In step 1115, the waveform of the ultrasonic wave, such as a pulse wave or a continuous wave, is set for the selected region for treatment. In step 1117, as shown in FIG. 23, the treatment time required for the selected region for treatment is set to, for example, 30 minutes. In step 1119, it is determined whether it is necessary to continue the setting. If it is necessary to continue the setting, go back to step 1111 to set the remaining regions; otherwise, go to step 1121. In step 1121, the transducer module assembly is moved downward to be immersed in the contact agent. In step 1123, the ultrasonic transducers in the selected region(s) for treatment and in the transducer module assembly are turned on, and ultrasonic waves are transmitted to the human body.

During the above-mentioned treatment, the PLC automatic control system can be used to suspend treatment at any time, so that the operations from step 1111 to step 1117 can be performed again, and the corresponding settings can be changed to meet the patient's treatment need in time. In step 1111, when selecting the region for treatment, only the ultrasonic transducer(s) in the transducer ultrasonic bed can be selected to work, or only the ultrasonic transducer(s) in the transducer module assembly can be selected to work, or both can be selected to work, depending on the patient's condition. More preferably, some of the ultrasonic transducers in the bottom of the transducer ultrasonic bed can be selected to work; or some of the ultrasonic transducers in the wall of the transducer ultrasonic bed can be selected to work; or some of the ultrasonic transducers in the bottom and some of ultrasonic transducers in the wall can be selected to work together; or only some of the ultrasonic transducers of the transducer module assembly can be selected to work; or some of the ultrasonic transducers of the transducer module assembly and some of the ultrasonic transducers in the bottom surface and/or in the wall of the transducer ultrasonic bed can be selected to work together. The specific selection depends on the need for treatment. In step 1113, when setting the intensity of the ultrasounds, the same or different ultrasound intensity can be selected according to the different conditions of the selected regions for treatment, and the ultrasound intensity is in a range of 0.1-3 $W/cm^2$. In step 1115, when setting the ultrasound waveform, pulse or continuous waveform can be selected according to the different conditions of the selected regions for treatment. The pulse mode can be 1%-99%, and preferably 30%, 50% or 75%, of the treatment time. In step 1117, when setting the treatment time, the treatment time can be selected to be 5-30 minutes according to the different conditions of the selected regions for treatment. In step 1123, when the ultrasonic transducers of the transducer module assembly are working, it can be fixed at a certain position above the human body to transmit ultrasonic waves to the human body, alternatively, it can move uniformly in the horizontal direction above the human body to transmit ultrasonic waves to the human body. The speed of movement is the ratio of the body's height to the treatment time.

More preferably, the PLC automatic control system can also be configured such that the ultrasonic transducers located in different regions irradiate the human body with different intensities.

It should be understood that the transducer module assembly may also be shaped into an upper cover, or a part of the upper cover of the transducer ultrasonic bed. In this case, the multiple ultrasonic transducers in the transducer module assembly can be distributed in the upper cover in various forms. The upper cover can cover the transducer ultrasonic bed after the subject to be treated lies on the transducer ultrasonic bed. In this case, the ultrasonic transducers transmit ultrasonic waves at a frequency of 0.3 MHz-3 MHz, and preferably 0.5, 1, or 1.5 MHz.

The system can effectively solve the problem of death of patients with malignant tumor caused by spread and metastasis of the malignant tumor. Ultrasound, which can irradiate the human body in all directions, can not only reach the tissues deep in the human body but also penetrate the human body. Energy of the ultrasound can successfully excite the sonosensitizer so as to kill the malignant tumor in various parts of the human body. In addition, according to the system, the ultrasonic transducer(s) can be flexibly selected during the sonodynamic therapy, thereby increasing the convenience in the process of the treatment by doctors and greatly shortening the treatment time for the patient. The present disclosure is performed with external ultrasound, has no damage to normal human tissues and kills malignant tumors without pain, and thus provides a new treatment system for malignant tumor with good selectivity and small side effects.

Although the present disclosure has been described in combination with preferred embodiments and specific examples, it is not intended to limit the scope of the present disclosure by the specific embodiments described above, because the embodiments herein are for illustration in all aspects and are not intended to limit. For example, in the above-mentioned embodiment, the described transducer module assembly is a rectangular component smaller than the transducer ultrasonic bed, but the transducer module assembly can also be manufactured in a structure complementary to the transducer ultrasonic bed, or any other suitable structure that can meet the treatment need. In addition, unless otherwise specified, any working flow proposed here should not be interpreted as requiring the steps to be executed in the specific order listed in the embodiments. Obviously, in addition to treating humans, the present disclosure can also be applied to animals or other subjects in need of treatment.

Although this description only mentions that the combination of the chlorin derivatives or the pharmaceutically acceptable salts thereof and the ultrasound medical system can be used to treat malignant tumors, the ultrasonic medical system provided by the present disclosure is also applicable for drug excitation, cardiovascular and cerebrovascular therapy, body beauty and physical therapy, etc.

The above is only the preferred embodiment of the present disclosure, and is not intended to limit the present disclosure. Any modifications, equivalents, improvements, etc., which are made within the spirit and principles of the present disclosure, should be included within the scope of the present disclosure.

What is claimed is:

1. A chlorin or a pharmaceutically acceptable salt thereof having a structure represented by following formula (I):

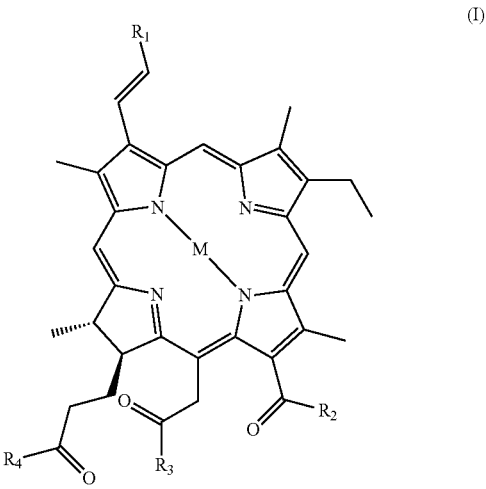

wherein, $R_1$ is

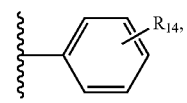

wherein $R_{14}$ is —H, $C_1$-$C_6$ alkoxy or $C_1$-$C_4$ haloalkyl; or

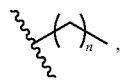

wherein n is any integer from 2 to 7;

$R_2$ is

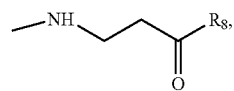

$C_1$-$C_6$ alkoxy or —OH, wherein $R_8$ is any of the following groups:

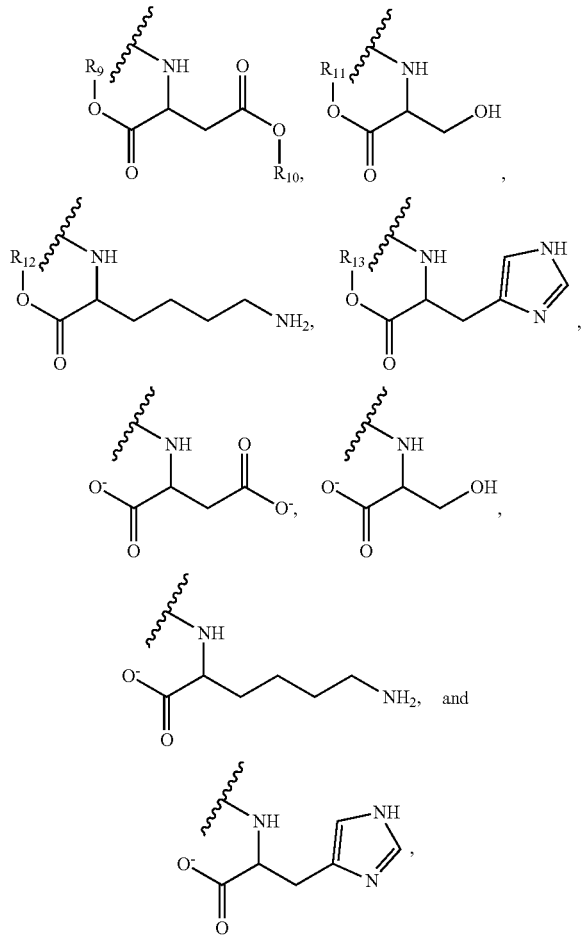

wherein $R_9$, $R_{10}$, $R_{11}$, $R_{12}$ and $R_{13}$ may be the same or different, and are each independently selected from $C_1$-$C_6$ alkyl, and when $R_2$ is

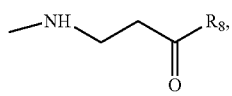

$R_3$ and $R_4$ are each independently selected from $C_1$-$C_6$ alkoxy or —OH;

when $R_2$ is $C_1$-$C_6$ alkoxy or —OH, one of $R_3$ and $R_4$ is any of the following groups:

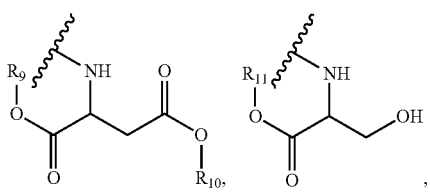

-continued

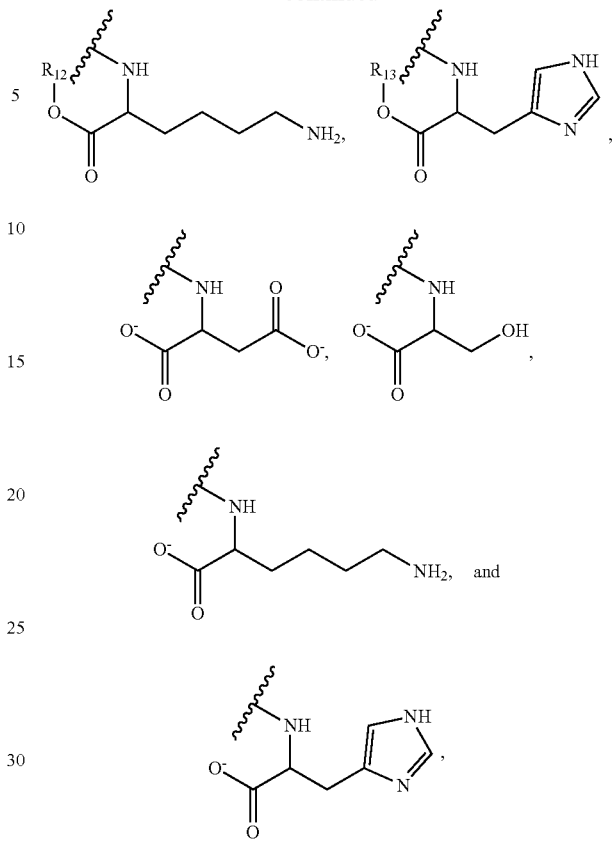

wherein $R_9$, $R_{10}$, $R_{11}$, $R_{12}$ and $R_{13}$ are defined as above, and the other of $R_3$ and $R_4$ is $C_1$-$C_6$ alkoxy or —OH; and M is 2H or a metal ion.

2. The chlorin or the pharmaceutically acceptable salt thereof according to claim 1, wherein the chlorin or the pharmaceutically acceptable salt thereof is:

(IIa)

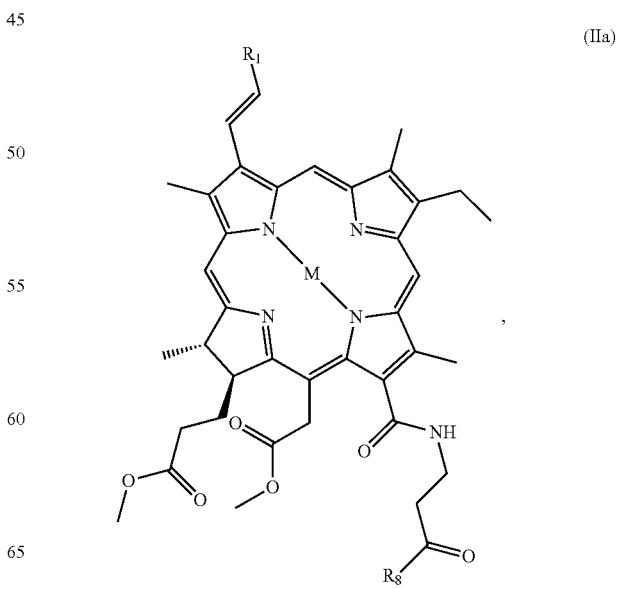

(IIb)
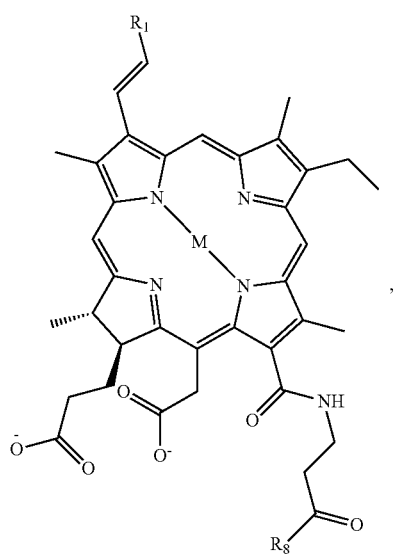
(IIIa)
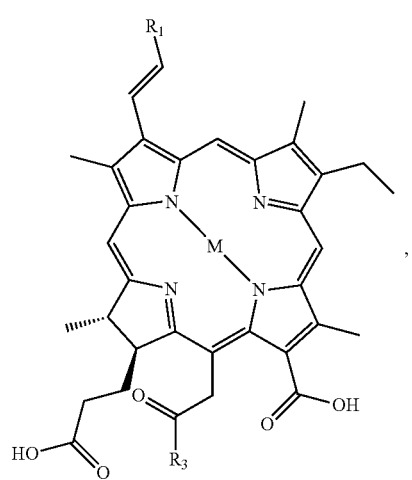
(IIIb)
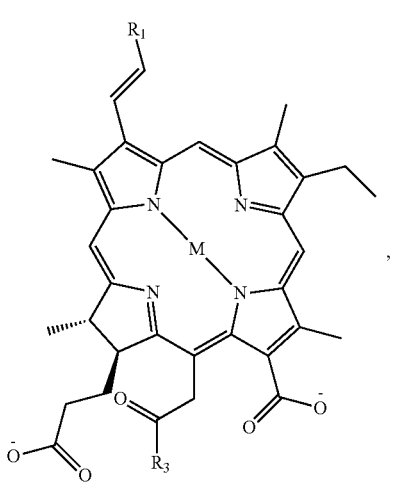
(IVa)
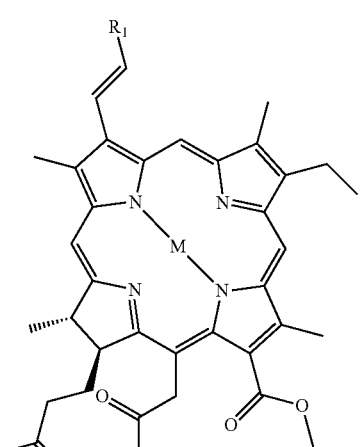
or
(IVb)
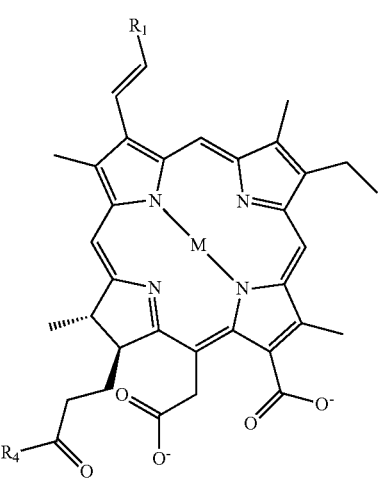
wherein,
$R_1$ is
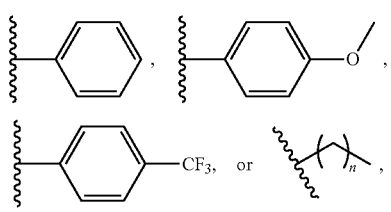
wherein n is any integer from 2-7;
$R_3$, $R_4$, and $R_5$ are any one of the following groups:
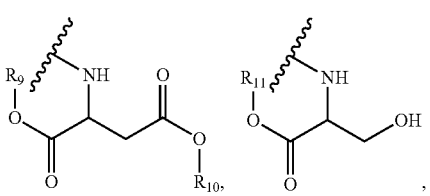

-continued
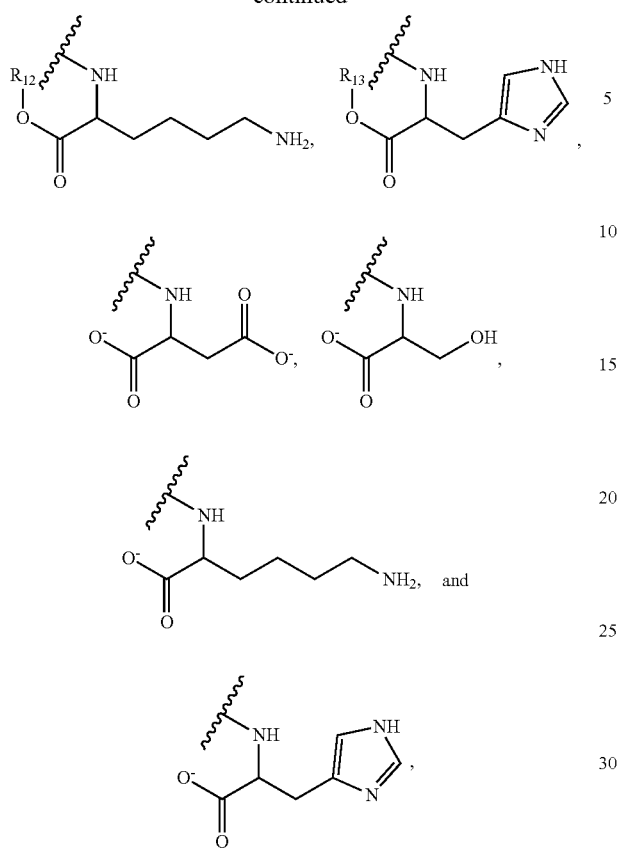
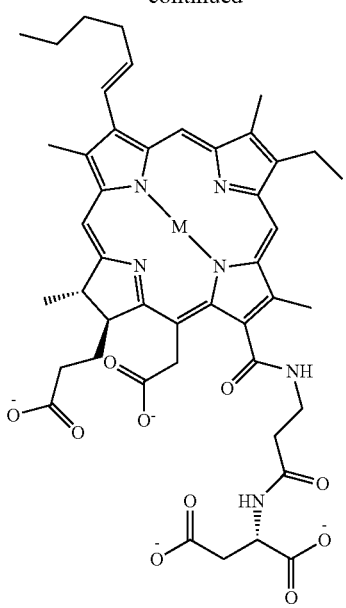
-continued
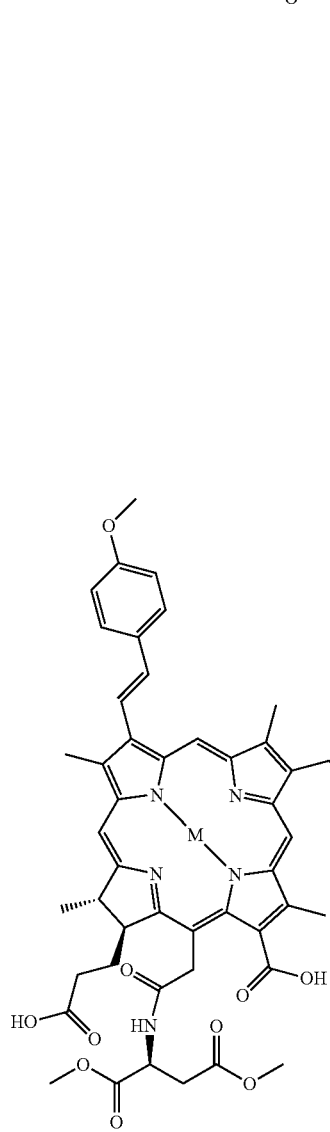
wherein $R_9$, $R_{10}$, $R_{11}$, $R_{12}$ and $R_{13}$ are defined as in claim 1; and
M is defined as in claim 1.
3. The chlorin or the pharmaceutically acceptable salt thereof according to claim 1, wherein the chlorin or the pharmaceutically acceptable salt thereof is
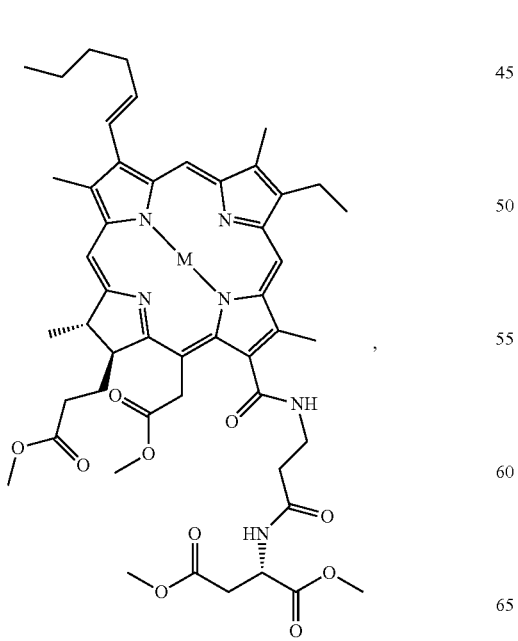

83
-continued
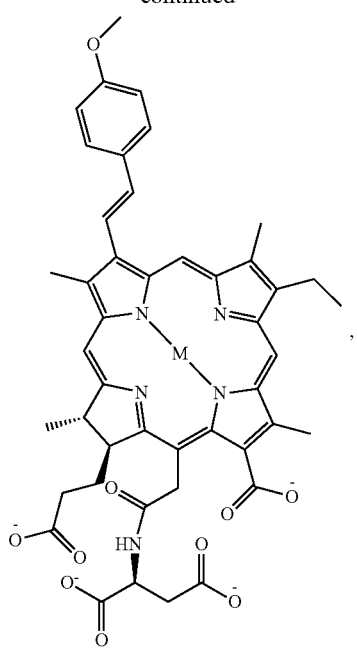
,
84
-continued
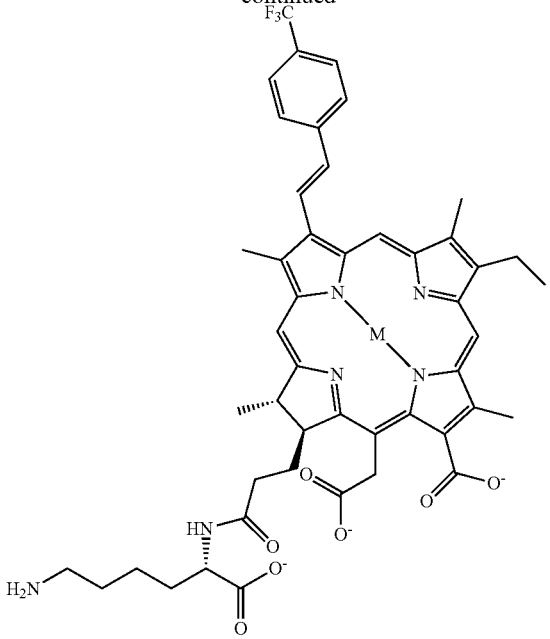
,
wherein M is defined as in claim 1.
4. A method for preparing the chlorin or the pharmaceutically acceptable salt thereof according to claim 1, wherein the method comprises the steps of:
$a_1$: subjecting compound 1 to esterification reaction with an alcohol to obtain compound 2:
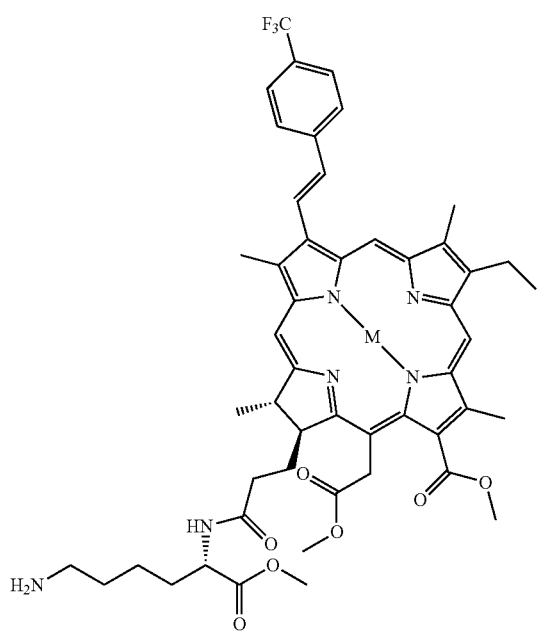
or
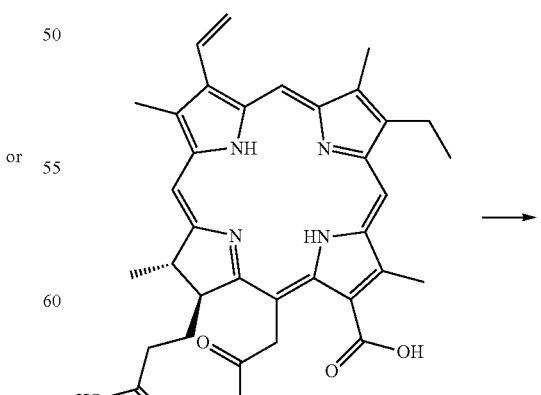
1
→

-continued
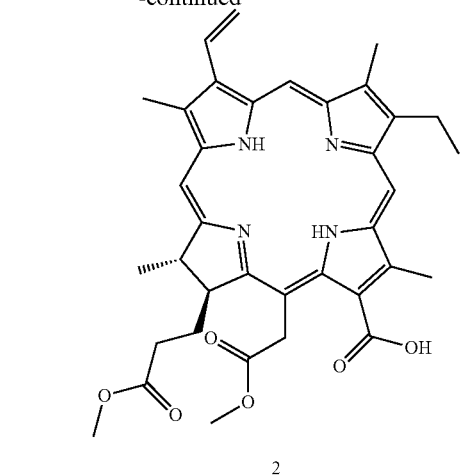
2
$b_1$: subjecting compound 2 to condensation reaction with β-alanine tert-butyl ester hydrochloride in the presence of a condensation agent to obtain compound 3:
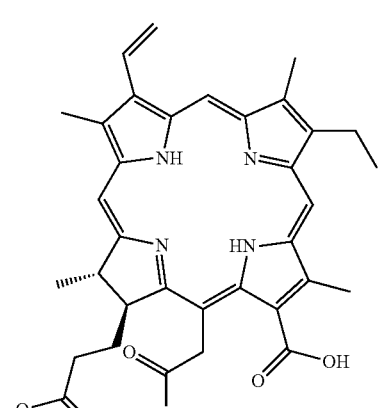
2
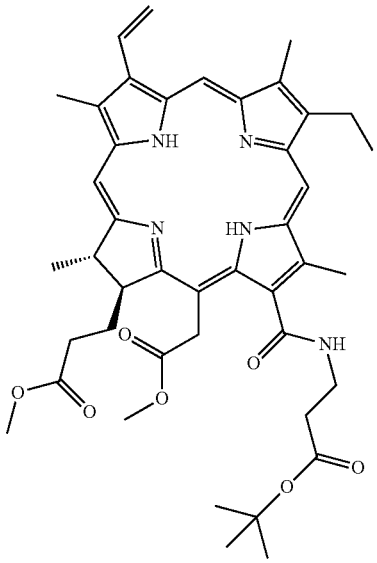
3
$c_1$: subjecting compound 3 to olefin metathesis reaction with a substituted α-olefin
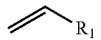
in the presence of a catalyst to obtain compound 4:
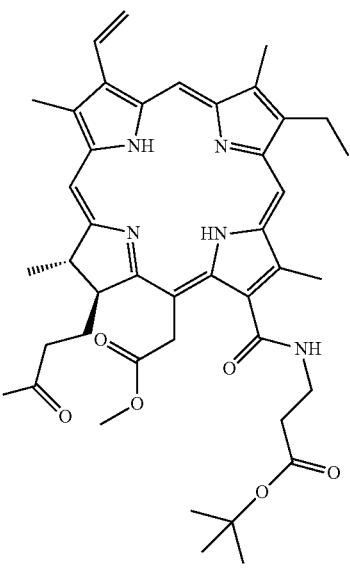
3
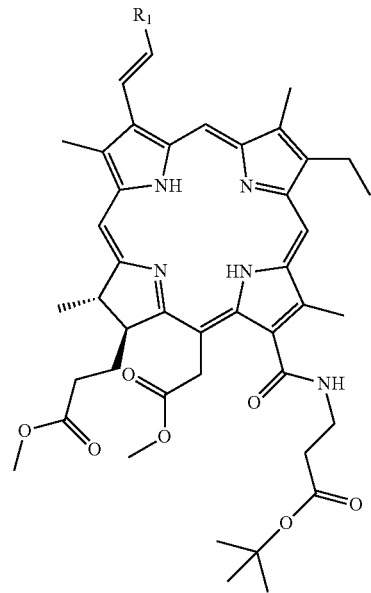
4
wherein $R_1$ is
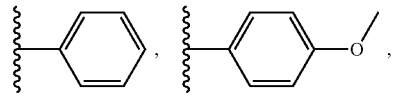

-continued

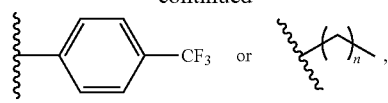

wherein n is any integer from 2 to 7;

$d_1$: subjecting compound 4 to hydrolysis reaction to obtain compound 5:

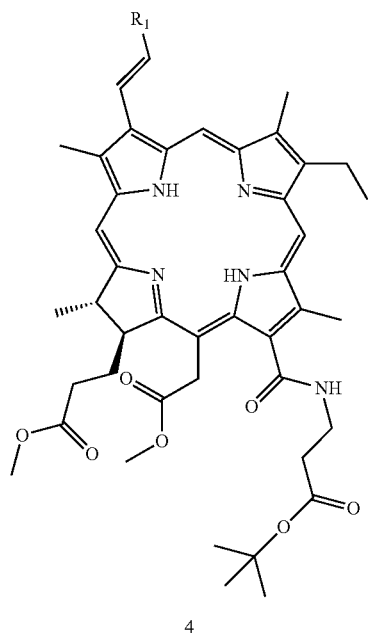

4

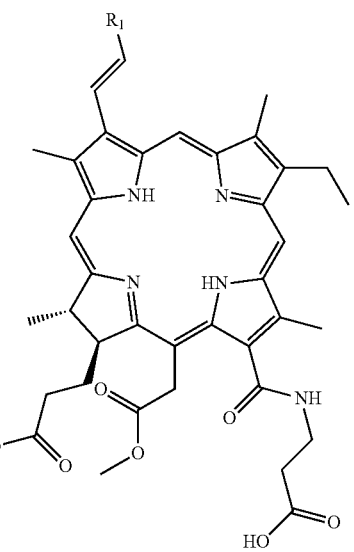

5

$e_1$: subjecting compound 5 to condensation reaction with an amino acid ester hydrochloride in the presence of a condensation agent to obtain a compound of formula II(a):

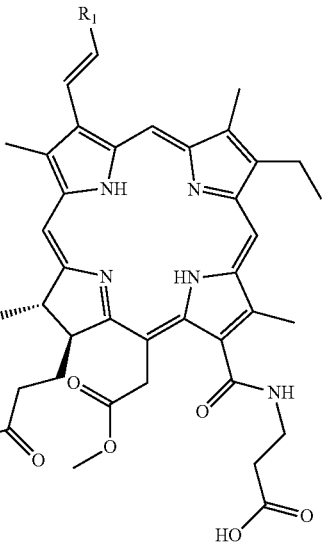

5

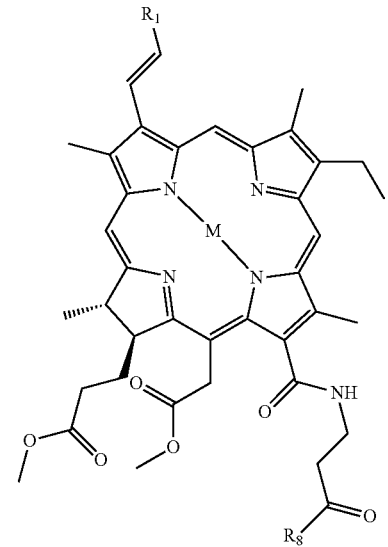

II(a)

wherein M is 2H, or a metal ion-upon reaction with a metal chloride or acetate complex, and wherein $R_8$ is defined as in claim 1; and optionally subjecting the compound of formula II(a) to hydrolysis reaction under alkaline conditions to obtain a corresponding salt, that is, a compound of formula II(b);

or alternatively, $a_2$: subjecting compound 1 to reaction with an alkyl halide under alkaline conditions to obtain compound 10:

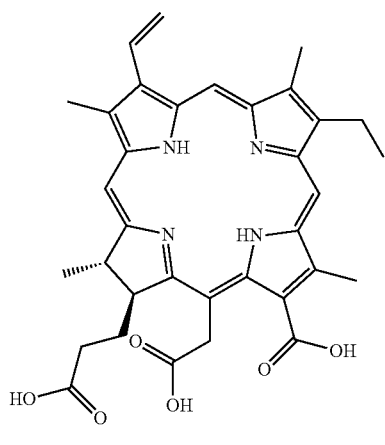
1
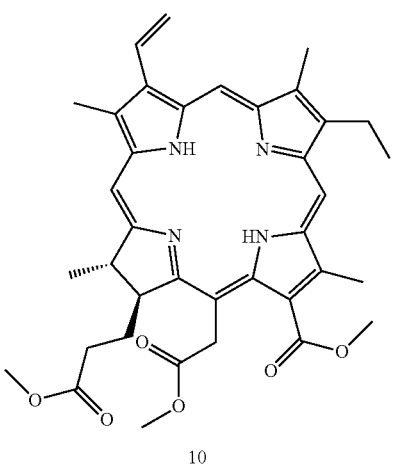
10
b$_2$: subjecting compound 10 to olefin metathesis reaction with a substituted α-olefin
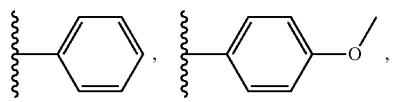
in the presence of a catalyst to obtain compound 11:
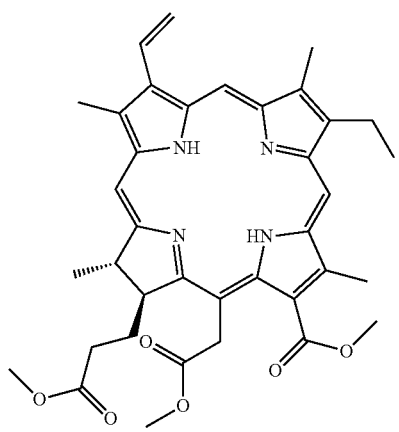
10
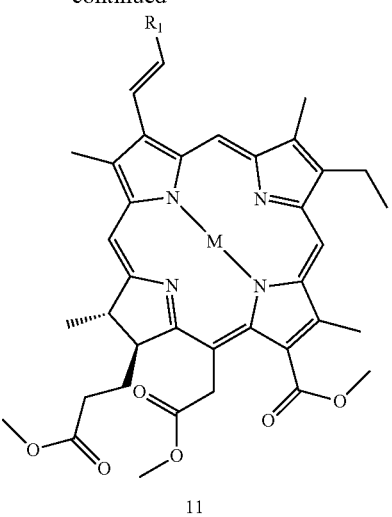
11
wherein R$_1$ is
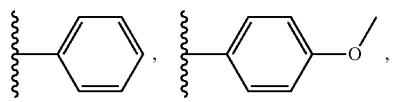
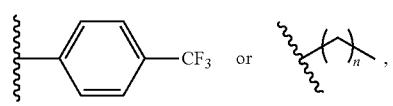
wherein n is any integer from 2 to 7,
wherein M is 2H, or a metal ion upon reaction with a metal chloride or acetate complex;
c$_2$: subjecting compound 11 to hydrolysis reaction under alkaline conditions to obtain compound 13:
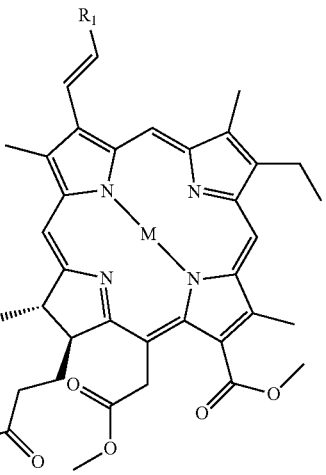
11

-continued

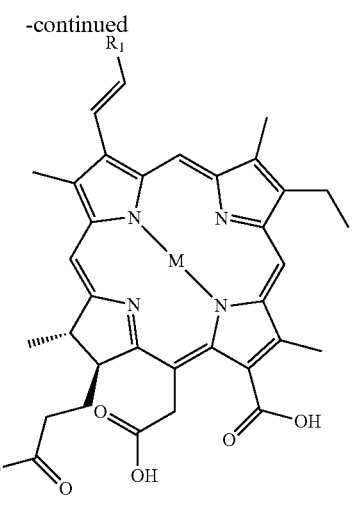

13 d$_2$: subjecting compound 13 to condensation reaction with an amino acid ester hydrochloride to obtain a compound of formula III(a):

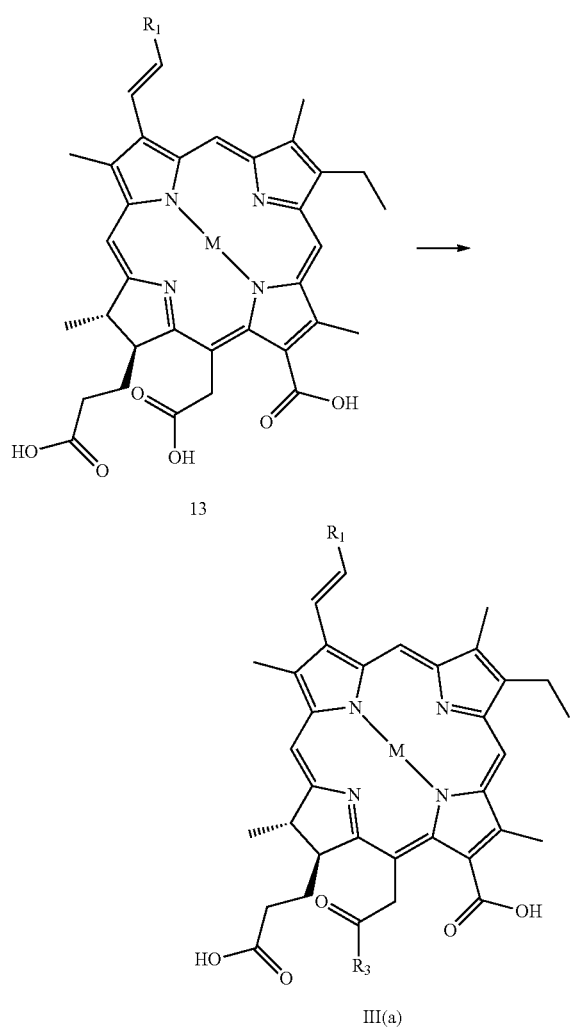

III(a)

wherein M is 2H, or a metal ion upon reaction with a metal chloride or acetate complex,
wherein R$_3$ is defined as in claim 1; and
optionally subjecting the compound of formula III(a) to hydrolysis reaction under alkaline conditions to obtain a corresponding salt, a compound of formula III(b);
or alternatively, a$_3$: subjecting compound 19 to condensation reaction with an amino acid ester hydrochloride in the presence of a condensation agent to obtain compound 20:

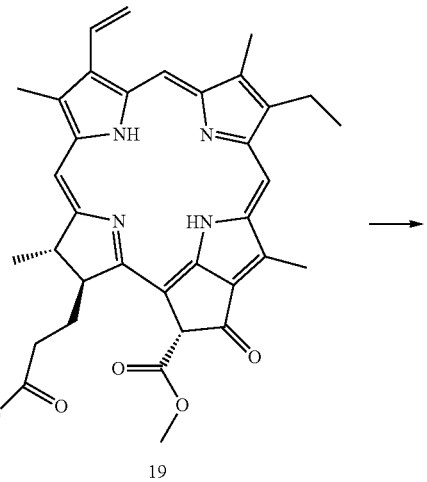

19

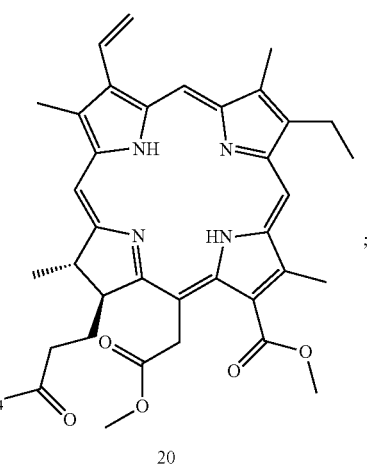

20 b$_3$: subjecting compound 20 to olefin metathesis reaction with a substituted α-olefin

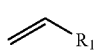

in the presence of a catalyst to obtain a compound of formula IV(a):

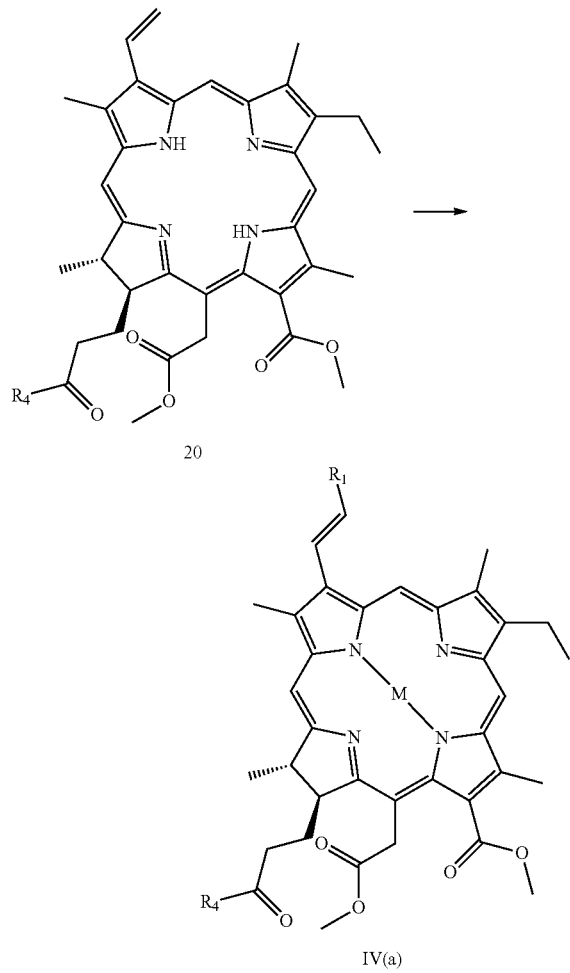

wherein $R_1$ is

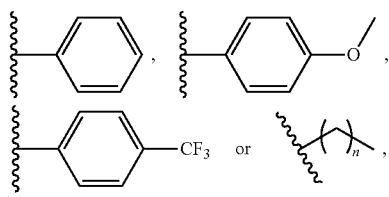

wherein n is any integer from 2 to 7,
wherein M is 2H, or a metal ion upon reaction with a metal chloride or acetate complex, and wherein $R_4$ is defined as in claim 1; and
optionally subjecting the compound of formula IV(a) to hydrolysis reaction under alkaline conditions to obtain a corresponding salt, that is, a compound of formula IV(b).

5. A pharmaceutical comprising the chlorin or the pharmaceutically acceptable salt thereof according to claim 1, and a pharmaceutically acceptable excipient.

6. A method of treating a tumor comprising administering the chlorin or the pharmaceutically acceptable salt thereof according to claim 1 to a subject having tumor cells, wherein the treatment is performed by photodynamic therapy or sonodynamic therapy.

7. The method according to claim 6, wherein the tumor comprises benign tumor and malignant tumor.

8. The method according to claim 7, wherein the photodynamic therapy is performed with light waves at a wavelength of 600-800 nm and the sonodynamic therapy is performed with ultrasounds at an intensity of 1.88 $W/cm^2$.

9. A combination of a chlorin or a pharmaceutically acceptable salt thereof and an ultrasonic medical system, wherein
the chlorin or the pharmaceutically acceptable salt thereof is the chlorin or the pharmaceutically acceptable salt thereof according to claim 1; and
the ultrasonic medical system comprises a transducer ultrasonic bed and a contact agent, wherein the transducer ultrasonic bed comprises a bottom and a wall extending upward from the bottom; the bottom is provided, at positions corresponding to head, torso, and limbs of a subject, respectively, with at least one ultrasonic transducer for transmitting ultrasonic waves to the subject thereon; the wall is provided, at positions corresponding to the head and limbs of the subject, respectively, with at least one ultrasonic transducer for transmitting ultrasonic waves to the subject; and the contact agent is used to transmit ultrasonic waves between the subject and the ultrasonic transducers.

10. The combination according to claim 9, wherein the ultrasonic medical system further comprises a transducer module assembly, wherein the transducer module assembly is installed above the transducer ultrasonic bed and comprises at least one ultrasonic transducer for transmitting ultrasonic waves to the subject therebelow; and the contact agent is also used to transmit ultrasonic waves between the subject and the at least one ultrasonic transducer.

11. The combination according to claim 10, wherein the transducer module assembly further comprises a numerically controlled motion device for controlling the movement of the transducer module assembly in a horizontal and/or vertical direction.

12. The combination according to claim 9, wherein the ultrasonic wave is a pulse wave or a continuous wave.

13. The combination according to claim 9, wherein the contact agent is at least one of water and vacuum degassed cold/hot water.

14. The combination according to claim 9, wherein the ultrasonic medical system further comprises an automatic control system with a programmable logic controller, and a contact agent supply system, wherein,
the contact agent supply system is connected to the transducer ultrasonic bed, so as to supply the contact agent to the transducer ultrasonic bed; and
the automatic control system with a programmable logic controller is respectively connected to the transducer ultrasonic bed, the transducer module assembly and the contact agent supply system, so as to control the supply of the contact agent from the contact agent supply system to the transducer ultrasonic bed, and to control the operation of at least some of the ultrasonic transducers in the transducer ultrasonic bed and in the transducer module assembly.

15. The combination according to claim 14, wherein the automatic control system with a programmable logic controller further comprises a monitoring system for displaying at least one of the following:

a. working parameters of at least some of the ultrasonic transducers in the transducer ultrasonic bed and the transducer module assembly; and
b. lesion information within the subject.

16. The chlorin or the pharmaceutically acceptable salt thereof according to claim 1, wherein the metal ion is a divalent metal ion or a tetravalent metal ion.

17. The chlorin or the pharmaceutically acceptable salt thereof according to claim 16, wherein the divalent metal ion is selected from $Cu^{2+}$, $Fe^{2+}$, $Zn^{2+}$, $Mg^{2+}$, $Ni^{2+}$, $Co^{2+}$, $Pt^{2+}$ or $Pd^{2+}$.

18. The chlorin or the pharmaceutically acceptable salt thereof according to claim 16, wherein the tetravalent metal ion is $Sn^{4+}$ or $Ti^{4+}$.

19. The method according to claim 4, wherein the metal ion is a divalent metal ion or a tetravalent metal ion.

20. The method according to claim 19, wherein the divalent metal ion is selected from $Cu^{2+}$, $Fe^{2+}$, $Zn^{2+}$, $Mg^{2+}$, $Ni^{2+}$, $Co^{2+}$, $Pt^{2+}$ or $Pd^{2+}$.

21. The method according to claim 19, wherein the tetravalent metal ion is $Sn^{4+}$ or $Ti^{4+}$.

22. The pharmaceutical composition according to claim 5, the pharmaceutical composition is an injection formulation.

23. The method according to claim 6, wherein the chlorin or the pharmaceutically acceptable salt thereof is in a form of an injection formulation.

24. The method according to claim 6, wherein the tumor is carcinoma in situ.

25. The method according to claim 24, wherein the carcinoma in situ is selected from breast cancer, liver cancer, lung cancer, and colorectal cancer.

26. The method according to claim 6, wherein the tumor is cancer metastasis.

27. The method according to claim 26, wherein the cancer metastasis is selected from breast cancer metastasis, liver cancer metastasis, lung cancer metastasis, and colorectal cancer metastasis.

28. The method according to claim 8, wherein the photodynamic therapy is performed with light waves at a wavelength of 660 nm.

29. The combination according to claim 12, wherein the ultrasonic wave has a frequency of 0.3-3 MHz.

30. The combination according to claim 12, wherein the ultrasonic wave has a ultrasound intensity of 0.1-3 $W/cm^2$.

* * * * *

UNITED STATES PATENT AND TRADEMARK OFFICE
CERTIFICATE OF CORRECTION

PATENT NO. : 12,011,482 B2
APPLICATION NO. : 17/404800
DATED : June 18, 2024
INVENTOR(S) : Weijie Zhao et al.

It is certified that error appears in the above-identified patent and that said Letters Patent is hereby corrected as shown below:

In the Claims

In Column 80, in Claim 2, Line 56, please delete "R3, R4, and R3 are any one of the following groups" and replace with -- R3, R4, and R8 are any one of the following groups --.

Signed and Sealed this
Twenty-ninth Day of October, 2024

Katherine Kelly Vidal
*Director of the United States Patent and Trademark Office*